United States Patent [19]

Ochiai et al.

[11] Patent Number: 5,185,330
[45] Date of Patent: Feb. 9, 1993

[54] PENAM DERIVATIVES AND SALTS THEREOF, AND ANTIBACTERIAL AGENT COMPRISING THE SAME

[75] Inventors: Hirokazu Ochiai; Yasuo Watanabe; Yoshiharu Murotani; Hirohiko Fukuda; Osamu Yoshino; Shinzaburo Minami, all of Toyama; Toshio Hayashi, Takaoka; Kaishu Momonoi, Shinminato, all of Japan

[73] Assignee: Toyama Chemical Co., Ltd., Tokyo, Japan

[21] Appl. No.: 540,697

[22] Filed: Jun. 20, 1990

[30] Foreign Application Priority Data

Jun. 22, 1989 [JP] Japan .................. 1-159899

[51] Int. Cl.$^5$ .................. A61K 31/425; C07D 499/00
[52] U.S. Cl. .................. 514/142; 540/201; 540/304
[58] Field of Search .................. 540/201, 504; 514/192

[56] References Cited

U.S. PATENT DOCUMENTS 4,717,767 1/1988 Sadaki et al. .................. 540/222
4,948,796 8/1990 Hiraiwa et al. .................. 514/254

Primary Examiner—Nicholas S. Rizzo
Assistant Examiner—Jyothsna Venkat
Attorney, Agent, or Firm—Oblon, Spivak, McClelland, Maier & Neustadt

[57] ABSTRACT

A penam derivative represented by the following general formula or a salt thereof:

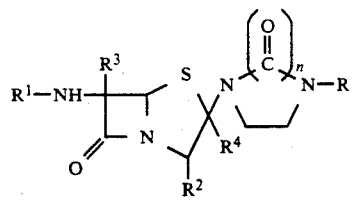

wherein $R^1$ represents a hydrogen atom, an amino-protecting group or an acyl group; $R^2$ represents a hydrogen atom or a lower alkyl group; $R^3$ represents a hydrogen atom, a lower alkoxy group, a lower alkylthio group or a formamido group; $R^4$ represents a protected or unprotected carboxy group or a craboxylato group; R represents a group of the formula, $-NHR^5$ or $-NR^5R^6$ (in which $R^5$ and $R^6$, which may be the same or different, represent protected or unprotected hydroxyl groups, cyano groups, sulfo groups, or unsubstituted or substituted lower alkyl, aryl, acyl, carbamoyl, sulfamoyl, lower alkylsulfonyl or heterocyclic groups) or a group of the formula, $-N=CR^7R^8$ (in which $R^7$ and $R^8$, which may be the same or different, represent hydrogen atoms or protected or unprotected carboxyl groups, cyano groups or unsubstituted or substituted lower alkyl, lower alkenyl, lower alkynyl, aryl, amino, acyl, acyloxy, carbamoyl, carbamoyloxy, sulfamoyl, lower alkylthio, ureido or heterocyclic groups, or $R^7$ and $R^8$ may form a cycloalkene or a heterocyclic ring with the carbon atom to which $R^7$ and $R^8$ are attached); and n represents 1 or 2. The above penam derivative or its salt is very effective as antibacterial agents.

51 Claims, No Drawings

PENAM DERIVATIVES AND SALTS THEREOF, AND ANTIBACTERIAL AGENT COMPRISING THE SAME

This invention relates to a novel penam derivative and a salt thereof, and more particularly, to a penam derivative represented by general formula [I] as hereinafter described or a salt thereof, a process for producing the same and an antibacterial agent containing the same.

Penam derivatives which are heretofore known, for example, compounds disclosed in Japanese Patent Application Kokai (Laid-Open) No. 183588/1988 have a relatively broad antibacterial spectrum. However, the antibacterial activities of the compounds against resistant bacteria are not satisfactory.

Under such circumstances, it has been desired that penam derivatives are developed which have a broad antibacterial spectrum, are stable to $\beta$-lactamases and exhibit a strong antibacterial activity against resistant bacteria.

The inventors of this invention have made extensive research on development of a compound capable of solving the above-mentioned problem, and consequently found penam derivatives of general formula [I] and salts thereof.

It is an object of this invention to provide a novel compound useful as a medicine for human beings and animals, which compound has a broad antibacterial spectrum, namely exhibits an excellent antibacterial activity to Gram-positive bacteria and Gram-negative bacteria, and in particular, is stable to $\beta$-lactamases and exhibits a strong antibacterial activity against resistant bacteria.

It is another object of this invention to provide a compound useful as an intermediate for the above-mentioned penam derivatives.

It is a further object of this invention to provide a processes for producing the above-mentioned penam derivatives.

It is a still further object of this invention to provide an antibacterial agent comprising the above-mentioned penam derivatives.

Other objects and advantages of this invention will become apparent from the following description.

According to this invention, there is provided a penam derivative represented by general formula [I] or a salt thereof:

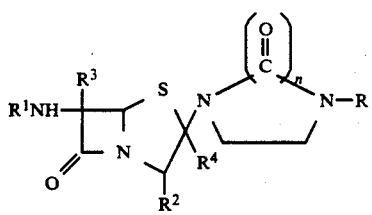

[I]

wherein $R^1$ represents a hydrogen atom, an amino-protecting group or an acyl group; $R^2$ represents a hydrogen atom or a lower alkyl group; $R^3$ represents a hydrogen atom, a lower alkoxy group, a lower alkylthio group or a formamido group; $R^4$ represents a protected or unprotected carboxyl group or a carboxylato group; R represents a group of the formula, $-NHR^5$ or $-NR^5R^6$ (in which $R^5$ and $R^6$, which may be the same or different, represent protected or unprotected hydroxyl groups, cyano groups, sulfo groups or unsubstituted or substituted lower alkyl, aryl, acyl, carbamoyl, sulfamoyl, lower alkylsulfonyl or heterocyclic groups), or a group of the formula, $-N=CR^7R^8$ (in which $R^7$ and $R^8$, which may be the same or different, represent hydrogen atoms or protected or unprotected carboxyl groups, cyano groups or substituted or unsubstituted lower alkyl, lower alkenyl, lower alkynyl, aryl, amino, acyl, acyloxy, carbamoyl, carbamoyloxy, sulfamoyl, lower alkylthio, ureido or heterocyclic groups, or $R^7$ and $R^8$ may form a cycloalkene or a heterocyclic ring with the carbon atom to which $R^7$ and $R^8$ are attached); and n represents 1 or 2.

In the present specification, the following terms have the following definitions unless otherwise specified.

The term "halogen atom" means fluorine atom, chlorine atom, bromine atom and iodine atom; the term "lower alkyl group" means straight or branched chain $C_{1-5}$alkyl group such as methyl, ethyl, n-propyl, isopropyl, n-butyl, isobutyl, sec-butyl, tert-butyl or pentyl; the term "lower alkenyl group" means straight or branched chain $C_{2-5}$alkenyl group such as vinyl, allyl, isopropenyl, butenyl or 2-pentenyl; the term "lower alkynyl group" means $C_{2-5}$alkynyl group such as ethynyl or 2-propynyl; the term "cycloalkyl group" means $C_{3-7}$cycloalkyl group such as cyclopropyl, cyclobutyl, cyclopentyl or cyclohexyl; the term "lower alkoxy group" means $C_{1-5}$alkoxy group such as methoxy, ethoxy or propoxy; the term "lower alkylthio group" means $C_{1-5}$alkylthio group such as methylthio, ethylthio or propylthio; the term "lower alkylthio-lower alkyl group" means $C_{1-5}$alkylthio-$C_{1-5}$alkyl group such as methylthiomethyl, ethylthiomethyl or ethylthioethyl; the term "halo-lower alkyl group" means halogen-substituted $C_{1-5}$alkyl group such as chloromethyl, bromomethyl or trifluoromethyl; the term "hydroxy-lower alkyl group" means hydroxy-$C_{1-5}$alkyl group such as hydroxymethyl, 2-hydroxyethyl or 3-hydroxypropyl; the term "amino-lower alkyl group" means amino-$C_{1-5}$alkyl group such as aminomethyl, 2-aminoethyl or 3-aminopropyl; the term "carboxy-lower alkyl group" means carboxy-$C_{1-5}$alkyl group such as carboxymethyl, 2-carboxyethyl or 3-carboxypropyl; the term "lower alkoxycarbonyl-lower alkyl group" means $C_{1-5}$alkyl-O—CO—$C_{1-5}$alkyl group such as methoxycarbonylmethyl, ethoxycarbonylmethyl or 2-ethoxycarbonylethyl; the term "cyano-lower alkylamino-lower alkyl group" means NC—$C_{1-5}$alkyl-NH—$C_{1-5}$alkyl group such as cyanomethylaminomethyl or 2-cyanoethylaminomethyl; the term "N,N-di-lower alkylamino group" means N,N-di-$C_{1-5}$alkylamino group such as N,N-dimethylamino; the term "lower alkylsulfonyl group" means $C_{1-5}$alkylsulfonyl group such as methylsulfonyl or ethylsulfonyl; the term "sulfamoyl-lower alkyl group" means sulfamoyl-$C_{1-5}$alkyl group such as sulfamoylmethyl or 2-sulfamoylethyl; the term "lower alkoxycarbonylamino group" means $C_{1-5}$alkyl-O—CO—NH-group; the term "lower alkoxyimino group" means $C_{1-5}$alkyl-O—N=group; the term "cycloalkyloxyimino group" means $C_{3-7}$cycloalkyl-O—N= group; the term "lower alkylidene group" means $C_{1-5}$alkylidene group such as methylidene or ethylidene; the term "lower alkenylidene group" means $C_{2-5}$alkenylidene group such as ethenylidene or propenylidene; the term "lower alkoxymethylene group" means $C_{1-5}$alkyl-O—CH= group; the term "halomethylene group" means halogen-substituted methylene group such as chloromethylene or bromomethylene; the term "lower alkanoyloxy group" means $C_{1-5}$alkyl-CO—O— group; the term "lower alkoxycarbonyl group" means $C_{1-5}$alkyl-O—CO— group; the term "carboxy-lower alkoxy group" means HOOC—$C_{1-5}$alkoxy group; the term "carboxy-lower alkylthio group" means HOOC—$C_{1-5}$alkylthio group; the term "acyl group" means formyl group, $C_{2-5}$alkanoyl group such as acetyl or propionyl $C_{3-5}$alkenoyl group such as acryloyl or crotonoyl, aroyl group such as benzoyl or naphthoyl or heterocyclic carbonyl group such as thenoyl, furoyl, isonicotinoyl, nicotinoyl, 1,4-dihydropyridin-2-ylcarbonyl or 4-ethyl-2,3-dioxopiperazin-1-ylcarbonyl; the term "acyloxy group" means acyl-O— group; the term "acylamino group" means acyl-NH— group; the term "aralkyl group" means benzyl group, phenethyl group, 4-methylbenzyl group or naphthylmethyl group; the term "aryl group" means phenyl group, naphthyl group or indanyl group; the term "haloaryl group" means halogen-substituted aryl group; the term "N,N'-di-lower alkylaminoaryl group" means N,N-di-$C_{1-5}$alkylaminoaryl group such as N,N-dimethylaminophenyl; the term "arylamino group" means aryl-NH— group; the term "arylcarbonylamino group" means aryl-CO—NH-group; the term "sulfamoylarylamino group" means $H_2NSO_2$-aryl-NH— group; the term "aralkyloxyimino group" means aralkyl-O—N= group; the term "cycloalkene" means $C_{5-6}$cycloalkene such as cyclopentene or cycloheptene; the term "heterocyclic group" means 4- to 7-membered or condensed or bridged heterocyclic group having 1-5 hetero atoms selected from oxygen, nitrogen and sulfur atoms such as azetidinyl, thienyl, furyl, pyrrolyl, 1,2,4-triazolyl, 1,2,3-triazolyl, oxazolyl, thiazolyl, tetrazolyl, 1,3-dithiolanyl, pyridyl, 1-hydroxy-4-oxo-1,4-dihydropyridyl, 1,4-dihydropyridyl, thiazolidinyl, oxazolidinyl, imidazolidinyl, pyrazolinyl, pyrrolidinyl, 2-oxazolinyl, imidazolinyl, furazanyl, isothiazolyl, 4,5-dihydrothiazolyl, 2,3-dihydrofuryl, 2,5-dihydrofuryl, tetrahydrofuryl, 1,2,3-thiadiazolyl, 1,2,4-thiadiazolyl, 1,3,4-thiadiazolyl, 1,2,5-thiadiazolyl, imidazolyl, pyrazolyl, 3-pyrrolinyl, 4,5-dihydropyrazolyl, isoxazolyl, isoxazolidinyl, 1,2,3-oxadiazolyl, 1,3,4-oxadiazolyl, 1,2,4-oxadiazolyl, piperidinyl, piperazinyl, tetrahydropyrazinyl, morpholinyl, pyrimidinyl, pyrazinyl, 1,2,4-triazinyl, 1,3,5-triazinyl, 2H-3,4-dihydropyranyl, 2H-5,6-dihydropyranyl, 1,4-oxazinyl, pyridazinyl, 2H-thiazinyl, perhydrooxazinyl, dihydrooxazinyl, chromenyl, benzothienyl, benzoisothiazolidinyl, imidazo[1,2-b][1,2,4]triazinyl, thieno[3,2-b]thienyl, benzotriazolyl, 1,2,3-benzothiadiazolyl, tetrazolo[5,1-b]pyridazinyl, 2,1,3-benzoxadianyl, imidazo[1,2-a]pyridyl, imidazo[1,2-a]pyrimidinyl, imidazo[1,2-b][1,3]thiazolyl, 5,6,7,8-tetrahydroimidazo[1,2-a]pyridyl, imidazo[1,2-a]pyrazinyl, 1,4-benzomorpholinyl, benzothiazolyl, isoindolinyl, benzofuranyl, 1,4-benzothiomorpholinyl, 1,3-benzoxazolidinyl, triazolo[1,5-a]pyrimidinyl, indolinyl, indazolyl, benzoxazolyl, benzoisoxazolyl, purinyl, isoquinolyl, quinolyl, 1,8-naphthyridinyl, 1,5-naphthyridinyl, 1,1-dioxo-1,2-benzoisothiazolidinyl, 1,2-dihydro-4H-3,1-benzoxazinyl, 1,2-benzoxazinyl, quinoxalinyl, quinazolinyl, cinnolinyl, indolyl, quinuclidinyl, perhydroazaepinyl or 3-pyrrolin-2-yl; the term "heterocyclic amino group" means heterocyclic ring-NH— group; the term "heterocyclic oxyimino group" means heterocyclic ring-O—N= group; the term "heterocyclic thio group" means heterocyclic ring-S— group; and the term "heterocyclic ring" means heterocyclic-H group. Incidentally, the heterocyclic group containing a nitrogen atom as the hetero atom may be quaternized.

The amino-protecting group in the definition of $R^1$ includes usually known amino-protecting groups, such as formyl, tert-butyloxycarbonyl, p-nitrobenzyloxycarbonyl, tert-amyloxycarbonyl, triphenylmethyl, trimethylsilyl, benzylidene, 2,2,2-trichloroethyloxycarbonyl or p-nitrobenzylidene and the like.

The acyl group in the definition of $R^1$ includes acyl groups which have heretofore been known in the penicillin and cephalosporin fields, for example, formyl, 2,6-dimethyloxyphenylcarbonyl, 5-methyl-3-phenylisoxazol-4-ylcarbonyl and the like and acyl groups represented by the formula:

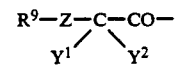

wherein $R^9$ represents an unsubstituted or substituted lower alkyl, lower alkenyl, aryl or heterocyclic group; Z represents an oxygen or sulfur atom or a linkage; $Y^1$ represents a hydrogen atom; $Y^2$ represents a hydrogen atom, a halogen atom, a protected or unprotected hydroxyl group, a protected or unprotected carboxyl group, a sulfo group, a sulfoamino group, a protected or unprotected amino group or a group of the formula, $R^{10}CONH—$ in which $R^{10}$ is an unsubstituted or substituted aryl, arylcarbonylamino, heterocyclic amino or heterocyclic group; and $Y^1$ and $Y^2$ may form, when taken together, an unsubstituted or substituted lower alkoxyimino, cycloalkyloxyimino, aralkyloxyimino, lower alkylidene, lower alkenylidene, lower alkoxymethylene, halomethylene or heterocyclic oxyimino group.

In the definition of $R^9$, the substituent for the substituted lower alkyl, lower alkenyl, aryl or heterocyclic group includes halogen atoms, hydroxyl group, amino group, amino-lower alkyl groups, acyloxy groups, carboxyl group, lower alkoxy groups, ureido group, acylamino groups, cyano group, sulfo group, carbamoyloxy group, sulfamoyl group, nitro group, oxo group, heterocyclic groups and the like. At least one of them may be attached to the lower alkyl, lower alkenyl, aryl or heterocyclic group for $R^9$ group.

In the definition of $R^{10}$, the substituent for the substituted aryl, arylcarbonylamino, heterocyclic amino or heterocyclic group includes, for example, halogen atoms, hydroxyl group, oxo group, lower alkyl groups, halo-lower alkyl groups, hydroxy-lower alkyl groups, lower alkylthio groups, lower alkylthio-lower alkyl groups, aryl groups, haloaryl groups, cycloalkyl groups, arylamino groups, lower alkylsulfonyl groups and sulfamoylarylamino groups. At least one of them may be attached to the aryl, arylcarbonylamino, heterocyclic amino or heterocyclic group for $R^{10}$ group.

The substituent for the substituted lower alkoxyimino, cycloalkyloxyimino, aralkyloxyimino, lower alkylidene, lower alkenylidene, lower alkoxymethylene, halomethylene or heterocyclic oxyimino group which $Y^1$ and $Y^2$ may form when taken together includes, for example, halogen atoms, acyloxy groups and protected or unprotected carboxyl groups. At least one of them may be attached to the group which $Y^1$ and $Y^2$ may form.

In the definition of $R^1$, the acyl group represented by the formula,

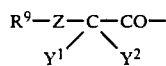

wherein $R^9$, $Y^1$, $Y^2$ and Z are as defined above includes, specifically 4-aminomethylphenylacetyl, hydroxyacetyl, phenoxyacetyl, 1-tetrazolylacetyl, cyanomethylthioacetyl, carboxyethylthioacetyl, (2-thienyl)acetyl, α-bromo-α-(2-thienyl)acetyl, α-amino-α-(2-thienyl)acetyl, (5-methoxy-2-thienyl)acetyl, phenylacetyl, (3-bromophenyl)acetyl, α-aminophenylacetyl, α-amino-α-(p-hydroxyphenyl)acetyl, α-amino-α-(2-aminothiazol-4-yl)acetyl, α-sulfoamino-α-(4-acetyloxyphenyl)acetyl, α-hydroxyphenylacetyl, α-carboxyphenylacetyl, α-carboxy-α-(p-hydroxyphenyl)acetyl, α-carboxy-α-(o-hydroxyphenyl)acetyl, α-carboxy-α-(m-hydroxyphenyl)acetyl, α-carboxy-α-(p-fluorophenyl)acetyl, α-carboxy-α-(p-acetyloxyphenyl)acetyl, α-carboxy-α-(p-carbamoyloxyphenyl)acetyl, α-carboxy-α-(3-fluoro-4-hydroxyphenyl)acetyl, α-carboxy-α-(3,4-dihydroxyphenyl)acetyl, α-carboxy-α-(o-chlorophenyl)acetyl, α-carboxy-α-(3-chloro-4-hydroxyphenyl)acetyl, α-carboxy-α-(2-chloro-4,5-dihydroxyphenyl)acetyl, α-carboxy-α-(3,4-diacetyloxy-6-chlorophenyl)acetyl, α-carboxy-α-(2-thienyl)acetyl, α-carboxy-α-(3-thienyl)acetyl, α-sulfophenylacetyl, α-sulfo-α-(p-acetyloxyphenyl)acetyl, α-sulfo-α-(m-acetyloxyphenyl)acetyl, α-sulfo-α-(p-nitrophenyl)acetyl, α-sulfo-α-(p-aminophenyl)acetyl, α-sulfo-α-(2-chloro-5-nitrophenyl)acetyl, α-sulfo-α-(3,4-dihydroxyphenyl)acetyl, α-sulfo-α-(3,4-diacetyloxyphenyl)acetyl, α-sulfo-α-(4-acetyloxy-3-fluorophenyl)acetyl, α-sulfo-α-(3,4-diacetyloxy-5-chlorophenyl)acetyl, α-sulfo-α-(3,4-diacetyloxy-6-chlorophenyl)acetyl, α-sulfo-α-(3,4-diacetyloxy-2-chlorophenyl)acetyl, α-sulfo-α-(5-amino-2-chlorophenyl)acetyl, α-sulfo-α-(4-acetyloxy-3-chloro-6-fluorophenyl)acetyl, α-sulfo-α-(4-acetyloxy-6-fluorophenyl)acetyl, α-sulfo-α-(3,4-diacetyloxy-6-fluorophenyl)acetyl, α-sulfo-α-(o-chlorophenyl)acetyl, α-sulfo-α-(p-chlorophenyl)acetyl, α-sulfo-α-(2-aminothiazol-4-yl)acetyl, α-sulfo-α-(3,4-diacetyloxy-5,6-dichlorophenyl)acetyl, α-sulfo-α-(p-hydroxyphenyl)acetyl, α-sulfo-α-(2-chloro-4,5-dihydroxyphenyl)acetyl, α-sulfo-α-(4-acetyloxy-2-chlorophenyl)acetyl, α-sulfo-α-(4-acetyloxy-3-chlorophenyl)acetyl, α-sulfo-α-(3,4-diacetyloxy-5-fluorophenyl)acetyl, α-sulfo-α-(4-acetyloxy-3-nitrophenyl)acetyl, α-sulfo-α-(4-acetyloxy-2,5-dichlorophenyl)acetyl, α-sulfo-α-(4-acetyloxy-2-chloro-5-methoxyphenyl)acetyl, α-sulfo-α-(2-chloro-4-nitrophenyl)acetyl, α-sulfo-α-(4-amino-2-chlorophenyl)acetyl, α-sulfo-α-(4-ureidophenyl)acetyl, α-sulfo-α-(3-acetylamino-4-hydroxyphenyl)acetyl, α-sulfo-α-(2-chloro-4-hydroxyphenyl)acetyl, α-sulfo-αα-(2-fluoro-4-hydroxyphenyl)acetyl, α-sulfo-α-(3-fluoro-4-hydroxyphenyl)acetyl, α-sulfo-α-(2-chloro-4ureidophenyl)acetyl, α-sulfonylamino-α-(4-acetyloxyphenyl)acetyl, α-sulfo-α-(4,5-diacetyloxy-3-fluorophenyl)acetyl, α-sulfo-α-(3-fluoro-4,5-dihydroxyphenyl)acetyl, α-sulfo-α-(2-chloro-4-hydroxy-5-methoxyphenyl)acetyl, α-sulfo-α-(4-acetylaminocarbonyloxy-3-fluorophenyl)acetyl, α-formyloxy-α-phenylacetyl, α-(4-ethyl-2,3-dioxo-1-piperazinecarboxamido)-α-phenylacetyl, α-(4-ethyl-2,3-dioxo-1-piperazinecarboxamido)-α-(p-hydroxyphenyl)acetyl, α-(4-ethyl-2,3-dioxo-1-piperazinecarboxamido)-α-(p-acetyloxyphenyl)acetyl, α-(4-ethyl-2,3-dioxo-1-piperazinecarboxamido)-α-(methylthio)acetyl, α-(4-ethyl-2,3-dioxo-1-piperazinecarboxamido)-α-(3,4-dihydroxyphenyl)acetyl, α-(4-ethyl-2,3-dioxo-1-piperazinecarboxamido)-α-(3,4-diacetyloxyphenyl)acetyl, α-(4-ethyl-2,3-dioxo-1-piperazinecarboxamido)-α-(3,4-diacetyloxy-6-chlorophenyl)acetyl, α-(4-ethyl-2,3-dioxo-1-piperazinecarboxamido)-α-(3,4-diacetyloxy-6-fluorophenyl)acetyl, α-(4-ethyl-2,3-dioxo-1-piperazinecarboxamido)-α-(6-chloro-3,4-dihydroxyphenyl)acetyl, α-(4-ethyl-2,3-dioxo-1-piperazinecarboxamido)-α-(6-fluoro-3,4-dihydroxyphenyl)acetyl, α-(4-cyclopropyl-2,3-dioxo-1-piperazinecarboxamido)-α-phenylacetyl, α-(4-ethyl-2,3-dioxo-1-piperazinecarboxamido)-α-(2-thienyl)acetyl, α-(4-ethyl-2,3-dioxo-1-piperazinecarboxamido)-α-(3-benzothienyl)acetyl, α-(4-ethyl-2,3-dioxo-1-piperazinecarboxamido)-α-(2-naphthyl)acetyl, 2-(2-aminothiazol-4-yl)-2-methoxyiminoacetyl, 2-(2-aminothiazol-4-yl)-2-(2-fluoroethoxyimino)acetyl, 2-(2-aminothiazol-4-yl)-2-carboxymethoxyiminoacetyl, 2-(2-aminothiazol-4-yl)-2-(1-carboxy-1-methylethoxyimino)acetyl, 2-(2-aminothiazol-4-yl)-2-[1-carboxy-1-(3,4-diacetyloxyphenyl)methoxyimino]acetyl, α-(2-oxo-1-imidazolidinecarboxamido)-α-phenylacetyl, α-(3-methylsulfonyl-2-oxo-1-imidazolidinecarboxamino)-α-phenylacetyl, α-(4-hydroxy-1,5-naphthyridine-3-carboxamido)-α-phenylacetyl, α-(4-phenyl-2,3-dioxo-1-piperazinecarboxamido)-α-phenylacetyl, α-[4-(2,4-dichlorophenyl)-2,3-dioxo-1-piperazinecarboxamido]-α-phenylacetyl, α-[(1,4-dihydroxy-4-oxopyridazin-2-yl)carboxamido]-α-phenylacetyl, α-[(5-hydroxy-4-oxo-1,4-dihydropyridin-2-yl)carboxamido]-α-phenylacetyl, α-[(5-hydroxy-4-oxo-1,4-dihydropyridin-2-yl)carboxamido]-α-(p-hydroxyphenyl)acetyl, α-[(1,5-dihydroxy-4-oxo-1,4-dihydropyridin-2-yl)carboxamido]-α-(p-hydroxyphenyl)acetyl, α-(2-aminothiazol-4-yl)-α-(4-ethyl-2,3-dioxo-1-piperazinecarboxamido)acetyl, α-(2-aminothiazol-4-yl)-α-[(5-hydroxy-4-oxo-1,4-dihydropyridin-2-yl)carboxamido]acetyl, α-[(4-oxo-4H-thiopyran-3-yl)carboxamido]-α-phenylacetyl and the like.

In the definition of $R^4$, the protecting group for the protected carboxyl group includes those carboxyl-protecting groups which are conventionally known in the penicillin and cephalosporin fields, for example, ester-forming groups which can be removed by catalytic reduction, chemical reduction or treatment under other mild conditions; ester-forming groups which can easily be removed in a living body; and organosilyl groups, organophosphorus groups and organotin groups which can easily be removed by treatment with water or alcohols; and the like. Of these protecting groups, preferable are lower alkyl groups such as methyl, propyl, tert-butyl and the like; aryl groups; aralkyl groups such as benzyl, 4-methoxybenzyl, 4-nitrobenzyl, 3,4-dimethoxybenzyl, 4-hydroxy-3,5-di(tert-butyl)benzyl, phenethyl, diphenylmethyl, triphenylmethyl, bis(methoxyphenyl)methyl and the like; phthalidyl group; halo-lower alkyl groups such as 2-iodoethyl, 2,2,2-trichloroethyl and the like; acyloxy-lower alkyl groups such as acetyloxymethyl, propionyloxymethyl, butyryloxymethyl, isobutyryloxymethyl, pivaloyloxymethyl, valeryloxymethyl, 1-acetyloxyethyl, 1-pivaloyloxyethyl, 1-acetyloxy-n-propyl, 1-pivaloyloxy-n-propyl and the like; 5-lower alkyl-2-oxo-1,3-dioxol-4-yl-lower alkyl groups such as 5-methyl-2-oxo-1,3-dioxol-4-yl-methyl and the like; lower alkoxy-lower alkyl groups such as methoxymethyl, ethoxymethyl, propoxymethyl, isopropoxymethyl and the like; lower alkoxycarbonyloxy-lower alkyl groups such as methoxycarbonyloxymethyl, 1-methoxycarbonyloxyethyl, 1-ethoxycarbonyloxyethyl, 1-propoxycarbonyloxyethyl and the like; etc.

In the definitions of $R^5$, $R^6$, $R^7$ and $R^8$, other groups than hydrogen atom, hydroxyl group, carboxyl group, cyano group and sulfo group, may be substituted by at least one substituent selected from halogen atoms, halo-lower alkyl groups, lower alkyl groups, lower alkoxy groups, carboxy-lower alkoxy groups, lower alkylthio groups, carboxy-lower alkylthio groups, lower alkanoyloxy groups, lower alkoxycarbonyl groups, diphenylmethyloxy-carbonyl groups, aryloxycarboxyl groups, hydroxy-lower alkyl groups, lower alkoxyimino groups, imino group, amino-lower alkyl groups, carboxy-lower alkyl groups, lower alkoxycarbonyl-lower alkyl groups, lower alkoxycarbonylamino groups, nitrobenzyloxycarbonylamino groups, cyano-lower alkylamino-lower alkyl groups, N,N-di-lower alkylamino groups, lower alkylsulfonyl groups, sulfamoyl-lower alkyl groups, aryl groups, aralkyl groups, carbamoyl group, sulfo group, acyl groups, oxo group, carboxyl group, nitro group, cyano group, amino group, hydroxyl group, ureido group, aralkyloxy groups, sulfamoyl group, thioxo group, methylenedioxy group, heterocyclic carbonyl groups, heterocyclic groups and heterocyclicthio groups and the like.

The substituent for each of $R^5$, $R^6$, $R^7$ and $R^8$ may further be substituted by at least one substituent selected from lower alkyl groups, amino group, oxo group, hydroxyl group, carbamoyl group, hydroxy-lower alkyl groups, carboxy-lower alkyl groups, N,N-di-lower alkylamino groups, acylamino groups, heterocyclic groups, ureido group, trimethylammonioacetyl groups and guanidino group and the like.

When each of $R^1$ and $R^4$ to $R^8$ has an amino group, a hydroxyl group or a carboxyl group, or when each of $R^1$ and $R^4$ to $R^{10}$ and the group which $Y^1$ and $Y^2$ form when taken together, has an amino group, a hydroxyl group or a carboxyl group, these groups may be protected by a conventionally known protecting group. The amino-protecting group includes, for example, the same amino-protecting groups mentioned in the definition of $R^1$; the hydroxyl-protecting group includes, for example, formyl, acetyl, benzyl, 4-methoxybenzyl, tetrahydropyranyl, benzyloxycarbonyl, trimethylsilyl and the like. Also, the carboxyl-protecting group includes, for example, the same carboxyl-protecting groups as mentioned in the definition of $R^4$.

The salts of the penam derivative of general formula [I] include conventionally known salts in basic groups such as amino group and the like and in the acidic groups such as carboxyl, sulfo, hydroxyl and the like.

The salts in the basic group include, for example, salts with mineral acids such as hydrochloric acid, sulfuric acid and the like; salts with organic carboxylic acids such as formic acid, citric acid, trichloroacetic acid, trifluoroacetic acid and the like; salts with sulfonic acids such as methanesulfonic acid, benzenesulfonic acid, p-toluenesulfonic acid, mesitylenesulfonic acid, naphthalenesultonic acid and the like, and the salts in the acidic groups include, for example, salts with alkali metals such as sodium, potassium and the like; salts with alkaline earth metals such as calcium, magnesium and the like; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procain, dibenzylamine, N-benzyl-$\beta$-phenethylamine, 1-ephenamine, N,N'-dibenzylethylenediamine and the like.

When the penam derivative of general formula [I] and salts thereof have isomers (for example, optical isomer, geometric isomer, tautomer and the like), this invention includes these isomers, and also includes all crystal forms, hydrates and solvates.

The penam derivatives of general formula [I] and salts thereof may form an intramolecular salts.

An explanation is made below of processes for producing the compound of this invention.

The penam derivative of general formula [I] and salt thereof can be produced by per se known processes or their appropriate combinations, for example, according to the following production routes.

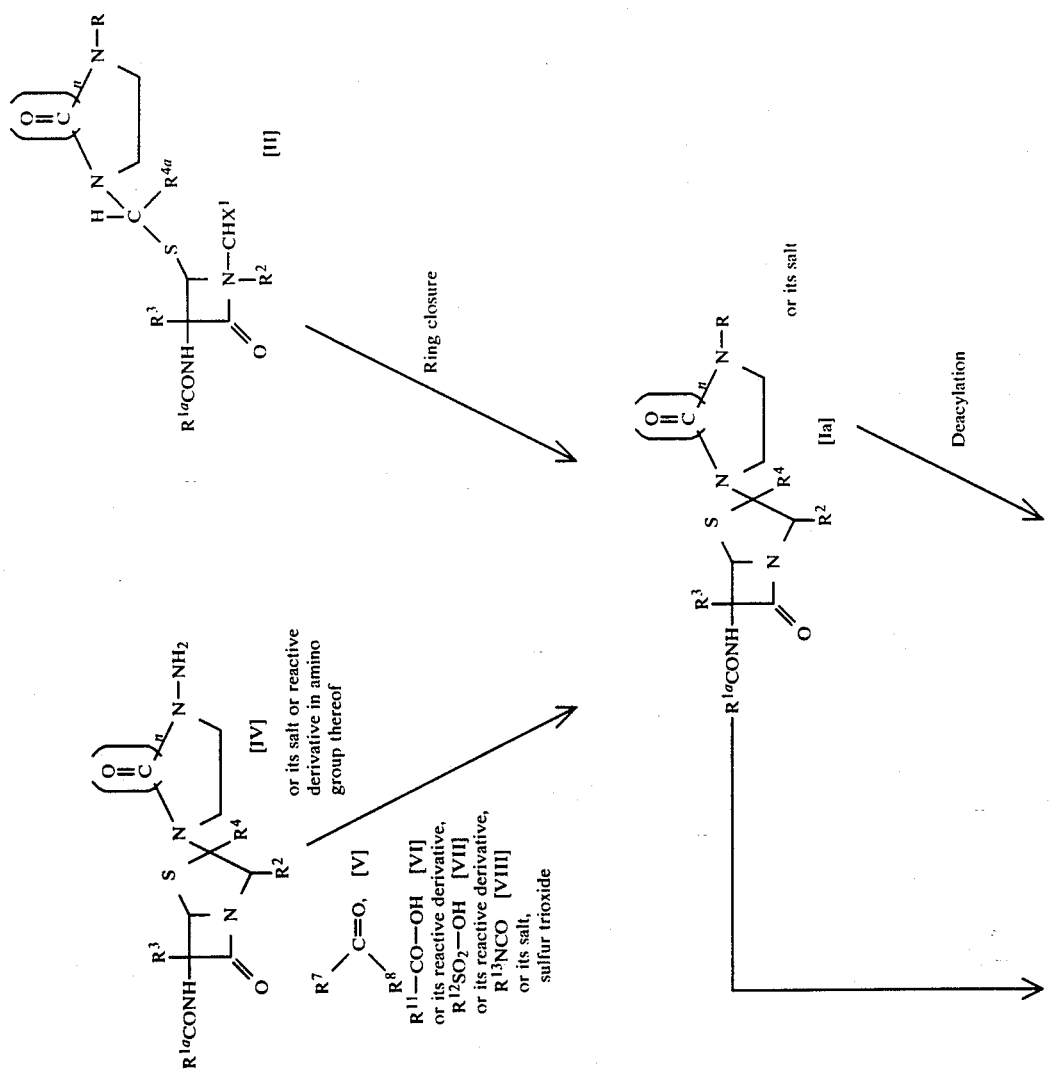

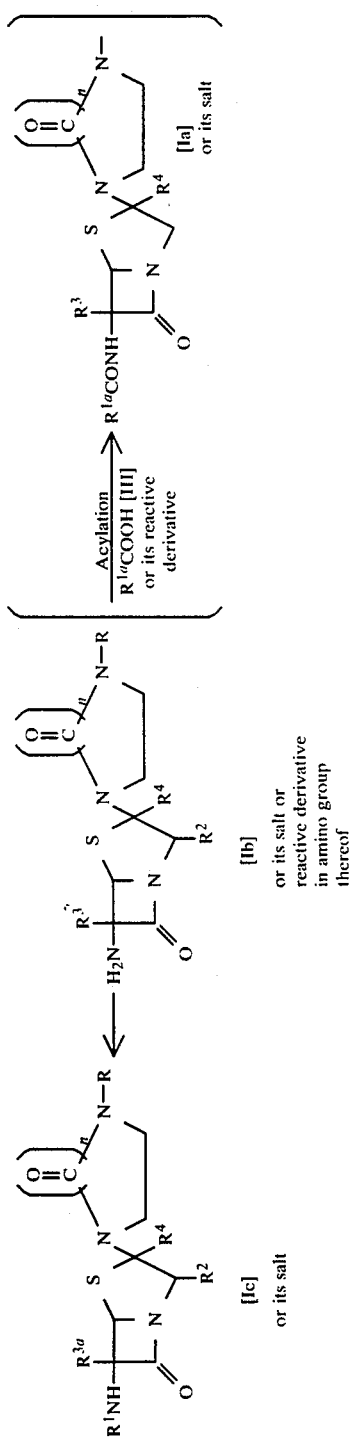

In the above formulas, R, $R^1$, $R^2$, $R^3$, $R^4$, $R^7$, $R^8$ and n are as defined above. $R^{1a}CO-$ means the same acyl group as in the definition of $R^1$, $R^{3a}$ means the same lower alkoxy, lower alkylthio or formamido group as in the definition of $R^3$, $R^{4a}$ means the same protected carboxyl group as in the definition of $R^4$, $R^{11}CO-$ means the same substituted acyl or unsubstituted group as in the definitions of $R^5$ and $R^6$, $R^{12}SO_2-$ means the same substituted or unsubstituted lower alkylsulfonyl group as in the definitions of $R^5$ and $R^6$, $R^{13}$ means a hydrogen atom or the same substituent for the carbamoyl group in the definitions of $R^5$ and $R^6$ and $X^1$ means a removable group.

Incidentally, the penam derivatives of general formulas [Ib] and [IV] are important intermediates for producing the compound of this invention.

The salts of the compounds of general formulas [Ia], [Ib], [Ic] and [IV] include the same salts as mentioned as to the salts of the compound of general formula [I].

The salt of the compound of general formula [VIII] includes salts with alkali metals such as sodium, potassium and the like and salts with alkaline earth metals such as calcium, magnesium and the like.

The removable group of $X^1$ includes halogen atoms; lower alkylsulfonyloxy groups such as methylsulfonyloxy, ethylsulfonyloxy and the like; arylsulfonyloxy groups such as phenylsulfonyloxy, toluenesulfonyloxy and the like; acyloxy groups such as acetyloxy, benzoyloxy and the like; etc.

The reactive derivatives in the amino group of the compound of general formula [Ib] or [IV] includes those reactive derivatives which are often used in acylation such as Schiff bases (isomer of imino type or its enamine type) produced by reaction of the compound of general formula [Ib] or [IV] or a salt thereof with a carbonyl compound such as an aldehyde, a ketone or the like; silyl derivatives produced by reaction of the compound of general formula [Ib] or [IV] or a salt thereof with an organosilyl compound such as N,O-bis(-trimethylsilyl)acetamide, trimethylsilylacetamide, trimethylsilyl chloride or the like; phosphorus derivatives produced by reaction of the compound of general formula [Ib] or [IV] or a salt thereof with a phosphorus compound such as 2-chloro-1,3,2-dioxaphosphorane, 2-chloro-4-methyl-1,3,2-dioxaphosphorane, 2-chloro-1,3,2-dioxaphosphorinane, chlorodiethyloxyphosphine, chlorodiethylphosphine, phosphorus trichloride or the like, or tin derivatives produced by reaction of the compound of general formula [Ib] or [IV] or a salt thereof with a tin compound such as chlorotriethylstannane or the like.

The reactive derivatives in the carboxylic acid of general formula [III] includes specifically acid halides, acid anhydrides; mixed anhydrides with monoalkyl carbonates such as monoethyl carbonate, monoisobutyl carbonate and the like; mixed anhydrides with optionally halogen-substituted lower alkanoic acids such as pivalic acid, trichloroacetic acid and the like; active acid amides such as N-acylimidazole, N-acylbenzoylamide, N,N'-dicyclohexyl-N-acylurea, N-acylsulfonamide and the like; active esters such as cyanomethyl ester, substituted phenyl ester, substituted benzyl ester, substituted thienyl ester and the like; and reactive derivatives produced by reaction of the carboxylic acid of general formula [III] with a Vilsmeier reagent (obtained by reacting an acid amide such as N,N-dimethylformamide or N,N-dimethylacetamide with a halogenating agent such as phosgene, thionyl chloride, phosphorus trichloride, phosphorus tribromide, phosphorus oxychloride, phosphorus pentachloride, trichloromethyl chloroformate, oxalyl chloride or the like); etc.

A more detailed explanation is further made below of the process for producing the compound of general formula [I] referring to the above-mentioned production route.

(1) Ring closure

The compound of general formula [Ia] or its salt can be produced by subjecting a compound of general formula [II] to ring closure reaction in the presence of a base.

The solvent to be used in this reaction may be any solvent as far as it does not adversely affect the reaction, and includes, for example, halogenated hydrocarbons such as methylene chloride, chloroform and the like; ethers such as tetrahydrofuran and the like; nitriles such as acetonitrile and the like; amides such as N,N-dimethylformamide, N,N-dimethylacetamide and the like; sulfoxides such as dimethylsulfoxide and the like; phosphoric acid amides such as hexamethylphosphoric acid triamide and the like; etc. These solvents may be used alone or in admixture of two or more.

The base to be used in this reaction includes inorganic and organic bases, for example, alkali hydroxides such as sodium hydroxide, potassium hydroxide and the like; alkali hydrogencarbonates such as sodium hydrogencarbonate and the like; alkali carbonates such as sodium carbonate and the like; metal hydrides such as sodium hydride, calcium hydride and the like; alkali acetate such as sodium acetate and the like; potassium tert-butoxide; diethylamine; triethylamine; lithium diisopropylamide; lithium bis(trimethylsilyl)amide; cyclohexylamine; pyridine; 2,6-lutidine; N-methylpiperidine; N-methylmorpholine; tetramethylguanidine; 1,8-diazabicyclo[5.4.0]undec-7-ene; methylmagnesium bromide; 2,4,6-trimethylphenylmagnesium bromide; and the like.

The amount of the base used is 1–5 moles, preferably 1.0 to 1.5 moles, per mole of the compound of general formula [II].

The reaction temperature and reaction time are not critical; however, usually the reaction may be carried out at $-60°$ to $30°$ C., preferably $-40°$ to $5°$ C., for 5 minutes to 2 hours.

The compound of general formula [Ia] or its salt thus obtained may be used as it is without being isolated in the subsequent reaction.

In the above reaction, when the compound of general formula [II] has bonded thereto a group having acidic proton such as an amido group or the like, a silylating agent, for example, N,O-bis(trimethylsilyl)acetamide or the like may be added to increase the yield.

(2) Deacylation

The compound of general formula [Ib] or its salt can be obtained by subjecting a compound of general formula [Ia] or its salt to conventional deacylation (for example, reacting the compound of general formula [Ia] or its salt with phosphorus pentachloride to form an iminochloride, then reacting it with an alcohol to form an iminoether and thereafter hydrolyzing the same).

This deacylation can be carried out by a deacylation method which is conventionally used in the penicillin and cephalosporin fields, for example, the method disclosed in, for example, Recl. Trav. Chim. Pays-Bas, vol.

89, p. 1081 (1973) or Japanese Patent Application Kokoku No. 38,954/1980 or a method similar thereto.

The compound of general formula [Ib] or its salt obtained by the above reaction can be used as it is without being isolated in the subsequent reaction.

(3) (i) Acylation

The compound of general formula [Ia] or its salt can be produced by reacting a compound of general formula [Ib] or its salt or a reactive derivative in the amino group thereof with a carboxylic acid of general formula [III] or a reactive derivative thereof.

This acylation may be usually carried out in the presence or absence of a base in an appropriate solvent.

The solvent to be used in this reaction may be any solvent as far as it does not adversely affect the reaction, and includes, for example, halogenated hydrocarbons such as methylene chloride, chloroform and the like; ethers such as tetrahydrofuran, dioxane and the like; amides such as N,N-dimethylformamide, N,N-dimethylacetamide and the like; ketones such as acetone and the like; water; and the like. These solvents may be used alone or in admixture of two or more.

The base which is optionally used in the above reaction includes the same bases as mentioned in (1) above.

When the compound of general formula [III] is used in the form of a free acid, an appropriate condensing agent is used. Such a condensing agent includes, for example, N,N'-di-substituted carbodiimide such as N,N'-dicyclohexylcarbodiimide or the like; 1,1'-carbonyldiimidazole; dehydrating agents such as N-ethoxycarbonyl-2-ethoxy-1,2-dihydroxyquinoline, phosphorus oxychloride, alkoxyacetylene or the like; and 2-halogenopyridinium salts such as 2-chloropyridinium methyliodide, 2-fluoropyridinium methyliodide and the like.

The amount of the carboxylic acid of general formula [III] or its reactive derivative used is 1.0 to 1.5 moles per mole of the compound of general formula [Ib] or its salt or reactive derivative in the amino group thereof.

The reaction temperature and reaction time are not critical; however, the reaction may be usually carried out at $-50°$ to $40°$ C. for 10 minutes to 48 hours.

(ii) Alternatively, the compound of general formula [Ia] or its salt can also be produced by reacting a compound of general formula [IV] or its salt or a reactive derivative in the amino group thereof with a compound of general formula [V] or a compound of general formula [VI] or [VII] or their salts or reactive derivatives thereof, or a compound of general formula [VIII] or its salt or sulfur trioxide.

These reactions can be carried out by a method known per se, for example, the acylation mentioned in (3)(i) above, the method described in Advanced Organic Chemistry, Reactions Mechanisms and Structures, second edition, pp. 382-388 and 823 (1977), the Journal of Antibiotics, vol. 31, pp. 546-560 (1978) and id., vol. 42, p. 1418 (1988) and Journal of American Chemical Society, pp. 5349-5351 (1956) and the like or a method similar thereto.

In each of the above-mentioned production routes when the compounds have a hydroxyl group, an amino group or a carboxyl group, it is possible to previously protect these groups with a conventional protective group and to remove, after the reaction, the protective group, if necessary, according to a per se known method.

The compound of general formula [Ic] or its salt in which $R^{3a}$ is a lower alkoxy group can be derived from a compound of general formula [Ia] or its salt in a conventional manner. The compound of general formula [Ic] or its salt in which $R^{3a}$ is a lower alkylthio group can be obtained by protecting the amino group of the compound of general formula [Ib] or its salt with, for example, the above-mentioned amino-protecting group, thereafter introducing a lower alkylthio group thereinto and, if necessary, removing the protecting group and thereafter subjecting the product to the acylation mentioned in (3)(i) above. The compound of general formula [Ic] or its salt in which $R^{3a}$ is a formamido group can be obtained by formamidation, of, for example, a compound of general formula [Ic] or its salt in which $R^{3a}$ is a lower alkylthio group. The introduction of a lower alkylthio group and the formamidation can be carried out by the method described in, for example, Japanese Patent Application Kokai (Laid-Open) No. 38,288/1983 or a method similar thereto.

The compounds of general formulas [Ia], [Ib] and [Ic] in which $R^4$ is a carboxyl group can be obtained by subjecting compounds of general formulas [Ia], [Ib] and [Ic] in which $R^4$ is a protected carboxyl group, respectively, to conventional removal of carboxyl-protecting group.

The compound of this invention thus obtained can be converted into other compounds of this invention by subjecting the former to conventionally known reactions or their appropriate combinations, for example, esterification, hydrolysis, addition reaction, acylation, oxidation, reduction, cyclization, halogenation, alkylation, amidation, alkylidenation, Wittig reaction and the like. These reactions can be carried out by the methods specifically described in, for example, Russ. Chem. Revs., vol. 33, pp. 66-77 (1964) and the like or a method similar thereto.

When there are isomers of the compound of general formula [Ia] or its salt; the compound of general formula [II]; the compound of general formula [Ib] or [IV] or its salt or reactive derivative in the amino group thereof; the carboxylic acid of general formula [III] or [VI] or its reactive derivative; and the compound of general formula [VII] or its reactive derivative (for example, optical isomers, geometric isomers, tautomers and the like), all of these isomers can be used. In addition, all crystal forms, hydrates and solvates can be used.

The compound of general formula [I] or its salt of this invention thus obtained can be isolated and purified by a conventional method such as extraction, crystallization, distillation, chromatography and the like.

Next, an explanation is made of a process for producing the compound of general formula [II] and the compound of general formula [IV] or its salt or reactive derivative in the amino group thereof which is the starting material for producing the compound of this invention.

The compound of general formula [IV] or its salt or reactive derivative in the amino group thereof can be obtained by a method known per se such as the method described in, for example, Tetrahedron Letters, pp. 375-378 and 4917-4920 (1972) or a method similar thereto.

The compounds of general formula [II] can be obtained by per se known processes or their appropriate combinations. For example, they can be produced according to the following production route.

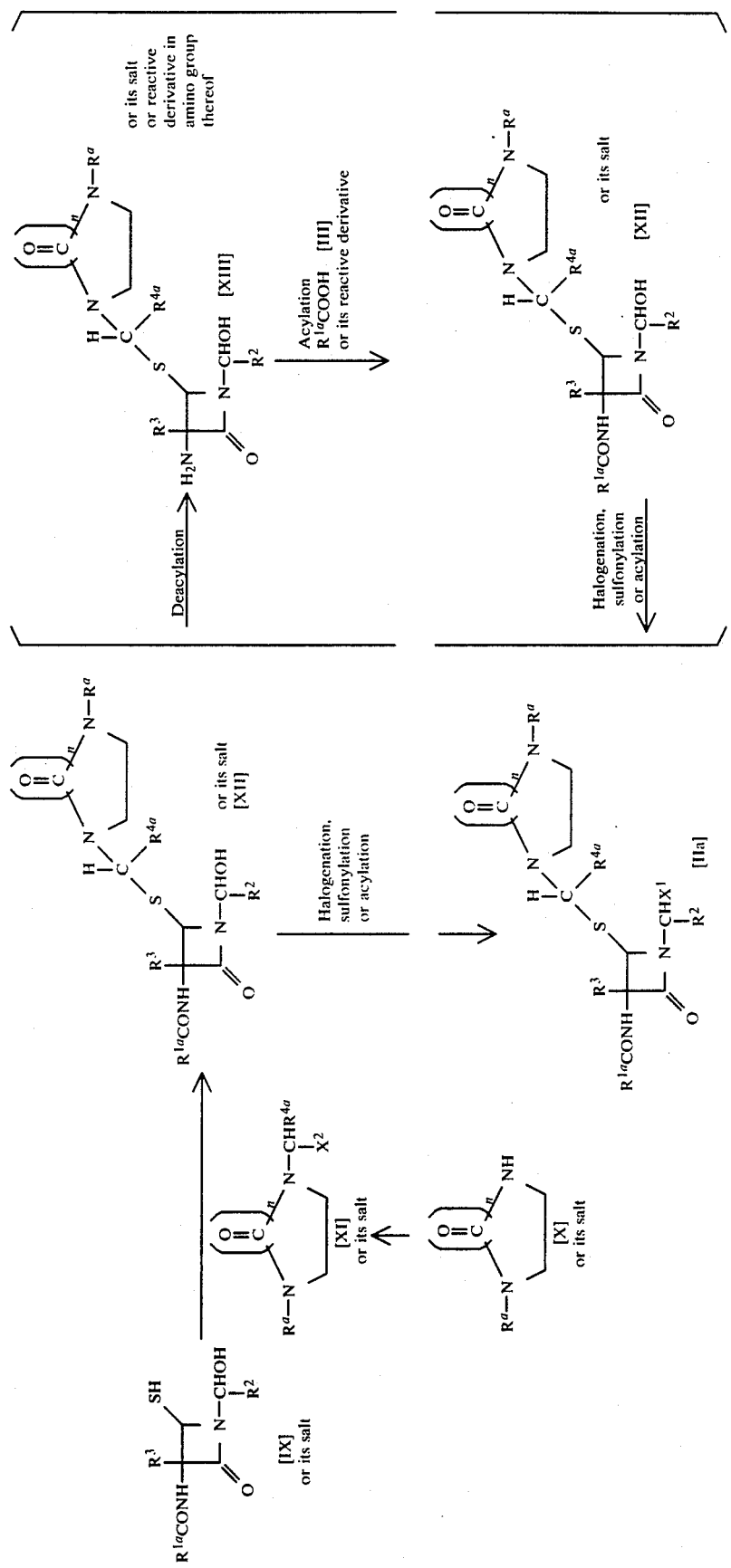

In the above formulas, $R^2$, $R^3$, $R^{1a}CO-$, $R^{4a}$, $X^1$ and n are as defined above; $R^a$ represents an amino group, a group of the formula, $-NHR^5$ or $-NR^56$ in which $R^5$ and $R^6$ are as defined above, or a group of the formula, $-N=CR^7R^8$ in which $R^7$ and $R^8$ are as defined above; $X^2$ means the same removable group as defined as to $X^1$.

The salts of the compounds of general formulas [IX], [X], [XI], [XII] and [XIII] include the same salts as mentioned as to the compound of general formula [I].

The reactive derivatives in the amino group of the compound of general formula [XIII] and its salt include the same reactive derivatives as mentioned as to the compounds of general formulas [Ib] and [IV] and their salts.

Next, a more detailed explanation is made of the above production route for producing the compound of general formula [II].

In the above production route, the reaction with the carboxylic acid of general formula [III] or its reactive derivative and the deacylation can be carried out in the same manners as explained in (2) Deacylation and (3)(i) Acylation above.

The compound of general formula [II] can be produced by reacting a compound of general formula [XII] or its salt with a halogenating agent, a sulfonylating agent or an acylating agent in the presence or absence of a base.

This reaction is preferably conducted under anhydrous conditions, and the solvent to be used may be any solvent as far as it does not adversely affect the reaction. The solvent includes, for example, halogenated hydrocarbons such as methylene chloride, chloroform and the like; ethers such as tetrahydrofuran and the like; nitriles such as acetonitrile and the like; and amides such as N,N-dimethylformamide, N,N-dimethylacetamide and the like. These solvents may be used alone or in admixture of two or more.

The halogenating agent to be used in the reaction includes, for example, thionyl halides such as thionyl chloride, thionyl bromide and the like; the sulfonylating agent to be used in the reaction includes, for example, lower alkanesulfonyl chlorides such as methanesulfonyl chloride and arylsulfonyl chlorides such as p-toluenesulfonyl chloride; and the acylating agent to be used in the reaction includes, for example, acid anhydrides such as acetic anhydride and acid chlorides such as acetyl chloride, benzoyl chloride and the like.

The base which is optionally used in the above reaction includes the same inorganic and organic bases as mentioned in (1) Ring closure.

Each of the amounts of the halogenating agent, sulfonylating agent and acylating agent used and the amount of the base optionally used is 1 to 5 moles, preferably 1.0 to 1.2 moles, per mole of the compound of general formula [XII] or its salt.

The reaction temperature and reaction time are not critical; however, the reaction may be carried out at $-30°$ to $30°$ C., for 5 minutes to 1 hour.

The compounds of general formulas [IX], [XI] and [XII] and their salts can be produced according to the method described in, for example, Japanese Patent Application Kokai (Laid-Open) No. 183,588/1988 or a method similar thereto.

Further, the compound of general formula [IIa] can be converted into a compound of general formula [IIa] in which the group corresponding to $R^a$ is an amino group by subjecting the former to a generally known method such as removal of amino-protecting group, reduction or the like.

In each of the above-mentioned production routes, when the compounds have a hydroxyl group, an amino group or a carboxyl group, it is possible to previously protect these groups with a conventional protective group and to remove, after the reaction, the protective group, if necessary, according to a per se known method.

When the compounds of general formulas [IX], [X], [XI] and [XII] and their salts and the compound of general formula [XIII], its salt and reactive derivatives in the amino group thereof have isomers (for example, optical isomers, geometric isomers, tautomers and the like), all of these isomers may be used. Also, all crystal forms, hydrates and solvates may be used.

The compounds of general formulas [IX], [XI], [XII] and [XIII] thus obtained can be used as they are without being isolated in the subsequent reactions.

When the compound of this invention is used as a drug, it may be mixed appropriately with an excipient which is usually used in preparation, a preparation adjuvant such as pharmaceutically acceptable carrier or the like. The compound can be administered orally or parenterally in the form of a tablet, soft or hard capsule, powder, syrup, granule, fine granule, pill, suspension, emulsion, solution, suppository, ointment or subcutaneous, intramuscular, intravenous or drip infusion.

The administration route, does and number of administrations of the compound of this invention can be appropriately varied depending upon the age, weight and symptom of a patient, and usually, the compound may be administered to an adult patient orally or parenterally (for example, by injection, drip, rectal administration or the like) in an amount of 1 to 250 mg/kg/day in one to several portions.

Next, the antibacterial activities of representative compounds of this invention are explained.

1. Antibacterial activity

Test Method

According to Chemotherapy, vol. 29, No. 1, pp. 76-79 (1981), bacterium was cultured in peptone broth manufactured by Eiken Kagaku K.K. at 37° C. for 20 hours to prepare a bacterial solution of $10^8$ cells/ml, and one loopful of the bacterial solution was inoculated into Heart Infusion agar medium (manufactured by Eiken Kagaku K.K.) containing a drug, cultured at 37° C. for 20 hours, after which growth of bacterium was observed. The minimum concentration at which the growth of bacterium was prevented was indicated as MIC ($\mu$g/ml).

The test compounds used are shown in Table 1 and the results obtained are shown in Table 2.

The symbols used in Table 1 have the following meanings:

Ac: acetyl group, Me: methyl group, Et: ethyl group.

$R^{1a}$ and R in Table 1 refer to those in the following formula for the test compounds:

TABLE 1
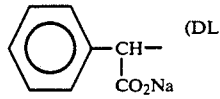
| Compound No. | Substituent R¹ᵃ | R |
|---|---|---|
| 1 | 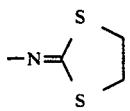 (DL) | 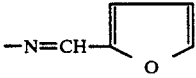 |
| 2 | " | 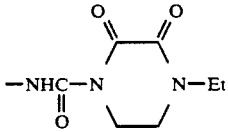 |
| 3 | " | 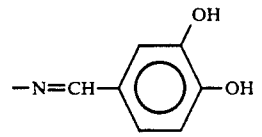 |
| 4 | " | 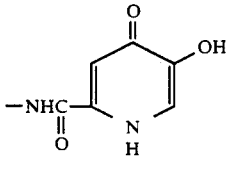 |
| 5 | " | 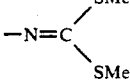 |
| 6 | " |  |
| 7 | " | 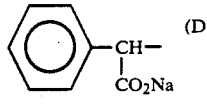 |
| 8 | 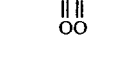 (DL) | 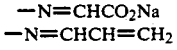 |
| 9 | " | —N=CHCO₂Na |
| 10 | " | —N=CHCH=CH₂ |
| 11 | " | —N=CHCH=CHCO₂Na |
| 12 | " | —N=CHCH=CHCH₂SO₃Na |
| 13 | 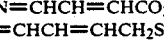 (DL) |  |
| 14 | " | 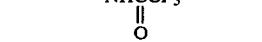 |

TABLE 1-continued

[Structure: R¹ᵃCONH- attached to bicyclic β-lactam with S, N ring, fused to N-R imidazolidinone with =O, and COONa substituent]

| Compound No. | Substituent R¹ᵃ | R |
|---|---|---|
| 15 | " | —NHC(=O)CH$_2$CO$_2$Na |
| 16 | " | —NHSO$_3$Na |
| 17 | " | —NHC(=O)NHMe |
| 18 | " | —N=CHCH=CH$_2$ |
| 19 | " | —N=CHC≡CH |
| 20 | 2-Cl, 4,5-di(AcO)-phenyl-CH(SO$_3$Na)— (DL) | —NHC(=O)NH$_2$ |
| 21 | 2-Cl, 4,5-di(HO)-phenyl-CH(SO$_3$Na)— (DL) | " |
| 22 | 3,4-di(AcO), 5-Cl-phenyl-CH(SO$_3$Na)— (DL) | " |
| 23 | 3,4-di(HO)-phenyl-CH(CO$_2$Na)— (DL) | —N=C(S-CH$_2$CH$_2$-S) (1,3-dithiolan-2-ylidene) |
| 24 | " | —NHC(=O)NH$_2$ |
| 25 | 2-Cl, 4,5-di(HO)-phenyl-CH(CO$_2$Na)— (DL) | " |
| 26 | phenyl-CH(SO$_3$Na)— (DL) | —N=C(S-CH$_2$CH$_2$-S) |

TABLE 1-continued

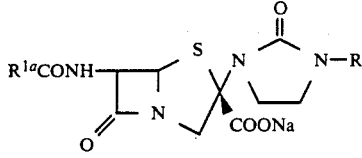

| Compound No. | R¹ᵃ | R |
|---|---|---|
| 27 | AcO-, AcO- phenyl-CH(SO₃Na)- (DL) | " |
| 28 | AcO-, AcO- phenyl-CH(SO₃Na)- (DL) | $-NHCNH_2$ $\parallel$ $O$ |
| 29 | AcO-phenyl-CH(SO₃Na)- (DL) | " |
| 30 | H₂N-phenyl-CH(SO₃Na)- (DL) | " |
| 31 | phenyl-CH(CO₂Na)- (DL) | $-N=CHCH=CHCN$ |
| 32 | " | $-N=CHCNH_2$ $\parallel$ $O$ |
| 33 | " | $-N=CHCH=CHCNH_2$ $\parallel$ $O$ |
| 34 | Cl, AcO-, AcO- phenyl-CH(SO₃Na)- (D) | $-N=CHCH=NNHCNH_2$ $\parallel$ $O$ |
| 35 | Cl, H₂N- phenyl-CH(SO₃Na)- (D) | $-NHCNH_2$ $\parallel$ $O$ |
| 36 | Cl, H₂NCHN(O)- phenyl-CH(SO₃Na)- (D) | " |

TABLE 1-continued
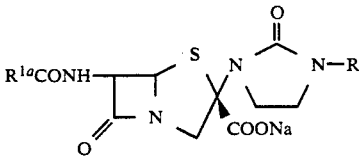
| Compound No. | Substituent R¹ᵃ | R |
|---|---|---|
| 37 | 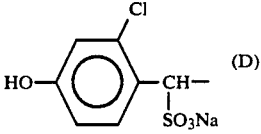 (D) | $-\underset{\underset{O}{\|\|}}{N}HCNH_2$ |
| 38 |  (D) | " |
| 39 | 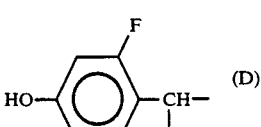 (D) | " |
| 40 | 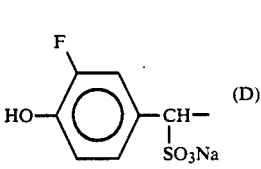 (D) | " |
| 41 | 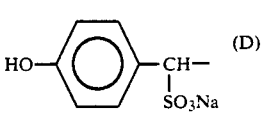 (D) | " |
| 42 | 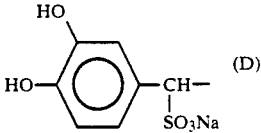 (D) | " |
| 43 | " | $-N=CHCH=NN\underset{\underset{O}{\|\|}}{H}CNH_2$ |
| 44 | 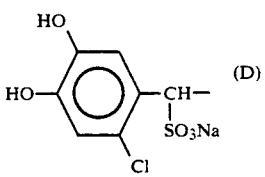 (DL) | $-NHSO_2NH_2$ |
| 45 | 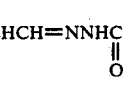 (DL) | $-NHCOCH=CH_2$ |
| 46 | 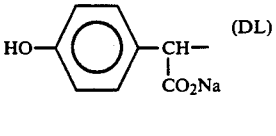 (DL) |  |

TABLE 1-continued

Structure: R$^{1a}$CONH- on β-lactam fused with thiazolidine bearing N-(2-oxoimidazolidin-N-R), COONa substituent

| Compound No. | Substituent R$^{1a}$ | R |
|---|---|---|
| 47 | H$_2$N-C(=N)-S-CH=C(-C(=N-OMe)-) (aminothiazolyl methoxyimino group) | -N=C(S-CH$_2$-CH$_2$-S) (1,3-dithiolan-2-ylidene) |
| 48 | 3,4-dihydroxy-6-chloro-α-(SO$_3$Na)benzyl (DL) | -N=CHCH=CHCO$_2$Na |
| 49 | " | -N=CHCH=CH$_2$ |
| 50 | α-(CO$_2$Na)benzyl (DL) | -N= cyclopentenylidene |
| 51 | Control compound | |

TABLE 2

| Strain | MIC (μg/ml) Compound No. | | | | | |
|---|---|---|---|---|---|---|
| | 1 | 2 | 3 | 4 | 5 | 6 |
| E. coli TK-3* | 0.39 | 0.39 | 0.78 | 6.25 | 3.13 | 3.13 |
| S. marcescens W-8* | 0.1 | 0.39 | 0.78 | 6.25 | 3.13 | 1.56 |
| | 7 | 8 | 9 | 10 | 11 | 12 |
| E. coli TK-3* | 12.5 | 3.13 | 25 | 0.1 | 0.2 | 0.78 |
| S. marcescens W-8* | 6.25 | 1.56 | 12.5 | 0.05 | 0.1 | 0.1 |
| | 13 | 14 | 15 | 16 | 17 | 18 |
| E. coli TK-3* | 12.5 | 3.13 | 12.5 | 12.5 | 1.56 | ≦0.05 |
| S. marcescens W-8* | 3.13 | 3.13 | 12.5 | 12.5 | 1.56 | 0.1 |
| | 19 | 20 | 21 | 22 | 23 | 24 |
| E. coli TK-3* | ≦0.05 | 0.78 | 0.39 | 6.25 | 3.13 | 25 |
| S. marcescens W-8* | ≦0.05 | 0.78 | 0.39 | 12.5 | 3.13 | 12.5 |
| | 25 | 26 | 27 | 28 | 29 | 30 |
| E. coli TK-3* | 6.25 | ≦0.1 | 1.56 | 6.25 | 6.25 | 6.25 |
| S. marcescens W-8* | 12.5 | 0.39 | — | 3.13 | 3.13 | 1.56 |
| | 31 | 32 | 33 | 34 | 35 | 36 |
| E. coli TK-3* | 0.2 | 1.56 | 0.39 | 0.2 | 1.56 | 12.5 |
| S. marcescens W-8* | 0.1 | 0.78 | 0.2 | 0.39 | 0.78 | 1.56 |
| | 37 | 38 | 39 | 40 | 41 | 42 |
| E. coli TK-3* | 0.78 | 1.56 | 3.13 | 3.13 | 3.13 | 0.2 |
| S. marcescens W-8* | 0.2 | 0.78 | 0.78 | 0.78 | 1.56 | 0.39 |
| | 43 | 44 | 45 | 46 | 47 | 48 |
| E. coli TK-3* | 0.2 | 6.25 | 3.13 | 12.5 | 0.78 | 0.1 |
| S. marcescens W-8* | 0.2 | 6.25 | 3.13 | 6.25 | 6.25 | 0.1 |

TABLE 2-continued

| Strain | MIC (μg/ml) Compound No. | | |
|---|---|---|---|
| | 49 | 50 | 51 |
| E. coli TK-3* | ≦0.05 | 0.39 | >200 |
| S. marcescens W-8* | ≦0.05 | 0.1 | >200 |

Note:
*means that β-lactamase-producing bacteria.
Control compound: Sodium salt of (3R,5R,6R)-3-carboxy-6-[D-α-(4-ethyl-2,3-dioxo-1-piperazinecarboxamido)-α-phenylacetamido]-3-(3-methyl-2-oxoimidazolidin-1-yl)-7-oxo-4-thia-1-azabicyclo[3.2.0]heptane (Compound No. 72 in Example 9 of Japanese Patent Application Kokai (Laid-Open) No. 183,588/1988).

As is clear from the above results, the compound of this invention can be utilized as an antibacterial agent.

This invention is described in detail below by way of Reference Examples and Examples. However, this invention is not restricted to these Examples.

In the Examples, there were used, as a carrier in column chromatography, Kieselgel 60, Art. 7734 manufactured by Merck Co.; as a carrier in reversed phase column chromatography, LC-SORB SP-B-ODS manufactured by Chemco Co.; as a carrier in ion exchange column chromatography, Amberlite IR-120B manufactured by Rohm and Haas Co. The mixing ratio in mixed solvent is by volume in all cases.

The symbols used in Reference Examples and Examples have the following meanings.

Me: methyl group, Et: ethyl group, n-Pr: n-propyl group, Ac: acetyl group, Ph: phenyl group, Bzl: benzyl group, PNB: p-nitrobenzyl group, PMB: p-methoxybenzyl group, DPM: diphenylmethyl group The wave number of IR indicates the absorption of carbonyl.

The D and L in each of Reference Example 3 and Examples 5, 13, 24, 26, 35, 36, 39, 40, 41, 42, 43, 44, 45 and 48 are by estimate.

Reference Example 1

The reaction represented by the following production route

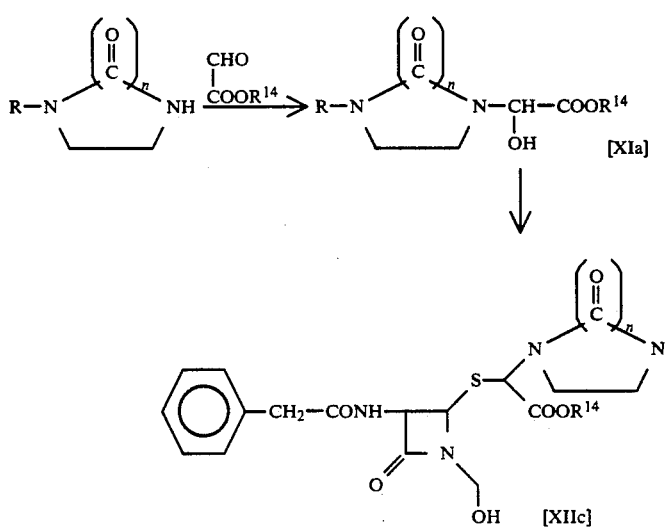

[R and n have the same meanings as given above, and $R^{14}$ represents the same carboxyl-protecting group as described for $R^4$] was conducted in accordance with the method described in Japanese Patent Application Kokai (Laid-Open) No. 183588/1988, to obtain compounds shown in Table 3.

In Table 3, R and $R^{14}$ each show a substituent of the following formula, and n is 1 or 2 as shown in Table 3.

TABLE 3

[XIa]

R—N⟨⟩ₙN—CH—COOR¹⁴
            |
            OH

[XIIc]

Ph—CH₂—CONH— ... S—⟨⟩ₙN—R
                   COOR¹⁴
          N
          |
          OH

| R | R¹⁴ | n | Compound [XIa] IR(KBr) cm⁻¹ | Compound [XIIc] IR(KBr) cm⁻¹ |
|---|---|---|---|---|
| —N=⟨S,S⟩ (dithiolane) | PNB | 1 | 1750, 1710 | 1750, 1700 |
| —N=CH—C₆H₅ | " | " | 1735, 1680 | 1750, 1690 |
| | " | " | 1745, 1695 | 1760, 1750, 1715, 1680 |
| —N=CH—(furyl) | " | " | 1740, 1700 | 1750, 1710, 1670 |
| —N=CH—C₆H₄—Cl | " | " | — | 1760, 1740, 1720, 1660 |
| —N=CHCH₂Cl | " | " | 1750, 1680 | 1760, 1750, 1700 |
| —N=C(SMe)(SMe) | " | " | | |
| —N=⟨S,S⟩ (dithiane) | DPM | 1 | 1755, 1725 | 1760, 1740, 1700, 1670 |
| —N=CH—C₆H₅ | DPM | 1 | 1750, 1705 | 1770, 1740, 1710, 1680 |
| —C₆H₅ | PNB | 2 | 1755, 1680, 1660 | 1750, 1670 |
| —N=CH—(furyl) | DPM | 1 | 1750, 1700 | 1770, 1740, 1705, 1670, 1640 |

TABLE 3-continued

| Structure | | |
|---|---|---|
| $-N=CH-\phantom{xx}\bigcirc\phantom{xx}-OMe$ | " " 1760, 1700 | — |
| $-N=CH-\phantom{xx}\bigcirc\phantom{xx}-Me$ | " " 1745, 1710 | — |

Reference Example 2

15 g of (2-chloro-4,5-diacetoxyphenyl)acetic acid was dissolved in 75 ml of methylene chloride. Thereto was added 9.67 g of a sulfur trioxide-dioxane complex with ice cooling. The mixture was stirred at room temperature for 12 hours. Then, there were added, with ice cooling, 225 ml of ethanol and 18.75 ml of an aqueous solution containing 16.38 g of sodium acetate trihydrate. The mixture was stirred at room temperature for 1 hour. 150 ml of ethanol was added and the mixture was stirred at the same temperature for 3 hours. The resulting mixture was cooled to 5°-10° C. The precipitates were collected by filtration and dried to obtain crude crystals of disodium salt of DL-α-(2-chloro-4,5-diacetoxyphenyl)-α-sulfoacetic acid. Then, the crude crystals were suspended in 155 ml of methanol, and the suspension was stirred at room temperature for 10 minutes. The insolubles were removed by filtration. To the filtrate was added 15.5 ml of an aqueous solution containing 10.24 g of sodium acetate trihydrate, and the mixture was stirred at 30° C. for 8 hours. The resulting crystals were collected by filtration, washed with 16 ml of methanol, and dried under reduced pressure to obtain 11.10 g (yield: 65.0%) of disodium salt of DL-α-(2-chloro 4,5-dihydroxyphenyl)-α-sulfoacetic acid.

IR (KBr) cm$^{-1}$: 1610, 1580

Reference Example 3

(1) 50 g of disodium salt of DL-α-(2-chloro-4,5-dihydroxyphenyl)-α-sulfoacetic acid was dissolved in 400 ml of water. Thereto was added an ion exchange resin (Amberlite IR-120B, H$^+$ type) to adjust the pH to 2.1. The ion exchange resin was removed by filtration and washed twice each with 100 ml of water. The filtrate and the washings were combined. To the resulting solution was added 40.1 g of cinchonidine at 90°-95° C. in 30 minutes. The mixture was stirred at the same temperature for 3 hours and then allowed to stand overnight at room temperature. The resulting crystals were collected by filtration, washed with water and acetone in this order, dried under reduced pressure. The crystals obtained were suspended in 300 ml of ethanol and heated to obtain a solution. Thereto was added 600 ml of hot water of about 60° C., and the mixture was allowed to stand overnight at room temperature. The resulting crystals were collected by filtration, washed with water and acetone in this order, and dried under reduced pressure to obtain 51.2 g (yield 38.8%) of dicinchonidine salt of α-(2-chloro-4,5-dihydroxyphenyl)-α-sulfoacetic acid.

IR (KBr) cm$^{-1}$: 1655, 1590, 1570

(2) 20.0 g of dicinchonidine salt of α-(2-chloro-4,5-dihydroxyphenyl)-α-sulfoacetic acid was dissolved in a mixed solvent consisting of 40 ml of methanol and 40 ml of chloroform. The resulting solution was added to a mixture of 30 ml of an aqueous solution containing 4.60 g of potassium hydrogencarbonate and 40 ml of chloroform. The resulting mixture was stirred for 1.5 hours at room temperature. The aqueous layer was separated, washed twice each with 40 ml of chloroform, and mixed with an ion exchange resin (Amberlite IR-120B, H$^+$ type) to adjust the pH to 2. The ion exchange resin was removed by filtration and washed with 30 ml of water. The filtrate and the washings were combined, and concentrated to about 30 ml under reduced pressure. The residue was subjected to ion exchange column chromatography (H$^+$ type, eluant: water). The eluate was concentrated under reduced pressure. The residue was dissolved in 20 ml of acetonitrile. Thereto was dropwise added 8.48 ml of tri-n-butylamine, and the mixture was stirred for 30 minutes at the same temperature. The resulting crystals were collected by filtration and washed with acetonitrile and diethyl ether, and dried under reduced pressure to obtain 10.2 g (yield: 67.7%) of di-tri-n-butylamine salt of D-α-(2-chloro-4,5-dihydroxyphenyl)-α-sulfoacetic acid.

IR (KBr) cm$^{-1}$: 1605

$[\alpha]_D^{20}$: −3.5° (C=3.0, methanol)

Reference Example 4

4.0 g of disodium salt of DL-α-(2-chloro-4,5-dihydroxyphenyl)-α-sulfoacetic acid was subjected to ion exchange column chromatography (H$^+$ type, eluant: water). The eluate was concentrated under reduced pressure. The residue was dissolved in 20 ml of acetonitrile. Thereto was added dropwise 5.72 ml of tri-n-butylamine with ice cooling. The mixture was stirred at the same temperature for 30 minutes. The resulting crystals were collected by filtration and washed with acetonitrile and diethyl ether, and dried under reduced pressure to obtain 5.0 g (yield: 62.5%) of di-tri-n-butylamine salt of DL-α-(2-chloro-4,5-dihydroxyphenyl)-α-sulfoacetic acid.

IR (KBr) cm$^{-1}$: 1610

EXAMPLE 1

In 420 ml of anhydrous tetrahydrofuran was dissolved 30.00 g of (3R,4R)-4-[1-(3-benzylideneamino-2-oxoimidazolidin-1-yl)-1-(p-nitrobenzyloxycarbonyl)methylthio]-1-hydroxymethyl-3-phenylacetamidoazetidin-2-one. To the solution were added, with ice cooling, 6.72 ml of 2,6-lutidine and 3.95 ml of thionyl chloride in this order. The mixture was stirred at room temperature for 10 minutes. The insolubles were removed by filtration. The solvent was removed by distillation under reduced pressure. The residue was dissolved in 600 ml of anhydrous tetrahydrofuran. To the solution was added 13.6 ml of N,O-bis(trimethylsilyl)acetamide. The mixture was stirred at room temperature for 15 minutes and cooled to −60° C. To the reaction mixture were added, at −40° C. or below, 40.4 ml of hexamethylphosphoric triamide and 69.6 ml of tetrahydrofuran solution containing lithium bis(trimethylsilyl)amide (0.8 mmol/ml), in this order. The temperature of the mixture was elevated to −15° C. in 1 hour. To the reaction mixture was added 3.16 ml of acetic acid while maintaining the temperature at −15° C. The mixture was added to a mixed solvent consisting of 500 ml of water and 500 ml of ethyl acetate. The resulting mixture was adjusted to pH 2.0 with 6N hydrochloric acid. The organic layer was separated, washed with diluted hydrochloric acid of pH 2.0, mixed with 200 ml of water, and adjusted to pH 7.0 with an aqueous sodium hydrogencarbonate solution. The organic layer was separated, washed with water and a saturated aqueous sodium chloride solution in this order, and dried over anhydrous magnesium sulfate. The solvent was removed by distillation under reduced pressure. The residue was purified by column chromatography (eluant: n-hexane/ethyl acetate=1/1 to 2/1) to obtain 13.32 g (yield: 45.7%) of (3R,5R,6R)-3-(3-benzylideneamino-2-oxoimidazolidin-1-yl)-3-(p-nitrobenzyloxycarbonyl)-7-oxo-6-phenylacetamido-4-thia-1-azabicyclo[3.2.0]heptane.

IR (KBr) cm$^{-1}$: 1780, 1720, 1660

The compounds shown in Table 4 were obtained in the same manner.

In Table 4, R and $R^{14}$ each show a substituent of the following formula, and n is 1 or 2 as shown in Table 4.

TABLE 4

[Structure: Ph-CH$_2$-CONH- attached to β-lactam-thiazolidine ring system with COOR$^{14}$ and (CH$_2$)$_n$-N-R with SO$_2$ group]

| R | $R^{14}$ | n | IR(KBr) cm$^{-1}$: |
|---|---|---|---|
| —N=C(S-CH$_2$-CH$_2$-S) (dithiolane) | PNB | 1 | 1780, 1710, 1660 |
| —N=CH—C$_6$H$_4$—Cl | " | " | 1780, 1720, 1660 |
| —N=CH-(furyl) | " | " | 1780, 1720, 1670 |
| —N=CHCH$_2$Cl | " | " | 1780, 1720, 1660 |
| —N=C(SMe)(SMe) | " | " | 1780, 1730, 1705, 1670 |
| —N=C(S-CH$_2$-CH$_2$-S) (dithiolane) | DPM | " | 1780, 1710, 1665 |
| —N=CH—C$_6$H$_5$ | " | " | — |
| —N=CH—C$_6$H$_4$—OMe | DPM | 1 | 1790, 1740, 1730, 1680 |

TABLE 4-continued

[Structure: Ph-CH$_2$-CONH- attached to β-lactam-thiazolidine ring system with COOR$^{14}$ and (CH$_2$)$_n$-N-R with SO$_2$ group]

| R | $R^{14}$ | n | IR(KBr) cm$^{-1}$: |
|---|---|---|---|
| —N=CH—C$_6$H$_4$—Me | " | " | 1790, 1740, 1725, 1680 |
| —N=CH-(furyl) | " | " | 1785, 1735, 1690, 1670 |
| —N=CH—C$_6$H$_5$ | PNB | 2 | 1780, 1740, 1680, 1665 |

EXAMPLE 2

In 132 ml of methylene chloride was dissolved 6.6 g of (3R,5R,6R)-3-(3-benzylideneamino-2-oxoimidazolidin-1-yl)-3-(p-nitrobenzyloxycarbonyl)-7-oxo-6-phenylacetamido-4-thia-1-azabicyclo[3.2.0]heptane.

The solution was cooled to −60° C. Thereto were added 4.66 ml of N,N-dimethylaniline and 3.3 g of phosphorus pentachloride. The mixture was stirred at −40° to −20° C. for 1 hour and cooled to −60° C. To the reaction mixture was added 13.8 ml of anhydrous methanol. The temperature of the mixture was elevated to 0° C. in 30 minutes and mixed with 66 ml of water. The resulting mixture was stirred for 15 minutes with ice cooling. The resulting crystals were collected by filtration and suspended in a mixed solvent consisting of 50 ml of water and 100 ml of methylene chloride. The suspension was adjusted to pH 7.5 with a saturated aqueous sodium hydrogencarbonate solution. The organic layer was separated and dried over anhydrous magnesium sulfate. The solvent was removed by distillation under reduced pressure to obtain 4.5 g (yield: 84.0%) of (3R,5R,6R)-6-amino-3-(3-benzylideneamino-2-oxoimidazolidin-1-yl)-3-(p-nitrobenzyloxycarbonyl)-7-oxo-4-thia-1-azabioyclo[3.2.0]heptane.

IR (KBr) cm$^{-1}$: 1770, 1720

The compounds shown in Table 5 were obtained in the same manner.

In Table 5, R and $R^{14}$ each show a substituent of the following formula.

TABLE 5

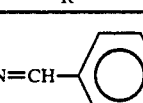

| R | R¹⁴ | IR(KBr) cm⁻¹: |
|---|---|---|
| 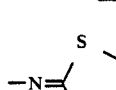 | DPM | 1775, 1725, 1710 |
| 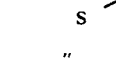 | PNB | 1780, 1740, 1705 |
| " | DPM | 1775, 1730, 1710 |
| —N=CHCH₂Cl | PNB | 1775, 1735, 1710 |

EXAMPLE 3

(1) In a mixed solvent consisting of 200 ml of methylene chloride and 70 ml of methanol was dissolved 13.2 g of (3R,5R,6R)-6-amino-3-(3-benzylideneamino-2-oxoimidazolidin-1-yl)-3-(p-nitrobenzyloxycarbonyl)-7-oxo-4-thia-1-azabicyclo[3.2.0]heptane. Thereto were added 10.3 g of 2,4-dinitrophenylhydrazine and 9.83 g of p-toluenesulfonic acid monohydrate in this order. The mixture was stirred at room temperature for 1.5 hours. The insolubles were removed by filtration. The insolubles were washed with a mixed solvent consisting of 60 ml of methylene chloride and 20 ml of methanol. The washings and the filtrate obtained previously were combined, and mixed with 50 ml of water. The aqueous layer was separated. The organic layer was mixed with 30 ml of water and adjusted to pH 1.2 with 6N hydrochloric acid. The aqueous layer was separated. This aqueous layer and the aqueous layer obtained previously were combined and adjusted to pH 7 with sodium hydrogencarbonate. Thereto was added sodium chloride to saturation. Then, the aqueous layer was extracted with 150 ml of methylene chloride. The aqueous layer was further extracted 7 times each with 50 ml of methylene chloride. The extracts were combined with the organic layer obtained previously, and dried over anhydrous magnesium sulfate. The solvent was removed by distillation under reduced pressure. The residue was purified by column chromatography (eluant: chloroform/methanol=50/1 to 15/1) to obtain 8.93 g (yield: 81.8%) of (3R,5R,6R)-6-amino-3-(3-amino-2-oxoimidazolidin-1-yl)-3-(p-nitrobenzyloxycarbonyl)-7-oxo-4-thia-1-azabicyclo[3.2.0]heptane.

IR (KBr) cm⁻¹: 1775, 1740, 1700

NMR (CDCl₃/D₂O) δ: 3.29(1H, dd, J=1 Hz, J=13 Hz), 3.53(4H, s), 4.54(1H, dd, J=1 Hz, J=4 Hz), 4.88(1H, d, J=13 Hz), 5.30(2H, s), 5.45(1H, d, J=4 Hz), 7.56(2H, d, J=9 Hz), 8.24(2H, d, J=9 Hz).

In the same manner was obtained (3R,5R,6R)-6-amino-3-(3-amino-2-oxoimidazolidin-1-yl)-3-diphenylmethyloxycarbonyl-7-oxo-4-thia-1-azabicyclo[3.2.0]heptane.

IR (KBr) cm⁻¹: 1775, 1720, 1700

(2) In a mixed solvent consisting of 30 ml of water and 30 ml of methanol was suspended 5.00 g of (3R,5R,6R)-6-amino-3-(3-amino-2-oxoimidazolidin-1-yl)-3-(p-nitrobenzyloxycarbonyl)-7-oxo-4-thia-1-azabicyclo[3.2.0]heptane. To suspension was added 2.96 ml of concentrated hydrochloric acid with water cooling. To the resulting solution was added 1.36 g of sodium cyanate in 10 minutes, and the mixture was stirred at room temperature for 30 minutes. The reaction mixture was filtered. To the filtrate were added 50 ml of ethyl acetate and 50 ml of water. The aqueous layer was separated. The organic layer was extracted three times each with 30 ml of water. The extracts were combined with the aqueous layer obtained previously. The combined aqueous solution was adjusted to pH 6.9 with sodium hydrogencarbonate. The solvent was removed by distillation under reduced pressure. The residue was dehydrated by four times of azeotropy with ethanol. To the resulting residue was added a mixed solvent consisting of 50 ml of methylene chloride and 10 ml of methanol. The insolubles were removed by filtration. The filtrate was concentrated under reduced pressure. The residue was purified by column chromatography (eluant: chloroform/methanol=10/1 to 5/1) to obtain 4.29 g (yield: 77.9%) of (3R,5R,6R)-6-amino-3-(p-nitrobenzyloxycarbonyl)-7-oxo-3-(2-oxo-3-ureidoimidazolidin-1-yl)-4-thia-1-azabicyclo[3.2.0]heptane.

IR (KBr) cm⁻¹: 1775, 1720, 1680

NMR (d₆-DMSO/D₂O) δ: 3.15–3.80(5H, m), 4.57(1H, d, J=4 Hz), 4.59(1H, d, J=13 Hz), 5.27(2H, s), 5.48(1H, d, J=4 Hz), 7.65(2H, d, J=9 Hz), 8.23(2H, d, J=9 Hz).

In the same manner was obtained (3R,5R,6R)-6-amino-3-diphenylmethyloxycarbonyl-7-oxo-3-(2-oxo-3-uriedoimidazolidin-1-yl)-4-thia-1-azabicyclo[3.2.0]heptane.

IR (KBr) cm⁻¹: 1780, 1720, 1680

In the same manner in hydrous tetrahydrofuran, there was obtained (3R,5R,6R)-6-methoxy-3-(p-nitrobenzyloxycarbonyl)-6-[DL-α-(p-nitrobenzyloxycarbonyl)-α-phenylacetamido]-7-oxo-3-(2-oxo-3-ureidoimidazolidin-1-yl)-4-thia-1-azabicyclo[3.2.0]heptane.

IR (KBr) cm⁻¹: 1775, 1720, 1680

EXAMPLE 4

(1) In 8 ml of methylene chloride was dissolved 300 mg of (3R,5R,6R)-3-{3-(2-furfurylideneamino)-2-oxoimidazolidin-1-yl}-3-(p-nitrobenzyloxycarbonyl)-7-oxo-6-phenylacetamido-4-thia-1-azabicyclo[3.2.0]heptane. The solution was cooled to −50° C. Thereto were added 0.18 ml of N,N-dimethylaniline and 141 mg of phosphorus pentachloride in this order. The mixture was stirred at −40° to −20° C. for 1 hour and cooled to −60° C. To the reaction mixture was added 1.4 ml of anhydrous methanol, and the resulting mixture was stirred at −10° to 0° C. for 30 minutes. 5 ml of water was added to the reaction mixture. The resulting mixture was stirred for 10 minutes with ice cooling and adjusted to pH 7.5 with a saturated aqueous sodium hydrogencarbonate solution. The organic layer was separated, washed with water and a saturated aqueous sodium chloride solution in this order, and dried over anhydrous magnesium sulfate to obtain a methylene chloride solution of (3R,5R,6R)-6-amino-3-{3-(2-furfurylideneamido)-2-oxoimidazolidin-1-yl}-3-(p-nitrobenzyloxycarbonyl)-7-oxo-4-thia-1-azabicyclo[3.2.0]heptane.

(2) In 13 ml of methylene chloride was dissolved 190 mg of D-α-(4-ethyl-2,3-dioxo-1-piperazinecarboxamido)phenylacetic acid. To the solution were added, with ice cooling, a catalytic amount of N,N-dimethylformamide and 0.05 ml of oxalyl chloride. The mixture was stirred at room temperature for 30 minutes. The reaction mixture was subjected to evaporation to dryness under reduced pressure to obtain D-α-(4-ethyl-2,3-dioxo-1-piperazinecarboxamido)phenylacetyl chloride. The compound was dissolved in 3 ml of methylene chloride. The solution was dropwise added to the solution prepared in (1) above, at −30° to −20° C. The mixture was stirred for 15 minutes at the same temperature and further for 20 minutes with ice cooling. The reaction mixture was washed with water and a saturated aqueous sodium chloride solution in this order and dried over anhydrous magnesium sulfate. The solvent was removed by distillation under reduced pressure. The residue was purified by column chromatography (eluant: chloroform/acetone=9/1 to 4/1) to obtain 260 mg (yield: 66.8%) of (3R,5R,6R)-6-[D-α-(4-ethyl-2,3-dioxo-1-pierazinecarboxamido)-α-phenylacetamido[-3-[3-(2-furfurylideneamino)-2-oxoimidazolidin-1-yl]-3-(p-nitrobenzyloxycarbonyl)-7-oxo-4-thia-1-azabicyclo[3.2.0]heptane.

IR (KBr) cm$^{-1}$: 1780, 1710, 1680

NMR (CDCl$_3$) δ: 1.25(3H, t, J=7 Hz), 3.28(1H, d, J=13 Hz), 3.30-4.30(10H, m), 4.57(1H, d, J=13 Hz), 5.20-5.80(5H, m), 6.49(1H, dd, J=2 Hz, J=3.5 Hz), 6.73(1H, d, J=3.5 Hz), 7.20-7.65(9H, m), 7.97(1H, d, J=9.5 Hz), 8.18(2H, d, J=9 Hz), 9.95(1H, d, J=6 Hz).

The compounds shown in Table 6 were obtained in the same manner by effecting acylation using N,N′-dicyclohexylcarbodiimide as a condensing agent, a mixed anhydride, an acid chloride or the like.

In Table 6, R$^{1a}$, R$^{14}$ and R each show a substituent of the following formula, and n is 1 or 2 as shown in Table 6.

TABLE 6

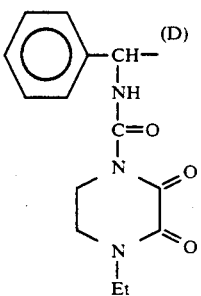

| R$^{1a}$ | R | R$^{14}$ | n | IR(KBr) cm$^{-1}$: |
|---|---|---|---|---|
| 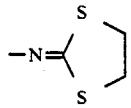 | 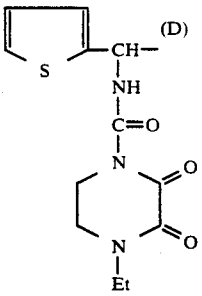 | PNB | 1 | 1780, 1720, 1680 |
| 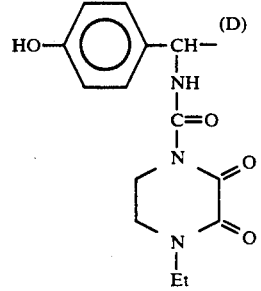 | " | " | " | 1780, 1710, 1680 |
|  | " | " | " | 1780, 1710, 1670 |

TABLE 6-continued

[Structure: R¹ᵃCONH-[β-lactam-thiazolidine]-COOR¹⁴ with N-(C=O)ₙ-N-R ring substituent]

| R¹ᵃ | R | R¹⁴ | n | IR(KBr) cm⁻¹: |
|---|---|---|---|---|
| 3,4-diacetoxyphenyl-CH(DL)(NH-C(=O)-[2,3-dioxopiperazin-1-yl,4-Et]) | -N=C(S-CH₂-CH₂-S) (1,3-dithiolan-2-ylidene) | PNB | 1 | 1770, 1710, 1680 |
| 2-chloro-4,5-diacetoxyphenyl-CH(DL)(NH-C(=O)-[2,3-dioxopiperazin-1-yl,4-Et]) | " | " | " | 1775, 1720, 1705, 1680 |
| phenyl-CH(D)(NH-CO₂PNB) | " | " | " | 1780, 1720, 1680 |
| phenyl-CH(D)(NH-C(=O)-[2,3-dioxopiperazin-1-yl,4-Ph]) | " | " | " | 1780, 1720, 1680 |
| 4-hydroxyphenyl-CH(D)(NH-CO₂PNB) | -N=C(S-CH₂-CH₂-S) | PNB | 1 | 1780, 1705, 1680 |

TABLE 6-continued
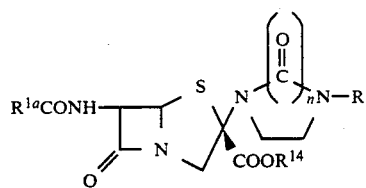
| $R^{1a}$ | R | $R^{14}$ | n | IR(KBr) cm$^{-1}$: |
|---|---|---|---|---|
| MeS–CH– NH C=O (DL) piperazine-2,3-dione-N-Et | " | " | " | 1780, 1730, 1710, 1670 |
| Ph–CH–CO$_2$PNB (DL) | " | " | " | 1780, 1740, 1720, 1670 |
| Ph–CH–O–CHO (D) | " | " | " | 1780, 1710, 1680 |
| thienyl–CH–CO$_2$PNB (DL) | " | " | " | 1780, 1720, 1700, 1670 |
| aminothiazolyl C=N–OMe | " | " | " | 1780, 1720, 1700, 1660 |
| aminothiazolyl C=N–OCH$_2$CH$_2$F | " | " | " | 1780, 1730, 1710, 1660 |
| aminothiazolyl C=N–OCH$_2$CO$_2$DPM | –N=thiazolidinyl (S,S) | PNB | 1 | 1780, 1740~1700, 1680 |

TABLE 6-continued
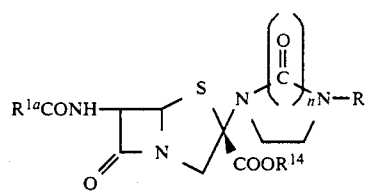
| $R^{1a}$ | R | $R^{14}$ | n | IR(KBr) cm$^{-1}$: |
|---|---|---|---|---|
| (D) HO-C6H4-CH(NH-C(=O)-pyridinone-N-OH, OBzl)- | " | " | " | 1780, 1720, 1700, 1675 |
| H2N-C(=N)-S-CH=C(-C(=N-OMe)-)- | -N=CH-C6H5 | " | " | 1780, 1720, 1670 |
| (DL) C6H5-CH(CO2PNB)- | " | " | " | 1780, 1730, 1720, 1670 |
| (D) C6H5-CH(NH-C(=O)-N(piperazine-2,3-dione)-Et)- | " | " | " | 1780, 1720, 1670 |
| (D) HO-C6H4-CH(NH-C(=O)-N(piperazine-2,3-dione)-Et)- | -N=CH-C6H5 | PNB | 1 | 1780, 1710, 1670 |
| (DL) C6H5-CH(CO2PNB)- | -N=CH-furyl | " | " | 1780, 1720, 1670 |

TABLE 6-continued

[Structure: R¹ᵃCONH-β-lactam-S-thiazolidine with COOR¹⁴ and N-(C=O)ₙ-N-R substituent]

| R¹ᵃ | R | R¹⁴ | n | IR(KBr) cm⁻¹: |
|---|---|---|---|---|
| Ph-CH(NH-CO₂PNB)- (D) | " | " | " | 1780, 1715, 1680 |
| Benzothiophene-CH(NH-C(=O)-N(piperazine-2,3-dione)-N-Et)- (DL) | " | " | " | 1780, 1730, 1705, 1670 |
| Naphthyl-CH(NH-C(=O)-N(piperazine-2,3-dione)-N-Et)- (DL) | " | " | " | 1780, 1730, 1710, 1680 |
| Ph-CH(NH-C(=O)-N(piperazine-2,3-dione)-N-Et)- (D) | -N=CH-C₆H₄-Cl | PNB | 1 | 1780, 1710, 1765 |
| " | -N=C(SMe)₂ | " | " | 1780, 1710, 1680 |
| Ph-CH(CO₂PNB)- (DL) | " | " | " | 1780, 1730, 1710, 1675 |

TABLE 6-continued

Structure: R¹ᵃCONH— [β-lactam with S, fused to N-ring with COOR¹⁴ and (C=O)ₙ—N—R substituent]

| R¹ᵃ | R | R¹⁴ | n | IR(KBr) cm⁻¹ |
|---|---|---|---|---|
| Ph-CH(D)(NH-C(=O)-piperazine-2,3-dione-N-Et) | —N=CH—Ph | DPM | " | 1680, 1710, 1680 |
| 2-Cl-4,5-(AcO)₂-C₆H₂-CH(DL)(NH-C(=O)-piperazine-2,3-dione-N-Et) | " | PNB | " | 1780, 1720, 1680 |
| 3,4-(AcO)₂-C₆H₃-CH(DL)(NH-C(=O)-piperazine-2,3-dione-N-Et) | —N=CH—Ph | PNB | 1 | 1780, 1720, 1680 |
| 2-aminothiazol-4-yl-CH(DL)(NH-CO₂PNB) | —N=C(S-CH₂CH₂-S) (1,3-dithiolan-2-ylidene) | " | " | 1780, 1720, 1675 |
| thien-2-yl-CH(DL)(CO₂PNB) | —N=CH—Ph | " | " | 1785, 1720, 1675 |
| 4-F-C₆H₄-CH(DL)(CO₂PMB) | " | " | " | 1790, 1725, 1675, 1625 |

TABLE 6-continued

[Structure: R¹ᵃCONH-β-lactam-S-CH₂-C(COOR¹⁴)-N-(C=O)ₙ-N-R]

| R¹ᵃ | R | R¹⁴ | n | IR(KBr) cm⁻¹: |
|---|---|---|---|---|
| 2-Cl-C₆H₄-CH(CO₂PMB)- (DL) | " | " | " | 1785, 1720, 1680, 1625 |
| 4-(H₂NCO-O)-C₆H₄-CH(CO₂PMB)- (DL) | " | " | " | 1785, 1725, 1680 |
| 2-(H₂N)-thiazol-4-yl-C(=N-O-C(Me)₂-CO₂DPM)- | -N=CH-C₆H₅ | PNB | 1 | 1785, 1725, 1680 |
| C₆H₅-CH(NH-CO₂PNB)- (D) | " | " | " | 1780, 1720, 1680 |
| 2-(H₂N)-thiazol-4-yl-C(=N-O-CH(3,4-diAcO-C₆H₃)(CO₂DPM))- | -N=C(S-CH₂-CH₂-S) | " | " | 1770, 1740, 1720, 1680 |
| 2-(H₂N)-thiazol-4-yl-C(=N-O-C(Me)₂-CO₂DPM)- | " | " | " | 1780, 1710, 1670 |
| C₆H₅-CH(CO₂PNB)- (DL) | -N=CH-C₆H₅ | DPM | " | — |

TABLE 6-continued

| $R^{1a}$ | R | $R^{14}$ | n | IR(KBr) cm$^{-1}$: |
|---|---|---|---|---|
| AcO-C6H4-CH(NH-C(=O)-piperazine-2,3-dione-N-Et)- (D) | -N=CH-C6H5 | PNB | 1 | — |
| C6H5-CH(NH-C(=O)-piperazine-2,3-dione-N-Et)- (D) | " | " | 2 | 1785, 1740, 1710, 1675 |
| (aminothiazolyl)-CH=CH-CH(NH-C(=O)-piperazine-2,3-dione-N-Et)- (DL) | -N=CHCH$_2$Cl | " | 1 | 1780, 1710, 1680 |

EXAMPLE 5

DL-α-(p-methoxybenzyloxycarbonyl)-α-[4-(p-methoxybenzyloxy)phenyl]acetic acid and (3R,5R,6R)-6-amino-3-[3-(1,3-dithiolan-2-ylideneamino)-2-oxoimidazolidin-1-yl]-3-(p-nitrobenzyloxycarbonyl)-7-oxo-4-thia-1-azabicyclo[3.2.0]heptane were subjected to condensation reaction using N-hydroxysuccinimide and N,N'-dicyclohexylcarbodiimide to obtain (3R,5R,6R)--3-[3-(1,3-dithiolan-2-ylideneamino)-2-oxoimidazolidin-1-yl]-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane.

IR (KBr) cm$^{-1}$: 1785, 1720, 1670

The compounds shown in Table 7 were obtained in the same manner.

In Table 7, $R^{1a}$, $R^{14}$ and R each show a substituent of the following formula.

TABLE 7
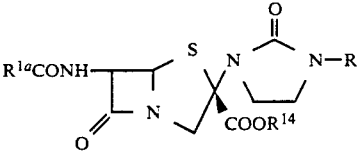
| R¹ᵃ | R | R¹⁴ | IR(KBr) cm⁻¹: |
|---|---|---|---|
| 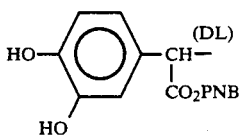 | 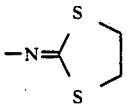 | PNB | 1780, 1730, 1680 |
| 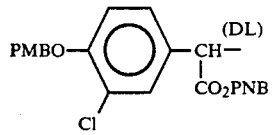 | —NHCNH₂ ‖ O | " | 1785, 1725, 1680 |
|  | " | " | 1780, 1730, 1680 |
| 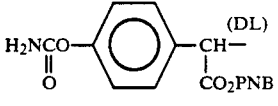 | " | " | 1780, 1725, 1680 |
| 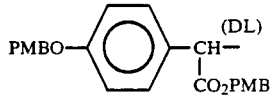 | " | " | 1775, 1725, 1670 |
| 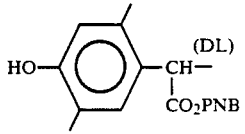 | " | " | 1780, 1720, 1680 |
| 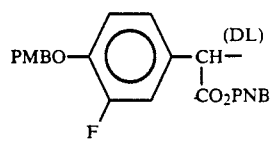 | —NHCNH₂ ‖ O | PNB | 1780, 1725, 1675 |
| 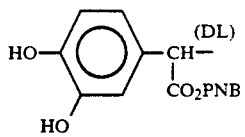 | " | " | 1780, 1720, 1680 |
|  | " | " | 1790, 1720, 1705 |
| 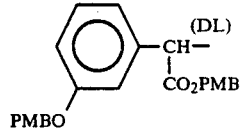 | 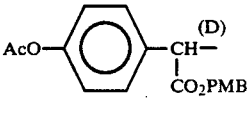 | DPM | 1785, 1720, 1670 |

TABLE 7-continued

[Structure: R¹ᵃCONH-[β-lactam with S, spiro imidazolidinone N-R, COOR¹⁴]]

| R¹ᵃ | R | R¹⁴ | IR(KBr) cm⁻¹: |
|---|---|---|---|
| HO-⟨phenyl⟩-CH(CO₂PMB)- (DL) | " | " | 1780, 1720, 1675 |
| PMBO-⟨phenyl⟩-CH(CO₂PMB)- (DL) | " | PNB | 1770, 1725, 1710, 1675 |
| " | " | DPM | 1780, 1720, 1680 |
| HO-⟨phenyl⟩-CH(CO₂PNB)- (DL) | " | " | — |

EXAMPLE 6

In a mixed solvent consisting of 30 ml of methylene chloride and 15 ml of methanol was dissolved 3.00 g of (3R,5R,6R)-3-(3-benzylideneamino-2-oxoimidazolidin-1-yl)-3-(p-nitrobenzyloxycarbonyl)-7-oxo-6-phenylacetamido-4-thia-1-azabicyclo[3.2.0]heptane. To the solution were added 1.89 g of 2,4-dinitrophenylhydrazine and 850 mg of p-toluenesulfonic acid monohydrate in this order. The mixture was stirred at room temperature for 1.5 hours. Then, the insolubles were removed by filtration. The filtrate was concentrated under reduced pressure. The residue was mixed with a mixed solvent consisting of 30 ml of methylene chloride and 7 ml of methanol. The insolubles were removed by filtration. The filtrate was concentrated under reduced pressure. The residue was purified by column chromatography (eluant: chloroform/methanol=100/1 to 25/1) to obtain 1.56 g (yield: 60.5%) of (3R,5R,6R)-3-(3-amino-2-oxoimidazolidin-1-yl)-3-(p-nitrobenzyloxycarbonyl)-7-oxo-6-phenylacetamido-4-thia-1-azabicyclo[3.2.0]heptane.

IR (KBr) cm⁻¹: 1780, 1720, 1700, 1670

NMR (CDCl₃) δ: 3.30(1H, d, J=13 Hz), 3.48(4H, s), 3.59(2H, s), 4.69(1H, d, J=13 Hz), 5.14(2H, s), 5.47(1H, d, J=4 Hz), 5.66(1H, dd, J=4 Hz, J=8 Hz), 6.66(1H, d, J=8 Hz), 7.29(5H, s), 7.49(2H, d, J=9 Hz), 8.23(2H, d, J=9 Hz).

The compounds shown in Table 8 were obtained in the same manner.

In Table 8, R¹ᵃ and R¹⁴ each show a substituent of the following formula, and n is 1 or 2 as shown in Table 8.

TABLE 8

[Structure: R¹ᵃCONH-[β-lactam with S, spiro ring with (C=O)ₙ-N-NH₂, COOR¹⁴]]

| R¹ᵃ | R¹⁴ | n | IR(KBr) cm⁻¹: |
|---|---|---|---|
| ⟨phenyl⟩-CH(NH-C(=O)-N[piperazine-2,3-dione-N-Et])- (D) | " | 1 | 1780, 1710, 1680 |
| HO-⟨phenyl⟩-CH(NH-C(=O)-N[piperazine-2,3-dione-N-Et])- (D) | " | " | 1780, 1710, 1670 |

TABLE 8-continued

Structure: R¹ᵃCONH—[β-lactam-thiazolidine]—N—C(=O)—N(cyclic, n)—N—NH₂, with COOR¹⁴

| R¹ᵃ | R¹⁴ | n | IR(KBr) cm⁻¹ |
|---|---|---|---|
| thiazole-C(=NOMe)- with H₂N-C(S)- (aminothiazolyl methoxyimino) | " | " | 1775, 1720, 1690, 1665 |
| Ph-CH(CO₂PNB)- (DL) | PNB | 1 | 1780, 1730, 1700, 1680 |
| 2-Cl, 4,5-di-AcO-C₆H₂-CH(Me)-NH-C(=O)- (D) attached to N-ethyl dioxopiperazine | PNB | 1 | 1775, 1710, 1680 |
| 4-PMBO-C₆H₄-CH(CO₂PMB)- (DL) | " | " | 1780, 1720, 1670, 1650 |
| Ph-CH(Me)-NH-C(=O)- N-ethyl dioxopiperazine (D) | DPM | " | 1785, 1715, 1680 |
| aminothiazolyl-C(=N-O-C(Me)₂-CO₂DPM)- | PNB | " | 1780, 1730, 1680 |
| Ph-CH(CO₂PNB)- (DL) | DPM | 1 | 1785, 1725, 1680 |

| R¹ᵃ | R¹⁴ | n | IR(KBr) cm⁻¹ |
|---|---|---|---|
| Ph-CH(CO₂DPM)- (DL) | " | " | 1780, 1720, 1680 |
| 4-HO-C₆H₄-CH(CO₂PMB)- (DL) | " | " | 1780, 1720, 1680 |
| 4-HO-C₆H₄-CH(CO₂PNB)- (DL) | " | " | 1780, 1725, 1680, 1660 |
| Ph-CH(Me)-NH-C(=O)- N-ethyl dioxopiperazine (D) | PNB | 2 | 1780, 1740, 1710, 1670 |
| 3,4-di-AcO-C₆H₃-CH(Me)-NH-C(=O)- N-ethyl dioxopiperazine (DL) | " | 1 | — |
| 4-AcO-C₆H₄-CH(Me)-NH-C(=O)- N-ethyl dioxopiperazine (D) | PNB | 1 | — |
| 2-thienyl-CH(CO₂PNB)- (DL) | " | " | 1785, 1735, 1680 |

TABLE 8-continued

Structure:
R^{1a}CONH—[β-lactam with S]—[spiro carbon with COOR^{14}]—N—C(=O)—(CH_2)_n—N—NH_2

| R^{1a} | R^{14} | n | IR(KBr) cm$^{-1}$ |
|---|---|---|---|
| F—C_6H_4—CH(CO_2PMB)— (DL) | " | " | 1785, 1720, 1680 |
| Cl—C_6H_4—CH(CO_2PMB)— (DL) | " | " | 1785, 1720, 1680 |
| H_2NCO—C_6H_4—CH(CO_2PMB)— (DL) | " | " | 1780, 1730, 1675 |
| PMB—O— | DPM | " | 1785, 1720 |
| PMB—O—C_6H_4—CH(CO_2PMB)— (DL) | " | " | 1785, 1725 |

EXAMPLE 7

In the same manner as in Example 6, there was obtained (3R,5R,6R)-3-(3-amino-2-oxoimidazolidin-1-yl)-6-methoxy-3-(p-nitrobenzyloxycarbonyl)-6-[DL-α-(p-nitrobenzyloxycarbonyl)-α-phenylacetamido]-7-oxo-4-thia-1azabicyclo[3.2.0]heptane.

IR (KBr) cm$^{-1}$: 1780, 1740, 1680

EXAMPLE 8

In a mixed solvent consisting of 5 ml of methylene chloride and 5 ml of methanol was dissolved 500 mg of (3R,5R,6R)-3-(3-amino-2-oxoimidazolidin-1-yl)-6-[D-α-(4-ethyl-2,3-dioxo-1-piperazinecarboxamido)-α-phenylacetamido]-3-(p-nitrobenzyloxycarbonyl)-7-oxo-4-thia-1-azabicyclo[3.2.0]heptane. To the solution were added 100 mg of 5-formyl-1,2,3-thiadiazole and a catalytic amount of p-toluenesulfonic acid monohydrate. The mixture was stirred overnight at room temperature. The solvent was removed by distillation under reduced pressure. The residue was purified by column chromatography (eluant: chloroform/acetone=10/1 to 4/1) to obtain 400 mg (yield: 70.7%) of (3R,5R,6R)-6-[D-α-(-4-ethyl-2,3-dioxo-1-piperazinecarboxamido)-α-phenylacetamido]-3-(p-nitrobenzyloxycarbonyl)-7-oxo-3-[2-oxo-3-(1,2,3-thiadiazol-5-ylmethylideneamino)imidazolidin-1-yl]-4-thia-1azabicyclo[3.2.0]heptane.

IR (KBr) cm$^{-1}$: 1780, 1710, 1670

NMR (CDCl_3) δ: 1.25(3H, t, J=7 Hz), 3.32(1H, d, J=13 Hz), 3.20–4.30(10H, m), 4.63(1H, d, J=13 Hz), 5.26(2H, s), 5.20–5.80(3H, m), 7.37(5H, s), 7.52(2H, d, J=9 Hz), 7.78(1H, d, J=9 Hz), 7.94(1H, s), 8.16(2H, d, J=9 Hz), 8.79(1H, s), 9.95(1H, d, J=6 Hz).

The compounds shown in Table 9 were obtained in the same manner.

In Table 9, R$^{1a}$, R$^{14}$ and R each show a substituent of the following formula, and n is 1 or 2 as shown in Table 9.

TABLE 9

Structure:
R^{1a}CONH—[β-lactam with S]—[spiro center COOR^{14}]—N—C(=O)—N—R

| R^{1a} | R | R^{14} | n | IR(KBr) cm$^{-1}$ |
|---|---|---|---|---|
| C_6H_5—CH(NH—C(=O)—N(piperazine-2,3-dione-N'-Et))— (D) | —N=CH—(pyridyl) | PNB | 1 | 1780, 1710, 1680 |
| " | —N=CH—(pyridyl-N) | " | " | 1780, 1710, 1680 |

TABLE 9-continued

[Structure: R¹ᵃCONH-[β-lactam fused with S-containing ring]-COOR¹⁴, with N-(C=O)ₙ-N-R side chain]

| R¹ᵃ | R | R¹⁴ | n | IR(KBr) cm⁻¹: |
|---|---|---|---|---|
| " | —N=CH—Ac | " | " | 1780, 1715, 1680 |
| " | —N=CH—C₆H₄—OH (para) | " | " | 1780, 1720, 1680 |
| " | —N=CH—C₆H₃(OH)₂ (3,4-dihydroxy) | " | " | 1780, 1720, 1680 |
| " | —N=CH—(pyrazinyl) | " | " | 1780, 1720, 1670 |
| Ph-CH(D)(NH-C(=O)-N-piperazine-2,3-dione-N'-Et) | —N=CH—C₆H₄—N(Me)₂ (para) | PNB | 1 | 1785, 1715, 1680 |
| " | —N=CHCO₂PNB | " | " | 1780, 1760, 1720, 1680 |
| " | —N=CH—C₆H₄—NO₂ (para) | " | " | 1785, 1720, 1680 |
| " | —N=CH—(1H-pyrazol-3-yl) | " | " | 1785, 1720, 1680 |
| " | —N=CH—C₆H₄—NO₂ (para) | DPM | " | 1785, 1715, 1680 |
| " | *—N=CH—CH=CH—(furan-2-yl) | " | " | 1780, 1720, 1680 |
| " | *—N=CH—CH=CH—(pyridin-4-yl) | " | " | 1780, 1720, 1680 |

TABLE 9-continued

Structure:
$R^{1a}CONH$ — β-lactam-thiazolidine fused ring with $COOR^{14}$ and $(CO)_n$—N—R piperazinone substituent

| $R^{1a}$ | R | $R^{14}$ | n | IR(KBr) cm$^{-1}$: |
|---|---|---|---|---|
| Ph-CH(D)(NH-C(=O)-piperazine-2,3-dione-N-Et) | $-N=CHC\equiv C-Ph$ | DPM | 1 | 1785, 1720, 1680 |
| " | $-N=CHCH=CH_2$ | " | " | 1780, 1720, 1680 |
| " | $-N=CHC\equiv CH$ | " | " | 1785, 1720, 1680 |
| " | $-N=CH-(2-hydroxyphenyl)$ | " | " | 1785, 1720, 1685 |
| " | $-N=CH-CH=CH-Ph$ | " | " | 1780, 1720, 1680 |
| " | $-N=CHN(azepane)$ | PNB | " | 1780, 1710, 1680 |
| " | $-N=CH-(pyrazinyl)$ | " | " | 1780, 1715, 1680 |
| Ph-CH(D)(NH-C(=O)-piperazine-2,3-dione-N-Et) | $-N=CHC\equiv CH$ | PNB | 1 | 1780, 1715, 1680 |
| " | $-N=CHCH_2Cl$ | " | " | 1780, 1715, 1680 |

TABLE 9-continued

[Structure: R¹ᵃCONH-[β-lactam fused with S-containing ring]-N-[ring with (C=O)ₙ and N-R, COOR¹⁴]]

| R¹ᵃ | R | R¹⁴ | n | IR(KBr) cm⁻¹: |
|---|---|---|---|---|
| " | −N=CH−C₆H₅ | " | 2 | 1785, 1740, 1710, 1675 |
| C₆H₅−CH(CO₂PNB)− (DL) | −N=CH−(3-OBzl-4-oxo-1,4-dihydropyridin-6-yl) | " | 1 | 1780, 1730, 1680 |
| " | −N=CH−(3,4-dihydroxyphenyl) | " | " | 1780, 1730, 1710, 1680 |
| " | *−N=CHCH=CHCH₂SO₃H | " | " | 1780, 1720, 1670 |
| " | −N=CHCO₂DPM | DPM | " | 1785, 1740, 1720, 1680 |
| C₆H₅−CH(CO₂PNB)− (DL) | −N=(barbituric acid-5-ylidene) | PNB | 1 | 1680, 1740, 1715, 1680 |
| C₆H₅−CH(CO₂DPM)− (DL) | −N=CHCH=CH₂ | DPM | " | 1780, 1720, 1670 |
| " | *−N=CHCH=CHCO₂H | " | " | 1790, 1710, 1650 |
| HO−C₆H₄−CH(CO₂PMB)− (DL) | −N=CHCH=CH₂ | " | " | 1785, 1720, 1680 |
| " | −N=CHC≡CH | " | " | 1785, 1725, 1675 |
| 8c H₂N−(thiazol-4-yl)−C(=N−OMe)− | −N=CH−(pyridin-4-yl) | PMB | " | 1780, 1720, 1655 |

TABLE 9-continued
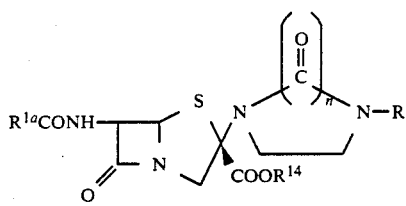
| $R^{1a}$ | R | $R^{14}$ | n | IR(KBr) cm$^{-1}$: |
|---|---|---|---|---|
| HO—⟨C₆H₄⟩—CH(D)—NH—C(=O)—[piperazine-2,3-dione-4-Et] | —N=CH—[4-oxo-5-OBzl-pyridin-2-yl-NH] | PNB | " | 1780, 1720, 1675 |
| HO—⟨C₆H₄⟩—CH(D)—NH—C(=O)—[piperazine-2,3-dione-4-Et] | —N=CH—[1,2,3-thiadiazol-4-yl] | PNB | 1 | 1780, 1710, 1670 |
| " | —N=CH—[pyridin-4-yl] | " | " | 1780, 1710, 1675 |
| " | —N=CH—[3,4-(OH)₂-C₆H₃] | " | " | 1790, 1710, 1670 |
| " | —N=CHC≡CH | " | " | 1780, 1720, 1680 |
| " | —N=CHCH₂Cl | " | " | 1780, 1710, 1675 |
| " | —N=CH—[4-oxo-5-OBzl-1-OBzl-pyridin-2-yl] | " | " | 1780, 1720, 1705, 1675 |

TABLE 9-continued

Structure: R¹ᵃCONH-[β-lactam-S]-...-COOR¹⁴, with N-R group on ring of size n

| R¹ᵃ | R | R¹⁴ | n | IR(KBr) cm⁻¹ |
|---|---|---|---|---|
| 2-Cl, 4-AcO, 5-AcO-phenyl-CH(DL)-NH-C(=O)-N(piperazine-2,3-dione-N'-Et) | -N=CH-(3,4-dihydroxyphenyl) | PNB | 1 | — |
| 3-AcO, 4-AcO-phenyl-CH(DL)-NH-C(=O)-N(piperazine-2,3-dione-N'-Et) | -N=CHCH₂Cl | " | " | 1770, 1710, 1680 |
| HO-phenyl-CH(DL)(CO₂PNB) | -N=CH-(4-oxo-5-OBzl-1-OBzl-pyridinyl) | " | " | 1785, 1730, 1680 |
| PMBO-phenyl-CH(DL)(CO₂PMB) | -N=CH-CHO | DPM | " | 1785, 1735, 1685 |
| PMB-O- | " | " | " | 1785, 1720, 1685 |
| phenyl-CH(DL)(CO₂DPM) | -N=CH-CHO | DPM | 1 | 1785, 1735, 1685 |
| phenyl-CH(DL)(CO₂PNB) | " | PNB | " | 1785, 1740, 1680 |
| phenyl-CH(DL)(CO₂DPM) | -N=CH-CO₂H | DPM | " | — |

TABLE 9-continued

[Structure: R¹ᵃCONH-β-lactam-S-bicyclic with N-C(=O)-(CH₂)ₙ-N-R and COOR¹⁴]

| R¹ᵃ | R | R¹⁴ | n | IR(KBr) cm⁻¹: |
|---|---|---|---|---|
| " | -N=⟨cyclopentenyl⟩ | " | " | — |
| Ph-CH(CO₂PNB)- (DL) | -N=CH-CH=N-N(Me)-N= | PNB | " | 1780, 1720, 1675 |

Note:
*A mixture of cis and trans forms

EXAMPLE 9

In 7 ml of methylene chloride was dissolved 300 mg of (3R,5R,6R)-3-(3-amino 2-oxoimidazolidin-1-yl)-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane. To the solution were added 0.035 ml of methanesulfonyl chloride, 0.042 ml of pyridine and a catalytic amount of 4-(N,N-dimethylamino)pyridine. The mixture was stirred at room temperature for 3 days. The reaction mixture was mixed with 5 ml of water and adjusted to pH 1.5 with 1N hydrochloric acid. The organic layer was separated and mixed with 5 ml of water. The mixture was adjusted to pH 7.5 with a saturated aqueous sodium hydrogencarbonate solution. The organic layer was separated and dried over anhydrous magnesium sulfate. The solvent was removed by distillation under reduced pressure. The residue was purified by column chromatography (eluant: benzene/ethyl acetate=10/1 to 3/2) to obtain 250 mg (yield: 76.2%) of (3R,5R,6R)-3-(3-methanesulfonylamino-2-oxoimidazolidin-1-yl)-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane.

IR (KBr) cm⁻¹: 1785, 1720, 1670

The compounds shown in Table 10 were obtained in the same manner, using the reactants shown in Table 10.

In Table 10, R¹ᵃ, R¹⁴ and R each show a substituent of the following formula.

TABLE 10

[Structure: R¹ᵃCONH-β-lactam-S-bicyclic with imidazolidinone N-R and COOR¹⁴]

| Reactant | Product R¹ᵃ | R | R¹⁴ | IR(KBr) cm⁻¹: |
|---|---|---|---|---|
| Me—NCO | Ph-CH(NH-C(=O)-N-piperazinedione-Et)- (D) | -NHC(=O)NHMe | PNB | 1780, 1710, 1670 |
| AC₂O | " | —NHAc | " | 1780, 1710, 1675 |

TABLE 10-continued

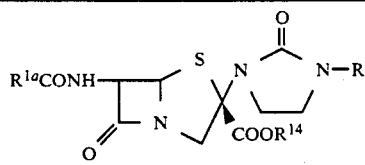

| Reactant | Product R$^{1a}$ | R | R$^{14}$ | IR(KBr) cm$^{-1}$: |
|---|---|---|---|---|
| Ac—O—CHO | Ph-CH(CO$_2$PNB)— (DL) | —NHCHO | PNB | 1780, 1735, 1680 |
| BzlO-pyridinone-COOH*1 | " | —NHC(O)-(5-OBzl-pyridinone) | " | 1780, 1725, 1680 |
| Et—N(CO)(CO)N—COCl*2 (cyclic) | " | —NHC(O)—N(cyclic with Et-N) | " | 1780, 1740, 1715, 1680 |
| Ac$_2$O | " | —NHAc | " | 1785, 1730, 1680 |
| 3,4-diAcO-C$_6$H$_3$—COCl*2 | Ph-CH(CO$_2$PNB)— (DL) | —NHC(O)—C$_6$H$_3$(OAc)$_2$ | PNB | 1770, 1730, 1665 |
| NH$_2$CO—COOH*3 | " | —NHC(O)C(O)NH$_2$ | " | 1780, 1735, 1680 |
| NH$_2$OBzl*4 | " | —NHCNHOBzl (||O) | " | 1780, 1735, 1680 |
| Ac$_2$O | PMBO-C$_6$H$_4$-CH(CO$_2$PMB)— (DL) | —NHAc | " | 1780, 1720, 1680 |
| (CF$_3$CO)$_2$O | " | —NHC(O)CF$_3$ | " | 1785, 1745, 1725, 1675 |
| (EtCO)$_2$O | PMBO-C$_6$H$_4$-CH(CO$_2$PMB)— (DL) | —NHC(O)Et | PNB | 1790, 1730, 1680 |
| Me—NCO | " | —NHC(O)NHMe | " | 1780, 1720, 1680 |
| Et—N(CO)(CO)N—COCl*2 | " | —NHC(O)—N(cyclic with Et-N) | " | 1780, 1730, 1705, 1680 |

TABLE 10-continued

[Structure: R^(1a)CONH- attached to bicyclic β-lactam with S, N-R, COOR^14, and N with C=O]

| Reactant | Product R^(1a) | R | R^14 | IR(KBr) cm^(-1): |
|---|---|---|---|---|
| PNBO—C(=O)—CH₂COCl*² | " | —NHC(=O)CH₂CO₂PNB | " | 1780, 1730, 1675 |
| PNBOCNHCH₂COCl*² (with C=O) | " | —NCCH₂NCOPNB (H, =O, H) | " | 1785, 1725, 1700 |
| [pyridine-COCl structure] | [AcO-phenyl-CH(D)-NH-C(=O)-N-piperazinedione-N-Et] | —NHC(=O)-pyridine | PNB | 1785, 1715, 1675 |
| ClCOCH=CH₂ | [PMBO-phenyl-CH(DL)-CO₂PMB] | —NHCOCH=CH₂ | DPM | 1790, 1730, 1680 |
| ClSO₂NH₂ | " | —NHSO₂NH₂ | " | 1780, 1710 |
| ClCO-pyridine | " | —NHCO-pyridine | " | 1790, 1730, 1680 |
| ClCOCH₂NHCO₂PNB | " | —NHCOCH₂NHCO₂PNB | " | — |

Note
*¹Acylation was effected using N,N'-dicyclohexylcarbodiimide and N-hydroxysuccinimide.
*²Only pyridine was used as the base.
*³Acylation was effected using N,N'-dicyclohexylcarbodiimide.
*⁴Acylation was effected using 1,1'-carbonyldiimidazole.

EXAMPLE 10

In 5 ml of N,N-dimethylformamide was dissolved 390 mg of (3R,5R,6R)-3-[3-(2-chloroethylideneamino)-2-oxoimidazolidin-1-yl]-6-[D-α-(4-ethyl-2,3-dioxo-1-piperazinecarboxamido)-α-(p-hydroxyphenyl)acetamido]-3-(p-nitrobenzyloxycarbonyl)-7-oxo-4-thia-1-azabicyclo[3.2.0]heptane. To the solution were added 70 mg of sodium salt of 5-mercapto-1,2,3-thiadiazole and a catalytic amount of sodium iodide in this order. The mixture was stirred overnight at room temperature. The reaction mixture was concentrated under reduced pressure. The residue was purified by column chromatography (eluant: chloroform/acetone = 5/1 to 1/1) to obtain 190 mg (yield: 44.8%) of (3R,5R,6R)-6-[D-α-(4-ethyl-2,3-dioxo-1-piperazinecarboxamido)-α-(p-hydroxyphenyl)acetamido]-3-(p-nitrobenzyloxycarbonyl)-7-oxo-4-thia-3-{3-[2-(1,2,3-thiadiazol-5-ylthio)ethylideneamino]-2-oxoimidazolidin-1-yl}-1-azabicyclo[3.2.0]heptane.

IR (KBr) cm⁻¹: 1780, 1710, 1670

The compounds shown in Table 11 were obtained in the same manner.

In Table 11, R^(1a) and R each show a substituent of the following formula.

TABLE 11

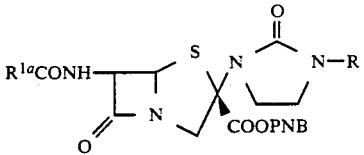

| R[1a] | R | IR(KBr) cm$^{-1}$: |
|---|---|---|
| 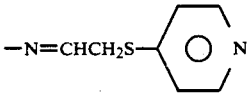 (D) | —N=CHCH$_2$S— 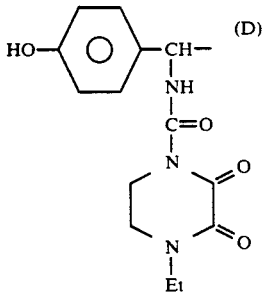 | 1780, 1710, 1675 |
| 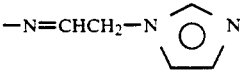 (D) | '' | 1780, 1715, 1670 |
| '' | —N=CHCH$_2$—N⟨⟩N | 1780, 1710, 1670 |

EXAMPLE 11

In a mixed solvent consisting of 5 ml of methylene chloride and 5 ml of methanol was dissolved 400 mg of (3R,5R,6R)-6-[D-α-(4-ethyl-2,3-dioxo-1-piperazinecarboxamido)-α-phenylacetamido]-3-(p-nitrobenzyloxycarbonyl)-7-oxo-3-(2-oxo-3-propynylideneaminoimidazolidin-1-yl)-4-thia-1-azabicyclo[3.2.0]heptane. To the solution were added 110 mg of sodium salt of 5-mercapto-1,2,3-thiadiazole and 198 mg of pyridine salt of p-toluenesulfonic acid. The mixture was stirred at room temperature for 2 days. To the reaction mixture were added 10 ml of water and 10 ml of methylene chloride. The mixture was adjusted to pH 7.0 with a saturated aqueous sodium hydrogencarbonate solution. The organic layer was separated and mixed with 10 ml of water. The mixture was adjusted to pH 2.0 with 2N hydrochloric acid. The organic layer was separated and treated with active carbon. The solvent was removed by distillation under reduced pressure. The residue was purified by column chromatography (eluant: chloroform/acetone=20/1 to 3/2) to obtain 290 mg (yield: 63.6%) of (3R,5R,6R)-6--[D-α-(4-ethyl-2,3-dioxo-1-piperazinecarboxamido)-α-phenylacetamido]-3-(p-nitrobenzyloxycarbonyl)-7-oxo-3-{2-oxo-3-[3-(1,2,3-thiadiazol-5-ylthio)allylideneamino]imidazolidin-1-yl}-4-thia-1-azabicyclo[3.2.0]heptane (a mixture of cis and trans forms).

IR (KBr) cm$^{-1}$: 1780, 1710, 1675

The compounds shown in Table 12 were obtained in the same manner.

In Table 12, R[1a] and R each show a substituent of the following formula.

TABLE 12

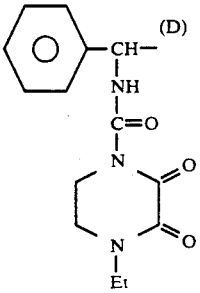

| R<sup>1a</sup> | R | IR(KBr) cm<sup>-1</sup> |
|---|---|---|
| 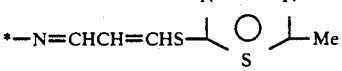 | *—N=CHCH=CHS—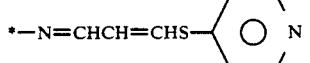—Me | 1780, 1710, 1680 |
| " | *—N=CHCH=CHS—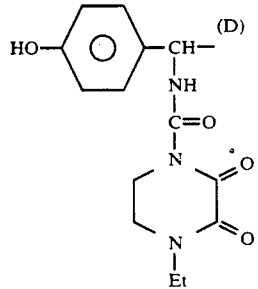 | 1780, 1710, 1680 |
| 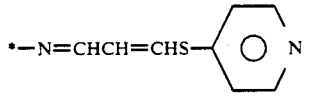 | *—N=CHCH=CHS—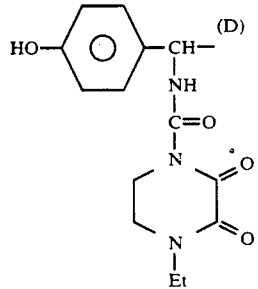 | 1780, 1710, 1670 |

Note:
*A mixture of cis and trans forms

EXAMPLE 12

To a mixed solvent consisting of 5 ml of ethylacetate and 5 ml of water were added 200 mg of 5% palladium-carbon and 220 mg of (3R,5R,6R)-6-[D-α-(4-ethyl-2,3-dioxo-1-piperazinecarboxamido)-α-phenylacetamido]-3-[3-(2-furfurylideneamino)-2-oxoimidazolidin-1-yl]-3-(p-nitrobenzyloxycarbonyl)-7-oxo-4-thia-1-azabicyclo[3.2.0]heptane. The mixture was stirred at room temperature for 2 hours in a hydrogen atmosphere. The insolubles were removed by filtration. The filtrate was adjusted to pH 6.5 with a saturated aqueous sodium hydrogencarbonate solution. The aqueous layer was separated and freeze-dried to obtain 50 mg (yield: 26.5%) of sodium salt of (3R,5R,6R)-3-carboxy-6-[D-α-(4-ethyl-2,3-dioxo-1-piperazinecarboxamido)-α-phenylacetamido]-3-[3-(2-furfurylideneamino)-2-oxoimidazolidin-1-yl]-7-oxo-4-thia-1-azabicyclo[3.2.0]heptane.

IR (KBr) cm<sup>-1</sup>: 1770, 1710, 1670, 1620
NMR (D$_2$O) δ: 1.17(3H, t, J=7 Hz), 3.20–4.20(1H, m), 5.40(1H, d, J=4 Hz), 5.48(1H, s), 5.54(1H, d, J=4 Hz), 6.58(1H, dd, J=2 Hz, J=3 Hz), 6.80(1H, d, J=3 Hz), 7.48(5H, s), 7.40–7.70(2H, m)

The compounds shown in Table 13 were obtained in the same manner.

In Table 13, R<sup>1a</sup>, R<sup>15</sup> and R<sup>a</sup> each show a substituent of the following formula, and n is 1 or 2 as shown in Table 13.

TABLE 13
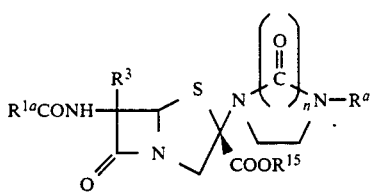
| $R^{1a}$ | $R^a$ | $R^{15}$ | n | IR(KBr) cm$^{-1}$: |
|---|---|---|---|---|
| (D) Phenyl-CH(CH₃)-NH-C(=O)-[1-(4-Et-2,3-dioxopiperazinyl)] | -N=C(S-CH₂-CH₂-S) (1,3-dithiolan-2-ylidene) | Na | 1 | 1770, 1705, 1670, 1620 |
| (D) Thien-2-yl-CH(CH₃)-NH-C(=O)-[1-(4-Et-2,3-dioxopiperazinyl)] | " | H | " | 1780, 1710, 1670, 1650 |
| (D) 4-HO-Phenyl-CH(CH₃)-NH-C(=O)-[1-(4-Et-2,3-dioxopiperazinyl)] | " | " | " | 1770, 1700, 1660 |
| (DL) 3,4-(AcO)₂-Phenyl-CH(CH₃)-NH-C(=O)-[1-(4-Et-2,3-dioxopiperazinyl)] | -N=C(S-CH₂-CH₂-S) | H | 1 | 1770, 1710, 1670, 1650 |

TABLE 13-continued

Structure: R¹ᵃCONH-[β-lactam with R³]-S-[ring with COOR¹⁵, CH₂N, (C=O)ₙ N-Rᵃ]

| R¹ᵃ | Rᵃ | R¹⁵ | n | IR(KBr) cm⁻¹: |
|---|---|---|---|---|
| (DL) 2-Cl, 4,5-(AcO)₂-C₆H₂-CH(NHC(=O)-N-[2,3-dioxo-4-ethyl-piperazinyl])- | " | " | " | 1775, 1705, 1680, 1650 |
| (D) C₆H₅-CH(NH₂)- | " | " | " | 1765, 1680, 1610 |
| (D) C₆H₅-CH(NHC(=O)-N-[2,3-dioxo-4-phenyl-piperazinyl])- | " | " | " | 1780, 1705, 1690 |
| (D) 4-HO-C₆H₄-CH(NH₂)- | " | " | " | 1765, 1680, 1605 |
| (DL) MeS-CH(NHC(=O)-N-[2,3-dioxo-4-ethyl-piperazinyl])- | -N=C(S-CH₂CH₂-S) (1,3-dithiolan-2-ylidene) | H | 1 | 1780, 1705, 1670 |
| (DL) C₆H₅-CH(CO₂H)- | " | " | " | 1770, 1720, 1700, 1650 |

TABLE 13-continued
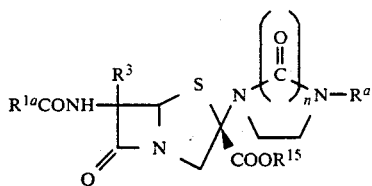
| $R^{1a}$ | $R^a$ | $R^{15}$ | n | IR(KBr) cm$^{-1}$: |
|---|---|---|---|---|
| (D) [phenyl-CH(O-CHO)-] | " | Na | " | 1770, 1700, 1610 |
| (DL) [thiophene-CH(CO$_2$H)-] | " | H | " | 1780, 1720, 1680, 1650 |
| [aminothiazole-C(=N-OMe)-] | " | Na | " | 1770, 1700~1660, 1620 |
| [aminothiazole-C(=N-O-CH$_2$CH$_2$F)-] | " | " | " | 1770, 1690, 1650, 1615 |
| (DL) [aminothiazole-CH(NH$_2$)-] | " | H | " | 1770, 1700~1660, 1610 |
| (D) [HO-phenyl-CH(NH-C(=O)-pyridinone)-] | [-N=C(S-CH$_2$CH$_2$-S) (dithiolane)] | H | 1 | 1770, 1700, 1680, 1605 |
| [aminothiazole-C(=N-OMe)-] | -N=CH-phenyl | " | " | 1775, 1700, 1660, 1620 |
| (DL) [phenyl-CH(CO$_2$H)-] | " | " | " | 1775, 1720, 1680 |

TABLE 13-continued
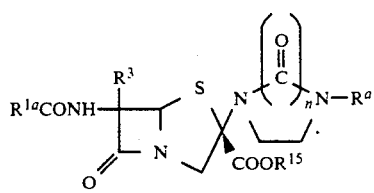
| $R^{1a}$ | $R^a$ | $R^{15}$ | n | IR(KBr) cm$^{-1}$: |
|---|---|---|---|---|
| (D) ![phenyl-CH(NH-CO-N-piperazine-2,3-dione-N-Et)] | " | " | " | 1780, 1710, 1680 |
| " | " | Na | 2 | 1770, 1710, 1670, 1615 |
| (DL) ![phenyl-CH(CO2H)-] | —N=CH—(furan) | H | 1 | 1780, 1715, 1650 |
| (D) ![phenyl-CH(NH2)-] | —N=CH—(furan) | H | 1 | 1770, 1685, 1610 |
| (DL) ![benzothiophene-CH(NH-CO-N-piperazine-2,3-dione-N-Et)] | " | Na | " | 1775, 1710, 1675, 1620 |
| (DL) ![naphthyl-CH(NH-CO-N-piperazine-2,3-dione-N-Et)] | " | " | " | 1770, 1710, 1675, 1620 |

TABLE 13-continued

[Structure: R¹ᵃCONH-[β-lactam with R³]-S-[thiazolidine with COOR¹⁵ and N-(C=O)ₙ-Rᵃ ring]]

| R¹ᵃ | Rᵃ | R¹⁵ | n | IR(KBr) cm⁻¹: |
|---|---|---|---|---|
| (DL) PhCH(NH-C(=O)-N[piperazine-2,3-dione-N'-Et])- | -N=CH-C₆H₄-Cl | " | " | 1770, 1710, 1660, 1610 |
| " | -N=C(SMe)₂ | H | " | 1780, 1710, 1675 |
| (D) PhCH(CO₂H)- | " | " | " | 1775, 1715, 1670 |
| (DL) 3,4-(HO)₂C₆H₃-CH(CO₂Na)- | -N=C(S-CH₂CH₂CH₂-S) (cyclic dithio) | Na | 1 | 1760, 1710, 1660, 1610 |
| (DL) 4-(H₂NC(O)O)-C₆H₄-CH(CO₂Na)- | -NHC(=O)NH₂ | " | " | 1770, 1730, 1670, 1600 |
| (DL) 2-Cl-4,6-(HO)₂-C₆H₂-CH(CO₂Na)- | " | " | " | 1760, 1710, 1660, 1600 |
| (DL) 3,4-(HO)₂C₆H₃-CH(CO₂Na)- | " | " | " | 1765, 1705, 1660, 1600 |

TABLE 13-continued
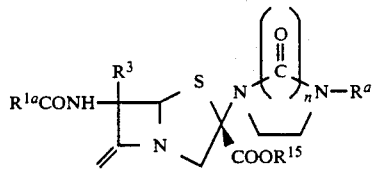
| $R^{1a}$ | $R^a$ | $R^{15}$ | n | IR(KBr) cm$^{-1}$: |
|---|---|---|---|---|
| (DL) 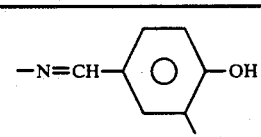 | —N=CH—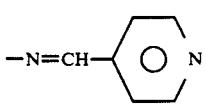—OH, OH | " | " | 1770, 1710, 1690, 1675, 1600 |
| (D) 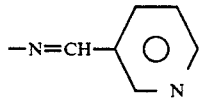 | —N=CH—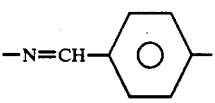 (N) | Na | 1 | 1770, 1700, 1670, 1620 |
| " | —N=CH—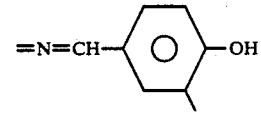 | " | " | 1770, 1705, 1670, 1610 |
| " | —N=CH—Ac | " | " | 1780, 1720, 1670, 1615 |
| " | —N=CH—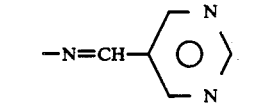—OH | H | " | 1780, 1715, 1675 |
| " | =N=CH—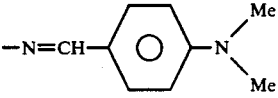—OH, OH | " | " | 1780, 1715, 1680 |
| " | —N=CH— (N,N) | Na | " | 1770, 1705, 1670, 1615 |
| " | —N=CH—⬡—N(Me)(Me) | " | " | 1775, 1715, 1675, 1605 |

TABLE 13-continued
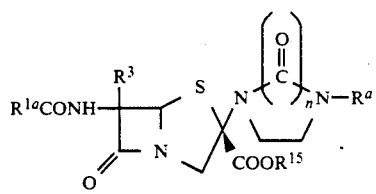
| R$^{1a}$ | R$^a$ | R$^{15}$ | n | IR(KBr) cm$^{-1}$: |
|---|---|---|---|---|
| (D) PhCH(NHC(O)-piperazine-2,3-dione-N-Et)- | —N=CH—CO$_2$Na | Na | 1 | 1770, 1710, 1670, 1600 |
| " | —N=CH—C$_6$H$_4$—NH$_2$ | " | " | 1770, 1710, 1670, 1600 |
| " | —N=CH-(pyrazol-3-yl, NH) | " | " | 1775, 1710, 1680, 1610 |
| " | —NHC(O)NHMe | H | " | 1780, 1710, 1665 |
| " | —NHHAc | " | " | 1780, 1710, 1670 |
| " | —N=CH—C$_6$H$_4$—OH (o) | Na | " | 1775, 1710, 1675, 1615 |
| " | —N=CHCH$_2$S-(pyridin-4-yl) | " | " | 1775, 1710, 1670, 1620 |
| (D) PhCH(NHC(O)-piperazine-2,3-dione-N-Et)- | *—N=CHCH=CHS-(5-Me-1,3,4-thiadiazol-2-yl) | Na | 1 | 1770, 1710, 1675, 1615 |
| " | *—N=CHCH=CHS-(pyridin-4-yl) | " | " | 1780, 1720, 1680, 1620 |

TABLE 13-continued
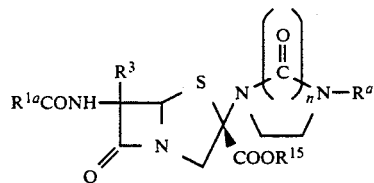
| $R^{1a}$ | $R^a$ | $R^{15}$ | n | IR(KBr) cm$^{-1}$: |
|---|---|---|---|---|
| " | ![structure with -N=CHN(H)+ azepane ring, Cl⁻] | H | " | 1775, 1710, 1680, 1610 |
| " | ![-N=CH-pyrimidine] | Na | " | 1775, 1710, 1675, 1620 |
| AcO-C₆H₄-CH(D)(CH₃)-NH-CO-N(piperazine-2,3-dione-N'-Et) | -NHC(O)-piperidine | " | " | 1775, 1710, 1670, 1610 |
| HO-C₆H₄-CH(D)(CH₃)-NH-CO-N(piperazine-2,3-dione-N'-Et) | -N=CH-(4-oxo-5-hydroxy-1H-pyridine) | " | " | 1770, 1710, 1670, 1610 |
| HO-C₆H₄-CH(D)(CH₃)-NH-CO-N(piperazine-2,3-dione-N'-Et) | -N=CH-(thiadiazole) | Na | 1 | 1775, 1710, 1670, 1610 |
| " | -N=CH-pyridine | " | " | 1770, 1710, 1670, 1610 |

TABLE 13-continued

Structure:
R¹ᵃCONH–[β-lactam with R³]–S–[ring with C=O, (C)ₙ, N-Rᵃ]–COOR¹⁵

| R¹ᵃ | Rᵃ | R¹⁵ | n | IR(KBr) cm⁻¹: |
|---|---|---|---|---|
| " | –N=CH–(3,4-dihydroxyphenyl) | " | " | 1765, 1705, 1670, 1600 |
| " | –N=CHCH₂S–(1,3,4-thiadiazol-2-yl) | " | " | 1780, 1710, 1680, 1610 |
| " | –N=CH–(4-oxo-5-hydroxy-1-hydroxy-1,4-dihydropyridin-2-yl) | " | " | 1770, 1710, 1670, 1605 |
| " | –N=CHCH₂S–(pyridin-4-yl) | " | " | 1770, 1710, 1670, 1615 |
| " | –N=CHCH₂–N(imidazol-1-yl) | " | " | 1775, 1710, 1670, 1610 |
| (D) HO–C₆H₄–CH(CH₃)–NH–C(=O)–N(4-ethyl-2,3-dioxopiperazin-1-yl) | *–N=CHCH=CHS–(pyridin-4-yl) | Na | 1 | 1765, 1705, 1670, 1620 |
| " | –NH₂ | " | " | 1770, 1710, 1670, 1600 |
| H₂N–C(=N–)–S-thiazole with =N–OMe (aminothiazolyl methoxyimino) | –N=CH–(pyridin-4-yl) | H | " | 1775, 1710, 1660, 1620 |
| (DL) C₆H₅–CH(CO₂H)– | –N=CH–(3,4-dihydroxyphenyl) | " | " | 1770, 1720, 1700 |

TABLE 13-continued
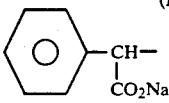
| $R^{1a}$ | $R^a$ | $R^{15}$ | n | IR(KBr) cm$^{-1}$: |
|---|---|---|---|---|
| (DL) 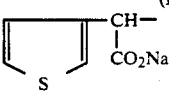 | —NH$_2$ | Na | " | 1770, 1695, 1660, 1610 |
| (DL) 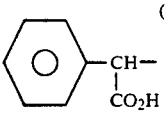 | ∝1 | " | " | 1770, 1710, 1660, 1600 |
| (DL) 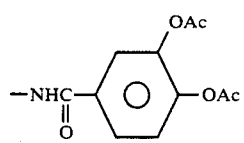 | 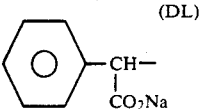 | H | " | 1775, 1730, 1705, 1660 |
| (DL) 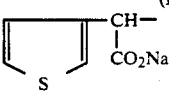 | 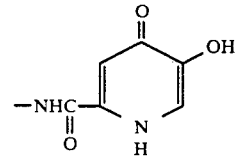 | Na | 1 | 1770, 1710, 1660, 1610 |
| " | 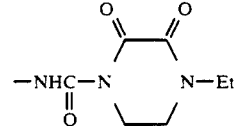 | " | " | 1770, 1720, 1675, 1600 |
| " | —NHAc | " | " | 1760, 1710, 1620, 1605 |
| " | —NHCHO | " | " | 1770, 1710, 1660, 1600 |
| " | —NHC—CNH$_2$ <br> ‖ ‖ <br> O O | " | " | 1770, 1670, 1600 |
| " | —NHCNHOH <br> ‖ <br> O | " | " | 1770, 1710, 1660, 1600 |
| " | 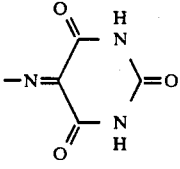 | " | " | 1765, 1700, 1660, 1600 |
| (DL) 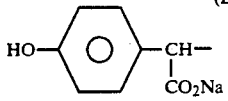 | —NHSO$_3$Na | Na | 1 | 1760, 1700, 1660, 1600 |

TABLE 13-continued

[Structure: R¹ᵃCONH— attached to β-lactam with R³, S, connected to N-containing ring with (C=O)ₙ and N—Rᵃ, with COOR¹⁵]

| R¹ᵃ | Rᵃ | R¹⁵ | n | IR(KBr) cm⁻¹: |
|---|---|---|---|---|
| (D) phenyl-CH(NH-C(=O)-piperazine-2,3-dione-N-Et)— | —N=CH—[oxadiazole: O, N, N, S ring] | " | " | 1770, 1710, 1670, 1610 |

The compounds wherein R¹⁵ was a hydrogen atom, were obtained by, after the hydrogenation, removing the insolubles by filtration, adding to the filtrate a mixed solvent of ethyl acetate and tetrahydrofuran, adjusting the resulting mixture to pH 2.0 with 1N hydrochloric acid, separating the organic layer, and subjecting the organic layer to washing with water, drying over anhydrous magnesium sulfate and distillation for solvent removal.

EXAMPLE 13

The compounds shown in Table 14 were obtained in the same manner as in Example 12

In Table 14, Rᵃ and R¹ᵃ each show a substituent of the following formula.

TABLE 14

[Structure: R¹ᵃCONH— attached to β-lactam with S, connected to imidazolidinone ring with C=O and N—Rᵃ, with COONa]

| R¹ᵃ | Rᵃ | IR(KBr) cm⁻¹: |
|---|---|---|
| (DL) HO-C₆H₄-CH(CO₂Na)— | —N=CH—[3-hydroxy-1-hydroxy-4-oxo-pyridine] | 1770, 1700, 1600 |
| (DL) C₆H₅-CH(CO₂Na)— | —N=CHCH=NOMe | 1770, 1610 |
| (D) AcO-C₆H₄-CH(NH-SO₃Na)— | —NHCONH₂ | 1750, 1660–1600 |
| (D) AcO-C₆H₄-CH(NH₂)— | " | 1765, 1710, 1700, 1680–1660, 1600 |

TABLE 14-continued

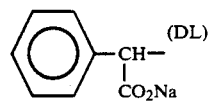

| R$^{1a}$ | R$^a$ | IR(KBr) cm$^{-1}$: |
|---|---|---|
| 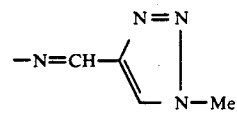 (DL) | 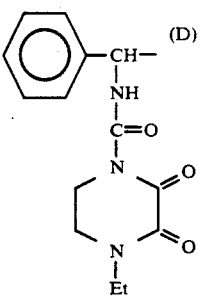 | 1765, 1700, 1650, 1610 |

EXAMPLE 14

In the same manner as in Example 12, there was obtained disodium salt of (3R,5R,6R)-3-carboxy-6-[DL-α-carboxy-α-phenylacetamido]-6-methoxy-7-oxo-3-(2-oxo-3-ureidoimidazolidin-1-yl)-4-thia-1-azabicyclo[3.2.0]heptane.

IR (KBr) cm$^{-1}$: 1770, 1670, 1600

EXAMPLE 15

(1) In a mixed solvent consisting of 1 ml of methylene chloride and 1 ml of anisole was dissolved 210 mg of (3R,5R,6R)-3-diphenylmethyloxycarbonyl-6-[D--α-(4-ethyl-2,3-dioxo-1-piperazinecarboxamido)-α-phenylacetamido]-3-[3-(4-nitrobenzylideneamino)-2-oxoimidazolidin-1-yl]-7-oxo-4-thia-1-azabicyclo[3.2.0-]heptane. The solution was cooled to −30° C.

(2) 95 mg of anhydrous aluminum chloride was dissolved in 1 ml of anisole. This solution was added to the solution prepared in (1) above, at −30° C. The mixture was stirred at −20° C. for 20 minutes. The reaction mixture was added to a mixed solvent consisting of 10 ml of tetrahydrofuran, 20 ml of ethyl acetate and 10 ml of water. The resulting mixture was adjusted to pH 1.0 with 1N hydrochloric acid. The insolubles were removed by filtration. The organic layer was separated and mixed with 10 ml of water. The mixture was adjusted to pH 6.5 with a saturated aqueous sodium hydrogencarbonate solution. The aqueous layer was separated and freeze-dried to obtain 120 mg (yield: 72.5%) of sodium salt of (3R,5R,6R)-3-carboxy-6-[D--α-(4-ethyl-2,3-dioxo-1-piperazinecarboxamido)-α-phenylacetamido]-3-[3-(4-nitrobenzylideneamino)-2-oxoimidazolidin-1-yl]-7-oxo-4-thia-1-azabicyclo[3.2.0-]heptane.

IR (KBr) cm$^{-1}$: 1770, 1710, 1675, 1615

The compounds shown in Table 15 were obtained in the same manner.

In Table 15, R$^{1a}$, R$^{15}$ and R each show a substituent of the following formula.

TABLE 15

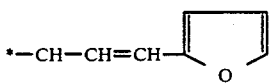

| R$^{1a}$ | R | R$^{15}$ | IR (KBr) cm$^{-1}$: |
|---|---|---|---|
| 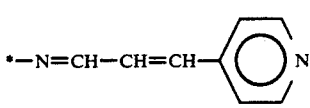 (D) | *—CH—CH=CH—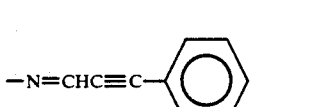 | Na | 1780, 1710, 1680, 1620 |
| " | *—N=CH—CH=CH— | " | 1780, 1720, 1675, 1610 |
| " | —N=CHC≡C—⌬ | " | 1780, 1710, 1680, 1620 |
| " | —N=CHCH=CH$_2$ | " | 1770, 1705, 1675, 1605 |

TABLE 15-continued

Structure: R¹ᵃCONH-[β-lactam-S]-[thiazolidine with N-C(=O)-N-R]-COOR¹⁵

| R¹ᵃ | R | R¹⁵ | IR (KBr) cm⁻¹: |
|---|---|---|---|
| " | —N=CHC≡CH | " | 1770, 1710, 1670, 1620 |
| " | —N=CHCH=CH—C₆H₅ | H | 1780, 1710, 1670 |
| HO-C₆H₄-CH(CO₂Na)- (DL) | —N=CHCH=CH₂ | Na | 1770, 1700, 1650, 1600 |
| " | —N=CHC≡CH | " | 1770, 1705, 1655, 1600 |
| C₆H₅-CH(CO₂Na)- (DL) | *—N=CHCH=CHCO₂Na | " | 1770, 1690, 1660, 1610 |
| " | —N=CHCH=CH₂ | " | 1770, 1700, 1650, 1600 |
| " | —N=CHCH=NOCH₂CO₂Na | " | 1770, 1705, 1600 |
| HO-C₆H₄-CH(CO₂Na)- (DL) | —N=CHCH=NNHCONH₂ | " | 1760, 1660, 1600 |
| " | —N=CHCH=NNHCHO | " | 1765, 1680, 1600 |
| HO-C₆H₄-CH(CO₂Na)- (DL) | —N=CHCH=NNHCOCH₂N⁺(Me)₃ Cl⁻ | Na | 1770, 1690, 1620 |
| " | —N=CHCH=NNHC(=NH)NH₂ | " | 1760, 1600 |
| " | —NHCONHSO₂NH₂ | " | 1760, 1600 |
| C₆H₅-CH(CO₂Na)- (DL) | —N=CHCH=CHCN | " | 1765, 1705, 1600 |
| " | —N=CHCONH₂ | " | 1770, 1720, 1660, 1600 |
| " | —N=CHCH=CHCONH₂ | " | 1765, 1700, 1660, 1600 |
| " | —N=CHC≡N | " | 1770, 1720, 1660, 1610 |
| " | —N=cyclopentenyl | " | 1770, 1710, 1690, 1660, 1610 |
| HO-C₆H₄-CH(CO₂Na)- (DL) | —NHCO-(4-pyridyl) | Na | 1770, 1710, 1680~1660, 1600 |
| " | —NHCOCH=CH₂ | " | 1770, 1710, 1680~1650, 1600 |

TABLE 15-continued

[Structure: R¹ᵃCONH-[β-lactam-thia-azabicyclo ring with COOR¹⁵]-N(C=O)N-R imidazolidinone]

| R¹ᵃ | R | R¹⁵ | IR (KBr) cm⁻¹: |
|---|---|---|---|
| " | —NHSO₂NH₂ | " | 1760, 1700, 1650, 1620, 1600 |
| " | —N=CHCH=CHCH=CHCON(cyclohexyl ring) | " | 1770, 1700, 1600 |

Note:
*A mixture of cis and trans forms

EXAMPLE 16

(1) In 6 ml of methylene chloride was dissolved 300 mg of (3R,5R,6R)-3-(3-acetylamino-2-oxoimidazolidin-1-yl)-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane. The solution was cooled to −30° C. To the solution was dropwise added 2 ml of an anisole solution containing 280 mg of anhydrous aluminum chloride, while maintaining the reaction temperature at −20° C. or below. The mixture was stirred at −10° to 0° C. for 30 minutes. The reaction mixture was added to a mixed solvent consisting of 10 ml of water, 15 ml of ethyl acetate and 10 ml of tetrahydrofuran. The resulting mixture was adjusted to pH 1.0 with 2N hydrochloric acid. The organic layer was separated and mixed with 10 ml of water. The mixture was adjusted to pH 7.5 with a saturated aqueous sodium hydrogencarbonate solution. The aqueous layer was separated. Thereto were added 15 ml of ethyl acetate and 10 ml of tetrahydrofuran. The mixture was adjusted to pH 1.0 with 2N hydrochloric acid. The organic layer was separated, washed with a saturated aqueous sodium chloride solution, and dried over anhydrous magnesium sulfate. The solvent was removed by distillation under reduced pressure to obtain 160 mg of (3R,5R,6R)-3-(3-acetylamino-2-oxoimidazolidin-1-yl)-6-[DL-α-carboxy-α-(p-hydroxyphenyl)acetamido]-3-(p-nitrobenzyloxycarbonyl)-7-oxo-4-thia-1-azabicyclo[3.2.0]heptane.

(2) In a mixed solvent consisting of 3 ml of water, 3 ml of methanol and 3 ml of tetrahydrofuran was dissolved 160 mg of (3R,5R,6R)-3-(3-acetylamino-2-oxoimidazolidin-1-yl)-6-[DL-α-carboxy-α-(p-hydroxyphenyl)acetamido]-3-(p-nitrobenzyloxycarbonyl)-7-oxo-4-thia-1-azabicyclo[3.2.0]heptane. To the solution was added 150 mg of 5% palladium-carbon. The mixture was stirred at room temperature for 2 hours in a hydrogen atmosphere. The insolubles were removed by filtration. The filtrate was concentrated under reduced pressure. To the residue were added 5 ml of water and 10 ml of ethyl acetate. The mixture was adjusted to pH 6.5 with a saturated aqueous sodium hydrogencarbonate solution. The aqueous layer was separated, purified by reversed phase column chromatography (eluant: water) and freeze-dried to obtain 120 mg (yield: 64.2%) of disodium salt of (3R,5R,6R)-3-(3-acetylamino-2-oxoimiaazolidin-1-yl)-3-carboxy-6-[DL-α-carboxy-α-(p-hydroxyphenyl)acetamido]-7-oxo-4-thia-1-azabicyclo[3.2.0]heptane.

IR (KBr) cm⁻¹: 1770, 1710, 1650, 1600,

The compounds shown in Table 16 were obtained in the same manner.

In Table 16, R¹ᵃ and R each show a substituent of the following formula.

TABLE 16

[Structure: R¹ᵃCONH-[β-lactam-thia-azabicyclo ring with COONa]-N(C=O)N-R imidazolidinone]

| R¹ᵃ | R | IR (KBr) cm⁻¹: |
|---|---|---|
| HO—⟨phenyl⟩—CH(CO₂Na)— (DL) | —NHCNHMe<br>‖<br>O | 1770, 1710, 1660, 1600 |
| " | —NHCCF₃<br>‖<br>O | 1765, 1690, 1655, 1605 |
| " | —NHCEt<br>‖<br>O | 1770, 1710, 1660, 1600 |
| " | —NHSO₂Me | 1760, 1700, 1650, 1600 |

TABLE 16-continued
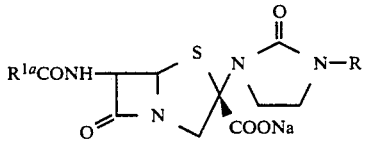
| R1a | R | IR (KBr) cm−1: |
|---|---|---|
| " | 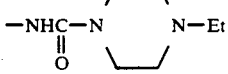 | 1760, 1720, 1660, 1600 |
| " | −NHCCH₂CO₂Na<br>‖<br>O | 1770, 1710, 1660, 1625, 1600 |
| 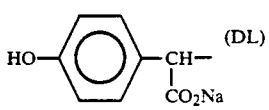 (DL) | −NHCCH₂NH₂<br>‖<br>O | 1770, 1710, 1660, 1610 |
| " | −NH₂ | 1760, 1690, 1650, 1610 |
| " | 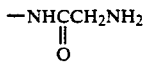 | 1770, 1700, 1660, 1600 |
| 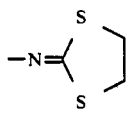 | " | 1770, 1710, 1660, 1600 |
| " | −NH₂ | 1760, 1705, 1660, 1600 |
| 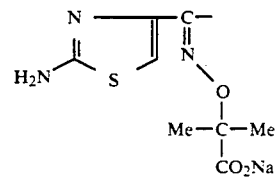 (DL) | " | 1770, 1710, 1660, 1610 |
| 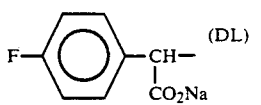 (DL) | " | 1760, 1710, 1650, 1600 |
| 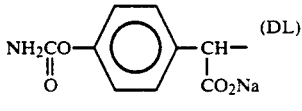 (DL) | −NH₂ | 1770, 1710, 1660, 1605 |
| 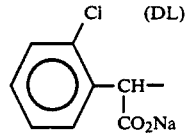 (DL) | −NHCNH₂<br>‖<br>O | 1765, 1705, 1670, 1600 |
| 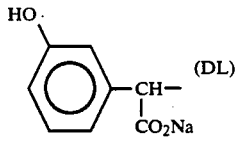 (DL) | " | 1770, 1715, 1670, 1600 |

TABLE 16-continued

[Structure: R¹ᵃCONH-[β-lactam-thia-imidazolidinone ring system]-COONa with N-R substituent]

| R¹ᵃ | R | IR (KBr) cm⁻¹ |
|---|---|---|
| [4-F, 4-HO-phenyl-CH(CO₂Na)-] (DL) | " | 1765, 1710, 1665, 1600 |
| [phenyl-CH(CO₂Na)-] (DL) | —N=CHCO₂Na | 1765, 1700, 1650, 1600 |
| [aminothiazole-oxyimino with AcO, OAc phenyl-CH(CO₂Na)-O-N= group] | [−N=C(S-CH₂-CH₂-S) dithiolane] | 1770, 1660, 1600 |
| [aminothiazole-oxyimino with -O-CH₂-CO₂Na group] | [−N=C(S-CH₂-CH₂-S) dithiolane] | 1770, 1700~1660, 1600 |

EXAMPLE 17

(1) (3R,5R,6R)-3-(3-amino-2-oxoimidazolidin-1-yl)-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane in place of (3R,5R,6R)-3-(3-acetylamino-2-oxoimidazolidin-1-yl)-6-{DL-α-(p-methoxybenzyloxycarbonyl)-α-[4-(p-methoxybenzyloxy)phenyl]acetamido}-3-(p-nitrobenzyloxycarbonyl)-7-oxo-4-thia-1-azabicyclo[3.2.0]heptane was subjected to the same procedure as in Example 16 (1) to obtain (3R,5R,6R)-3-(3-amino-2-oxoimidazolidin-1-yl)-6-[DL-α-carboxy-α-(p-hydroxyphenyl)acetamido]-3-(p-nitrobenzyloxycarbonyl)-7-oxo-4-thia-1-azabicyclo[3.2.0]heptane.

IR (KBr) cm⁻¹: 1780, 1720, 1670

(2) In 3 ml of N,N-dimethylformamide was dissolved 250 mg of (3R,5R,6R)-3-(3-amino-2-oxoimidazolidin-1-yl)-6-[DL-α-carboxy-α-(p-hydroxyphenyl)acetamido]-3-(p-nitrobenzyloxycarbonyl)-7-oxo-4-thia-1-azabicyclo[3.2.0]heptane. To the solution was added 130 mg of a sulfur trioxide-pyridine complex, and the mixture was stirred at room temperature for 1 day. The reaction mixture was poured into 10 ml of water in 5 minutes while maintaining the reaction mixture at pH 6.0 to 7.0 with a saturated aqueous sodium hydrogencarbonate solution. The reaction mixture was concentrated under reduced pressure. The residue was dissolved in a mixed solvent consisting of 10 ml of water and 10 ml of ethyl acetate. The solution was adjusted to pH 2.0 with 1N hydrochloric acid. The aqueous layer was separated, adjusted to pH 6.0 with a saturated aqueous sodium hydrogencarbonate solution, and concentrated under reduced pressure. The residue was purified by reversed phase column chromatography (eluant: water) to obtain 30 mg (yield: 9.9%) of disodium salt of (3R,5R,6R)-6-[DL-α-carboxy-α-(p-hydroxyphenyl)acetamido]-3-(p-nitrobenzyloxycarbonyl)-7-oxo-3-(2-oxo-3-sulfoaminoimidazolidin-1-yl)-4-thia-1-azabicyclo[3.2.0]heptane.

IR (KBr) cm⁻¹: 1780, 1740, 1710, 1655, 1600

EXAMPLE 18

To a mixed solvent consisting of 2 ml of tetrahydrofuran, 2 ml of methanol and 2 ml of water were added 200 mg of an iron powder, 200 mg of ammonium chloride and 100 mg of (3R,5R,6R)-3-(p-nitrobenzyloxycarbonyl)-6-[DL-α-(p-nitrobezyloxycarbonyl)-α-phenylacetamido]-7-oxo-3-[2-oxo-3-(4-sulfo-2-butenylideneamino)imidazolidin-1-yl]-4-thia-1-azabicyclo[3.2.0]heptane. The mixture was stirred at room temperature for 6 hours. The insolubles were removed by filtration. The filtrate was concentrated under reduced pressure. To the residue were added 5 ml of ethyl acetate and 5 ml of water. The mixture was adjusted to pH 6.0 with a saturated aqueous sodium hydrogencarbonate solution. The aqueous layer was separated and purified by reversed phase column chromatography (eluant: water) to obtain 30 mg (yield: 39.5%) of trisodium salt of (3R,5R,6R)-3-carboxy-6-(DL-α-carboxy-α-phenylacetamido)-7-oxo-3-[3-(4-sulfo-2-butenylideneamino)-2-oxoimidazolidin-1-yl]-4-thia-1-azabicyclo[3.2.0]heptane.

IR (KBr) cm$^{-1}$: 1770, 1710, 1660, 1600

EXAMPLE 19

In 5 ml of N,N-dimethylformamide was dissolved 300 mg of (3R,5R,6R)-3-[3-(2-chloroethylideneamino)-2-oxoimidazolidin-1-yl]-6-[D-α-(4-ethyl-2,3-dioxo-1-piperazinecarboxamido)-α-(p-hydroxyphenyl)acetamido]-3-(p-nitrobenzyloxycarbonyl)-7-oxo-4-thia-1-azabicyclo[3.2.0]heptane. To the solution were added 3 ml of pyridine and a catalytic amount of sodium iodide. The mixture was stirred at room temperature for 1 day. The reaction mixture was subjected to evaporation to dryness under reduced pressure. The residue was dissolved in a mixed solvent consisting of 5 ml of water, 5 ml of methanol and 5 ml of ethyl acetate. To the solution was added 300 mg of 5% palladium-carbon. The mixture was stirred at room temperature for 5 hours in a hydrogen atmosphere. The insolubles were removed by filtration. The filtrate was concentrated under reduced pressure. To the residue were added 20 ml of water and 20 ml of ethyl acetate. The mixture was adjusted to pH 7.0 with a saturated sodium hydrogencarbonate solution. The aqueous layer was separated, purified by reversed phase column chromatography (eluant: water/acetonitrile=9/1 to 6/1), and freeze-dried to obtain 67 mg (yield: 25.3%) of (3R,5R,6R)-6-[D-α-(4-ethyl-2,3-dioxo-1-piperazinecarboxamido)-α-(p-hydroxyphenyl)acetamido]-7-oxo-3-{2-oxo-3-[2-(1-pyridinium)ethylideneamino]imidazolidin-1-yl}-4-thia-1-azabicyclo[3.2.0]heptane-3-carboxylate.

IR (KBr) cm$^{-1}$: 1770, 1710, 1665, 1615

The compounds shown in Table 17 were obtained in the same manner.

In Table 17, R$^{1a}$ and R each show a substituent of the following formula.

TABLE 17

[Structure: R$^{1a}$CONH- attached to β-lactam-thiazolidine bicyclic system with N-R and COO$^{\ominus}$ substituents]

| R$^{1a}$ | R | IR(KBr) cm$^{-1}$: |
|---|---|---|
| HO-C$_6$H$_4$-CH(D)-NH-C(=O)-[4-ethyl-2,3-dioxopiperazin-1-yl] | -N=CHCH$_2$-N$^{\oplus}$(Me)(Me)Me | 1775, 1715, 1670, 1620 |
| " | -N=CHCH$_2$-N$^{\oplus}$(pyridinium-4-yl with 2-oxoimidazolidin-1-yl substituent) | 1770, 1705, 1670, 1630, 1610 |
| " | -N=CHCH$_2$-N$^{\oplus}$(4-Me-pyridinium) | 1770, 1705, 1665, 1610 |
| " | -N=CHCH$_2$-N$^{\oplus}$(3-NHAc-pyridinium) | 1770, 1700, 1670, 1605 |
| " | -N=CHCH$_2$-N$^{\oplus}$(2-Me-pyridinium) | 1775, 1710, 1670, 1615 |

TABLE 17-continued

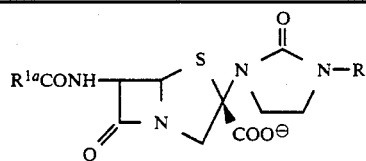

| $R^{1a}$ | R | IR(KBr) cm$^{-1}$: |
|---|---|---|
| HO—C₆H₄—CH(D)(NH—C(=O)—N-piperazine-2,3-dione-N'-Et) | —N=CHCH₂—N⁺(3-Me-pyridinium) | 1775, 1710, 1670, 1620 |
| " | —N=CHCH₂—N⁺(quinuclidinium) | 1770, 1710, 1670, 1620 |
| " | —N=CHCH₂—N⁺(1-Me-pyrrolidinium) | 1770, 1710, 1670, 1620 |
| " | —N=CHCH₂—N⁺(4-Me-imidazolium) | 1770, 1710, 1670, 1615 |
| " | —N=CHCH₂—N⁺(4-CONH₂-pyridinium) | 1780, 1710, 1675, 1620 |
| " | —N=CHCH₂—N⁺(4-NHCH₂CH₂OH-pyridinium) | 1770, 1705, 1670, 1605 |
| " | —N=CHCH₂—N⁺(3-NH₂-pyridinium) | 1770, 1720, 1670, 1620, 1600 |
| HO—C₆H₄—CH(D)(NH—C(=O)—N-piperazine-2,3-dione-N'-Et) | —N=CHCH₂—N⁺(6,7-diOH-tetrahydroisoquinolinium) | 1770, 1710, 1670, 1620 |
| " | —N=CHCH₂—N⁺(2-Me,1-Me-imidazolinium) | 1770, 1750, 1665, 1610 |

TABLE 17-continued

[Structure: R¹ᵃCONH-[β-lactam-thiazolidine core]-N(C=O)N-R with COO⁻]

| R¹ᵃ | R | IR(KBr) cm⁻¹: |
|---|---|---|
| " | −N=CHCH₂−N⊕(pyrrolidine)−N(Me)₂ (on pyridine with NMe₂) | 1775, 1710, 1670, 1650, 1610 |
| " | −N=CHCH₂−N⊕ N-n-Pr | 1770, 1710, 1670, 1610 |
| " | −N=CHCH₂−N⊕ NCH₂CO₂Na | 1770, 1710, 1670, 1615 |
| " | −N=CHCH₂−N⊕ N−Et | 1770, 1710, 1670, 1610 |
| AcO,AcO-phenyl-CH(D)-NH-C(=O)-N(2,3-dioxopiperazine)-N-Et | −N=CHCH₂−N⊕(piperidine) | 1780, 1720, 1680, 1620 |
| " | −N=CHCH₂−N⊕ N−Me | 1770, 1710, 1670, 1610 |
| phenyl-CH(D)-NH-C(=O)-N(2,3-dioxopiperazine)-N-Et | " | 1775, 1710, 1670, 1620 |
| aminothiazolyl-CH(DL)-NH-C(=O)-N(2,3-dioxopiperazine)-N-Et | −N=CHCH₂−N⊕(piperidine) | 1770, 1710, 1670, 1620 |

EXAMPLE 20

(1) 250 mg of p-acetoxyphenylacetic acid was dissolved in 5 ml of methylene chloride. To the solution were added, with ice cooling, a catalytic amount of N,N-dimethylformamide and 0.12 ml of oxalyl chloride. The mixture was stirred at room temperature for 1 hour. The reaction mixture was concentrated under reduced pressure to obtain p-acetoxyphenylacetyl chloride. This compound was dissolved in 5 ml of methylene chloride. To the solution was added 260 mg of a sulfur trioxide-dioxane complex with ice cooling. The mixture was stirred at room temperature for 2 hours. The solvent was removed by distillation under reduced pressure to obtain DL-2-(p-acetoxyphenyl)-2-sulfoacetyl chloride. This compound was dissolved in 5 ml of anhydrous tetrahydrofuran.

(2) In a mixed solvent consisting of 5 ml of tetrahydrofuran and 5 ml of water was dissolved 300 mg of (3R,5R,6R)-6-amino-3-(p-nitrobenzyloxycarbonyl)-7-oxo-3-(2-oxo-3-ureidoimidazolidin-1-yl)-4-thia-1-azabicyclo[3.2.0]heptane. To this solution was dropwise added the tetrahydrofuran solution of DL-2-(p-acetoxyphenyl)-2-sulfoacetyl chloride prepared in (1) above, with ice-cooling while maintaining the pH at 7.0 to 7.5 with a saturated aqueous sodium hydrogencarbonate solution. After the dropwise addition, the mixture was stirred at the same temperature for 10 minutes. To the mixture was added 5 ml of ethyl acetate, and adjusted to pH 6.0 with 1N hydrochloric acid. The aqueous layer was separated. Water was removed by distillation under reduced pressure. The residue was purified by reversed phase column chromatography (eluent: water/acetonitrile=1/0 to 9/1) to obtain 340 mg (yield: 70.8%) of sodium salt of (3R,5R,6R)-6-[DL-α-(p-acetoxyphenyl)-α-sulfoacetamido]-3-(p-nitrobenzyloxycarbonyl)-7-oxo-3-(2-oxo-3-ureidoimidazolidin-1-yl)-4-thia-1-azabicyclo[3.2.0]heptane.

IR (KBr) cm$^{-1}$: 1775, 1720, 1670

The compounds shown in Table 18 were obtained in the same manner.

In Table 18, R$^{1a}$ and R each show a substituent of the following formula.

TABLE 18

| R$^{1a}$ | R | IR (KBr) cm$^{-1}$: |
|---|---|---|
| Ph-CH(SO$_3$Na)- (DL) | -NHC(=O)NH$_2$ | 1770, 1710, 1660, 1620 |
| " | -N=CH-(furyl) | — |
| " | -N=C(1,3-dithiolane) | — |
| (AcO)$_2$C$_6$H$_3$-CH(SO$_3$Na)- (DL) | " | — |
| " | -NHC(=O)NH$_2$ | 1770, 1715, 1670 |
| (AcO)$_2$-C$_6$H$_2$(Cl)-CH(SO$_3$Na)- (DL) | " | 1770, 1710, 1670, 1620 |
| NO$_2$-C$_6$H$_4$-CH(SO$_3$Na)- (DL) | -NHC(=O)NH$_2$ | — |

TABLE 18-continued

| $R^{1a}$ | R | IR (KBr) cm$^{-1}$: |
|---|---|---|
| 3-F, 4-AcO-C$_6$H$_3$-CH(SO$_3$Na)- (DL) | " | 1770, 1725, 1670 |
| 3,4-(AcO)$_2$-5-Cl-C$_6$H$_2$-CH(SO$_3$Na)- (DL) | " | 1770, 1720, 1670 |
| 3-AcO-C$_6$H$_4$-CH(SO$_3$Na)- (DL) | " | 1775, 1730, 1675 |
| 2-Cl, 5-O$_2$N-C$_6$H$_3$-CH(SO$_3$Na)- (DL) | " | 1780, 1725, 1685 |
| 3-F, 4-AcO, 5-Cl-C$_6$H$_2$-CH(SO$_3$Na)- (DL) | " | 1780, 1720, 1680 |
| 3-F, 4-AcO-C$_6$H$_3$-CH(SO$_3$Na)- (DL) | -NHC(=O)NH$_2$ | 1770, 1720, 1670 |
| 3-F, 4,5-(AcO)$_2$-C$_6$H$_2$-CH(SO$_3$Na)- (DL) | " | 1770, 1720, 1680 |
| 2-Cl-C$_6$H$_4$-CH(SO$_3$Na)- (DL) | " | 1775, 1725, 1670 |
| 2-aminothiazol-5-yl-CH(SO$_3$Na)- (DL) | " | 1770, 1705, 1660, 1600 |

TABLE 18-continued

Structure: R¹ᵃCONH-[β-lactam-thia-imidazolidinone]-N-R with COOPNB

| R¹ᵃ | R | IR (KBr) cm⁻¹ |
|---|---|---|
| 3,4-diAcO-2,5-diCl-C₆H-CH(SO₃Na)- (DL) | " | 1780, 1720, 1670 |
| 3-F-4,5-diAcO-C₆H₂-CH(SO₃Na)- (DL) | " | 1760, 1720, 1705, 1675 |

EXAMPLE 21

(3R,5R)-6-amino-3-(3-benzylideneamino-2-oxoimidazolidin-1-yl)-6-methoxy-3-(p-nitrobenzyloxycarbonyl)-7-oxo-4-thia-1-azabicyclo[3.2.0]heptane was reacted with DL-α-(p-nitrobenzyloxycarbonyl)-α-phenylacetic acid in place of (3R,5R,6R)-6-amino-3-(p-nitrobenzyloxycarbonyl)-7-oxo-3-(2-oxo-3-ureidoimidazolidin-1-yl)-4-thia-1-azabicyclo[3.2.0]heptane in the same manner as in Example 20 to obtain (3R,5R,6R)-3-(3-benzylideneamino-6-[DL-α-(p-nitrobenzyloxycarbonyl)-α-phenylacetamido]-7-oxo-4-thia-1-azabicyclo[3.2.0]heptane.

IR (KBr) cm⁻¹: 1780, 1740, 1710, 1690

EXAMPLE 22

10 ml of water was added to 150 mg of 5% palladium-carbon and 330 mg of sodium salt of (3R,5R,6R)-6-[DL-α-(p-acetoxyphenyl)-α-sulfoacetamido]-3-(p-nitrobenzyloxycarbonyl)-7-oxo-3-(2-oxo-3-ureidoimidazolidin-1-yl)-4-thia-1-azabicyclo[3.2.0]heptane. The mixture was stirred at room temperature for 2 hours in a hydrogen atmosphere. The insolubles were removed by filtration. 10 ml of ethyl acetate was added to the filtrate, and the mixture was adjusted to pH 6.0 with a saturated aqueous sodium hydrogencarbonate solution. The aqueous layer was separated. Water was removed by distillation under reduced pressure. The residue was purified by reversed phase column chromatography (eluant: water) and freeze-dried to obtain 210 mg (yield: 47.1%) of disodium salt of (3R,5R,6R)-6-[DL-α-(p-acetoxyphenyl)-α-sulfoacetamido]-3-carboxy-7-oxo-3-(2-oxo-3-ureidoimidazolidin-1-yl)-4-thia-1-azabicyclo[3.2.0]heptane.

IR (KBr) cm⁻¹: 1760, 1710, 1670, 1610

The compounds shown in Table 19 were obtained in the same manner.

In Table 19, R¹ᵃ and R each show a substituent of the following formula.

TABLE 19

Structure: R¹ᵃCONH-[β-lactam-thia-imidazolidinone]-N-R with COONa

| R¹ᵃ | R | IR(KBr) cm⁻¹ |
|---|---|---|
| C₆H₅-CH(SO₃Na)- (DL) | -NHCNH₂ (C=O) | 1770, 1710, 1660, 1620 |
| " | -N=CH-(2-furyl) | 1770, 1660, 1620 |
| " | -N=C(1,3-dithiolan-2-ylidene) | 1770, 1670, 1620 |
| 3,4-diAcO-C₆H₃-CH(SO₃Na)- (DL) | " | 1760, 1660, 1620 |
| " | -NHCNH₂ (C=O) | 1760, 1705, 1670, 1615 |
| 3,4-diAcO-5-Cl-C₆H₂-CH(SO₃Na)- (DL) | " | 1770, 1710, 1670, 1620 |

TABLE 19-continued

Structure:
R$^{1a}$CONH-[β-lactam-thiazolidine spiro imidazolidinone]-N-R, with COONa, showing 2-oxo-imidazolidine with N-R

| R$^{1a}$ | R | IR(KBr) cm$^{-1}$: |
|---|---|---|
| 4-NH$_2$-C$_6$H$_4$-CH(SO$_3$Na)- (DL) | -NHCNH$_2$ (C=O) | 1770, 1710, 1670, 1620 |
| 3-AcO-4-F-C$_6$H$_3$-CH(SO$_3$Na)- (DL) | " | 1765, 1705, 1670, 1620 |
| 3,4-(AcO)$_2$-5-Cl-C$_6$H$_2$-CH(SO$_3$Na)- (DL) | " | 1760, 1665, 1615 |
| 3-AcO-C$_6$H$_4$-CH(SO$_3$Na)- (DL) | " | 1760, 1700, 1670, 1615 |
| 3-H$_2$N-4-Cl-C$_6$H$_3$-CH(SO$_3$Na)- (DL) | " | 1765, 1710, 1670, 1620 |
| 3-Cl-4-AcO-5-F-C$_6$H$_2$-CH(SO$_3$Na)- (DL) | " | 1775, 1710, 1675, 1620 |
| 3-AcO-4-F-C$_6$H$_3$-CH(SO$_3$Na)- (DL) | -NHCNH$_2$ (C=O) | 1760, 1700, 1670, 1610 |
| 3,5-(AcO)$_2$-4-F-C$_6$H$_2$-CH(SO$_3$Na)- (DL) | " | 1760, 1710, 1670, 1620 |
| 2-Cl-C$_6$H$_4$-CH(SO$_3$Na)- (DL) | " | 1765, 1705, 1665, 1615 |
| 2-aminothiazol-4-yl-CH(SO$_3$Na)- (DL) | " | 1770, 1710, 1670, 1610 |
| 3,4-Cl$_2$-5-AcO-6-AcO-C$_6$H-CH(SO$_3$Na)- (DL) | " | 1770, 1720, 1700, 1670, 1610 |
| 3,5-(AcO)$_2$-4-F-C$_6$H$_2$-CH(SO$_3$Na)- (DL) | " | 1770, 1710, 1675, 1620 |

EXAMPLE 23

In 5 ml of water was dissolved 200 mg of disodium salt of (3R,5R,6R)-3-(3-amino-2-oxoimidazolidin-1-yl)-3-carboxy-6-(DL-α-carboxy-α-phenylacetamido)-7-oxo-4-thia-1-azabicyclo[3.2.0]heptane. To the solution were added 0.5 ml of 1N hydrochloric acid and 31 mg of sodium cyanate. The mixture was stirred at room temperature for 30 minutes and adjusted to pH 6.5 with a saturated aqueous sodium hydrogencarbonate solution. The reaction mixture was concentrated under reduced pressure. The residue was purified by reversed phase column chromatography (eluant: water) and freeze-dried to obtain 160 mg (yield: 73.7%) of disodium salt of (3R,5R,6R)-3-carboxy-6-(DL-α-carboxy-α-phenylacetamido)-3-(2-oxo-3-ureidoimidazolidin-1-yl)-4-thia-1-azabicyclo[3.2.0]heptane.

IR (KBr) cm$^{-1}$: 1760, 1705, 1660, 1600

NMR (D$_2$O) δ: 3.60 (4H, s), 5.48–5.64 (2H, m), 7.40 (5H, s)

The compounds shown in Table 20 were obtained in the same manner.

In Table 20, R$^{1a}$ shows a substituent of the following formula.

TABLE 20

Structure: R¹ᵃCONH—[β-lactam-thiazolidine spiro]—N—NHCNH₂ with COONa and C=O groups

| R¹ᵃ | IR(KBr)cm⁻¹: |
|---|---|
| HO—C₆H₄—CH(D)(NH)—C(=O)—N—[piperazine-2,3-dione]—N-Et | 1770, 1710, 1670, 1605 |
| 2-aminothiazol-4-yl—C(=N—O—C(Me)₂—CO₂Na)— | 1770, 1700, 1660, 1580 |
| HO—C₆H₄—CH(DL)(CO₂Na)— | 1765, 1700, 1660, 1590 |
| H₂NC(O)—C₆H₄—CH(DL)(CO₂Na)— | 1770, 1730, 1670, 1600 |
| thien-2-yl—CH(DL)(CO₂Na)— | 1760, 1710, 1660, 1600 |
| F—C₆H₄—CH(DL)(CO₂Na)— | 1765, 1710, 1660, 1600 |
| 2-Cl—C₆H₄—CH(DL)(CO₂Na)— | 1770, 1710, 1665, 1600 |

EXAMPLE 24

The compounds shown in Table 21 were obtained in the same manner as in Example 23.

In Table 21, R and R¹ᵃ each show a substituent of the following formula.

TABLE 21

Structure: R¹ᵃCONH—[β-lactam-thiazolidine spiro]—N—R with COONa and C=O groups

| R¹ᵃ | R | IR(KBr) cm⁻¹: |
|---|---|---|
| (DL) 2-Cl-4,5-di-HO-C₆H₂—CH(SO₃Na)— | —NHCONH₂ | — |
| (D) 2-Cl-4,5-di-HO-C₆H₂—CH(SO₃Na)— | ″ | 1765, 1700–1660, 1620 |

EXAMPLE 25

In 2 ml of N,N-dimethylformamide were dissolved 53 mg of 1,4-dihydro-5-hydroxy-4-oxo-2-pyridinecarboxylic acid, 40 mg of N-hydroxysuccinimide and 71 mg of N,N'-dicyclohexylcarbodiimide. The solution was stirred at room temperature for 2 hours. To the reaction mixture were added 150 mg of (3R,5R,6R)-6-(D-α-amino-α-phenylacetamido)-3-carboxy-3-[3-(1,3-dithiolan-2-ylideneamino)-2-oxoimidazolidin-1-yl]-7-oxo-4-thia-1-azabicyclo[3.2.0]heptane and 0.06 ml of triethylamine in this order. The mixture was stirred at room temperature for 2 hours. The insolubles were removed by filtration. The solvent was removed by distillation under reduced pressure. To the residue were added 15 ml of ethyl acetate and 10 ml of water. The mixture was adjusted to pH 7.0 with a saturated aqueous sodium hydrogencarbonate solution. The aqueous layer was separated. Water was removed by distillation under reduced pressure. The residue was purified by reversed phase column chromatography (eluant: water/acetonitrile=1/0 to 9/1) and freeze-dried to obtain 35 mg (yield: 17.9%) of sodium salt of (3R,5R,6R)-3-[3-(1,3-dithiolan-2-ylideneamino)-2-oxoimidazolidin-1-yl]-3-carboxy-6-{D-α-[(5-hydroxy-4-oxo-1,4-dihydropyridin-2-yl)carboxamido]-α-phenylacetamido}-7-oxo-4-thia-1-azabicyclo[3.2.0]heptane.

IR (KBr) cm$^{-1}$: 1770, 1710, 1660, 1610

The compounds shown in Table 22 were obtained in the same manner.

In Table 22, R$^{1a}$ shows a substituent of the following formula.

Note:
*A reaction was effected in hydrous tetrahydrofuran using (a) (4-ethyl-2,3-dioxo-1-piperazine)-carbonyl chloride in place of 5-hydroxy-4-oxo-1,4-dihydro-2-pyridinecarboxylic acid and (b) sodium hydrogencarbonate by Shotten-Baumann method.

EXAMPLE 26

In 20 ml of water was dissolved 100 mg of disodium salt of (3R,5R,6R)-6-[DL-α-(p-acetoxyphenyl)sulfoacetamido]-3-carboxy-7-oxo-3-(2-oxo-3-ureidoimidazolidin-1-yl)-4-thia-1-azabicyclo[3.2.0]heptane. The solution was adjusted to pH 6.8 with a saturated aqueous sodium hydrogencarbonate solution. Thereto was added, with ice cooling, 20 mg of an esterase (manufactured by Boehringer Mannheim) which had been desalted using a continuous counter current dialyzer (Zeineh Dialyzer manufactured by Funakoshi Co.). The mixture was stirred at 35° C. for 4 hours while maintaining the reaction mixture at pH 6.5 to 6.8 with a saturated aqueous sodium hydrogencarbonate solution. The reaction mixture was subjected to ultrafiltration using a hollow fiber membrane (membrane type: HI, manufactured by ASAHI CHEMICAL INDUSTRY, CO., LTD.). The filtrate was adjusted to pH 5.0 with 0.1N hydrochloric acid. The solvent was removed by distillation under reduced pressure. The residue was purified by reversed phase column chromatography (eluant: water) and freeze-dried to obtain 62.5 mg (yield: 67.0%) of disodium salt of (3R,5R,6R)-3-carboxy-6-[DL-α-(p-hydroxyphenyl)-α-sulfoacetamido]-7-oxo-3-(2-oxo-3-ureidoimidazolidin-1-yl)-4-thia-1-azabicyclo[3.2.0]heptane.

IR (KBr) cm$^{-1}$: 1760, 1705, 1665, 1600

The compounds shown in Table 23 were obtained in the same manner.

In Table 23, R$^{1a}$ shows a substituent of the following formula.

TABLE 23

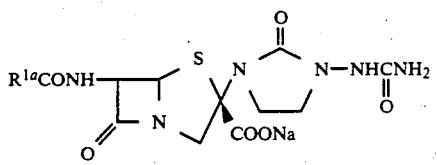

| R$^{1a}$ | | IR(KBr)cm$^{-1}$: |
|---|---|---|
| Cl-C6H2(OH)-CH(SO3Na)- | (L) | 1770, 1720, 1660, 1600 |
| | (D) | 1770, 1670, 1610 |
| HO-C6H4-CH(SO3Na)- | (D) | 1770, 1700, 1670, 1620 |
| F-C6H3(OH)-CH(SO3Na)- | (L) | 1770, 1700, 1670, 1620 |
| | (D) | 1765, 1700, 1670, 1620 |
| F-C6H3(OH)-CH(SO3Na)- | (L) | 1770, 1700, 1660, 1620 |
| | (D) | 1765, 1700, 1670, 1620 |
| HO-C6H3(OH)-CH(SO3Na)- | (D) | 1770, 1720, 1670, 1610 |

TABLE 23-continued

| R$^{1a}$ | | IR(KBr)cm$^{-1}$: |
|---|---|---|
| Cl-C6H2(OH)2-CH(SO3Na)- | (L) | 1770, 1720, 1670, 1615 |
| | (D) | 1765, 1700–1660, 1620 |
| | (DL) | 1765, 1720, 1700, 1670, 1620 |
| Cl-C6H2(OH)(OMe)-CH(SO3Na)- | (D) | 1765, 1700, 1665, 1610 |

EXAMPLE 27

In the same manner as in Example 26, there was obtained disodium salt of (3R,5R,6R)-3-carboxy-6--[D-α-(2-chloro-4,5-dihydroxyphenyl)-α-sulfoacetamido]-7-oxo-3-(2-oxo-3-semicarbazonoethylideneaminoimidazolidin-1-yl)-4-thia-1-azabicyclo[3.2.0]heptane.

IR (KBr) cm$^{-1}$: 1765, 1720, 1700, 1670, 1620

EXAMPLE 28

In 664 ml of methylene chloride was dissolved 83.0 g of (3R,5R,6R)-3-(3-benzylideneamino-2-oxo-imidazolidin-1-yl)-3-diphenylmethyloxycarbonyl-7-oxo-6-phenylacetamido-4-thia-1-azabicyclo[3.2.0]heptane.

The solution was cooled to −60° C. To the solution were added 55.8 ml of N,N-dimethylaniline and 39.3 g of phosphorus pentachloride in this order. The temperature of the mixture was elevated to −20° C. in 30 minutes and then recooled to −60° C. To the reaction mixture was added 66.3 ml of anhydrous methanol, and the mixture was heated to 0° C. in 30 minutes and stirred at the same temperature for 30 minutes. 664 ml of ethyl acetate was added to the reaction mixture. The mixture was stirred for 15 minutes with ice cooling. The resulting crystals were collected by filtration, washed twice each with 83 ml of methylene chloride and once with 83 ml of ethyl acetate, and dried under reduced pressure to obtain 57.5 g (yield: 79.0%) of (3R,5R,6R)-6-amino-3-(3-benzylideneamino-2-oxoimidazolidin-1-yl)-3-diphenylmethyloxycarbonyl-7-oxo-4-thia-1-azabicyclo[3.2.0]heptane hydrochloride.

IR (KBr) cm$^{-1}$: 1790, 1720, 1705

The compounds shown in Table 24 were obtained in the same manner.

In Table 24, R and R$^{14}$ each show a substituent of the following formula.

TABLE 24

| | R | R¹⁴ | IR(KBr) cm⁻¹: |
|---|---|---|---|
| | —N=CH—⟨C₆H₄⟩—Me | DPM | 1790, 1725, 1710 |
| | —N=CH—⟨C₆H₄⟩—OMe | " | 1790, 1725, 1710 |
| | —N=⟨dithiolane⟩ | PNB | 1790, 1710 |

Structure (Table 24): HCl·H₂N—[β-lactam-thia-bicyclic]—N(C=O)N—R with COOR¹⁴

EXAMPLE 29

(1) 60.0 g of (3R,5R,6R)-6-amino-3-(3-benzylideneamino-2-oxoimidazolidin-1-yl)-3-diphenylmethyloxycarbonyl-7-oxo-4-thia-1-azabicyclo[3.2.0]heptane hydrochloride was suspended in a mixed solvent consisting of 450 ml of methylene chloride, 63 ml of anisole and 80 ml of nitromethane. The suspension was cooled to −30° C.

(2) 31.8 g of anhydrous aluminum chloride was dissolved in 70 ml of nitromethane. The solution was dropwise added to the suspension prepared in (1) above, at −30° C. The mixture was stirred at −20° C. for 10 minutes. The reaction mixture was poured into 1.2 liters of 1.5N hydrochloric acid. The mixture was stirred for 30 minutes at room temperature and adjusted to pH 1.5 with a 20% aqueous sodium carbonate solution. The resulting precipitate was collected by filtration and suspended in 2.4 liters of water. The suspension was adjusted to pH 9.0 with concentrated ammonia water. The insolubles were removed by filtration with Celite. The filtrate was washed with 500 ml of ethyl acetate, adjusted to pH 3.5 with 6N hydrochloric acid, and stirred for 15 minutes with ice cooling. The resulting crystals were collected by filtration and dried to obtain 36.0 g (yield: 92.0%) of (3R,5R,6R)-6-amino-3-(3-benzylideneamino-2-oxoimidazolidin-1-yl)-3-carboxy-7-oxo-4-thia-1-azabicyclo[3.2.0]heptane.

IR (KBr) cm⁻¹: 1780, 1705, 1640

The compounds shown in Table 25 were obtained in the same manner.

In Table 25, R shows a substituent of the following formula.

TABLE 25

| R | IR(KBr) cm⁻¹: |
|---|---|
| —N=CH—⟨C₆H₄⟩—Me | 1780, 1710, 1640 |
| —N=CH—⟨C₆H₄⟩—OMe | 1780, 1710, 1640 |

Structure (Table 25): H₂N—[β-lactam-thia-bicyclic]—N(C=O)N—R with COOH

EXAMPLE 30

In 150 ml of methanol was suspended 10.0 g of (3R,5R,6R)-6-amino-3-(3-benzylideneamino-2-oxoimidazolidin-1-yl)-3-carboxy-7-oxo-4-thia-1-azabicyclo[3.2.0]heptane. Thereto was added 9.2 g of 2,4-dinitrophenylhydrazine hydrochloride at 20°-25° C. The mixture was stirred at the same temperature for 3 hours. 100 ml of water was added to the reaction mixture. The mixture was adjusted to pH 8.0 with concentrated ammonia water. The resulting crystals were removed by filtration. To the filtrate was slowly added concentrated hydrochloric acid to adjust the filtrate to pH 1.5. To the filtrate was added 2.5 g of active carbon, and the mixture was stirred at room temperature for 5 minutes. The active carbon was removed by filtration and washed with water. The filtrate and washings were combined and to the resulting mixture was added 3.9 g of sodium cyanate at room temperature in 60 minutes while maintaining the reaction mixture at pH 1.6 to 2.1 with concentrated hydrochloric acid. After the addition, the mixture was stirred at room temperature for 60 minutes. The resulting crystals were collected by filtration and suspended in 50 ml of water. To the suspension was added concentrated ammonia water to adjust the suspension to pH 9.0. Then, 0.4 g of active carbon was added, and the mixture was stirred at room temperature for 5 minutes. The active carbon was removed by filtration and washed with water. Concentrated hydrochloric acid was added to a mixture of the washings and the previously obtained filtrate to adjust the pH to 4.5. The mixture was stirred at room temperature for 30 minutes. The resulting crystals were collected by filtration, washed with water and acetone in this order, and dried under reduced pressure to obtain 5.81 g (yield: 66.0%) of (3R,5R,6R)-6-amino-3-carboxy-7-oxo-3-(2-oxo-3-ureidoimidazolidin-1-yl)-4-thia-1-azabicyclo[3.2.0]heptane.

IR (KBr) cm⁻¹: 1770, 1710, 1660, 1620

(3R,5R,6R)-6-amino-3-carboxy-3-[3-(p-methylbenzylideneamino)-2-oxoimidazolidin-1-yl-]-7-oxo-4-thia-1-azabicyclo[3.2.0]heptane and (3R,5R,6R)-6-amino-3-(3-anisylideneamino-2-oxoimidazolidin-1-yl)-3-carboxy-7-oxo-4-thia-1-azabicyclo[3.2.0]heptane were treated in the same manner to obtain (3R,5R,6R)-6-amino-3-carboxy-7-oxo-3-(2-oxo-3-ureidoimidazolidin-1-yl)-4-thia-1-azabicyclo[3.2.0]heptane. The physical property (IR) of this product were identical with that obtained above.

EXAMPLE 31

In 80 ml of methylene chloride was dissolved 7.50 g of (3R,5R,6R)-6-amino-3-(3-benzylideneamino-2-oxoimidazoldin-1-yl)-3-diphenylmethyloxycarbonyl-7-oxo-4-thia-1-azabicyclo[3.2.0]heptane. Thereto was added 5 g of S-p-methoxybenzyloxycarbonyl-4,6-dimethyl-2-mercaptopyrimidine. The mixture was stirred at room temperature for 2 hours. The reaction mixture was mixed with 80 ml of water, and the resulting mixture was adjusted to pH 7.0 with a saturated aqueous sodium hydrogencarbonate solution. The organic layer was separated, washed with water and a saturated aqueous sodium chloride solution in this order, and dried over anhydrous magnesium sulfate. The solvent was removed by distillation under reduced pressure. The organic layer was separated, washed with water and a saturated aqueous sodium chloride solution in this order, and dried over anhydrous magnesium sulfate. The solvent was removed by distillation under reduced pressure. The residue was purified by column chromatography (eluant: chloroform/acetone=20/1 to 10/1) to obtain 0.15 g (yield: 72.1%) of (3R,5R,6R)-3-(p-nitrobenzyloxycarbonyl)-6-[DL-α-(p-nitrobenzyloxycarbonyl)-α-phenylacetamido]-3-[3-(N-methoxyiminoethylideneamino)-2-oxoimidazolidin-1-yl]-7-oxo-4-thia-1-azabicyclo[3.2.0]heptane.

IR (KBr) cm$^{-1}$: 1790, 1710

The compounds shown in Table 26 were obtained in the same manner.

In Table 26, R$^{1a}$ and R each show a substituent of the following formula.

TABLE 26

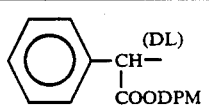

| R$^{1a}$ | R | IR(KBr)cm$^{-1}$: |
|---|---|---|
| 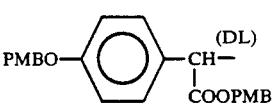 (DL) | —N=CHCH=NOCH$_2$CO$_2$DPM | 1785, 1725, 1670 |
|  (DL) | —N=CHCH=NNHCONH$_2$ | 1780, 1720, 1680 |
| " | —N=CHCH=NNHCHO | 1790, 1730, 1680 |
| " | 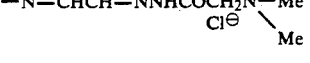 | 1780, 1720, 1680 |
| " | —N=CHCH=NNHCNH$_2$<br>‖<br>NH | 1790, 1740, 1680 |
| PMB—O— | —N=CHCH=NNHCONH$_2$ | 1785, 1730, 1720, 1690 | sure. The residue was purified by column chromatography (eluant: chloroform/acetone=1/0 to 25/1) to obtain 8.36 g (yield: 85.2%) of (3R,5R,6R)-3-(3-benzylideneamino-2-oxoimidazolidin-1-yl)-3-diphenylmethyloxycarbonyl-6-(p-methoxybenzyloxycarbonylamino)-7-oxo-4-thia-1-azabicyclo[3.2.0]heptane.

IR (KBr) cm$^{-1}$: 1795, 1710

EXAMPLE 32

In a mixed solvent consisting of 10 ml of methylene chloride and 10 ml of methanol was dissolved 0.20 g of (3R,5R,6R)-3-(3-formylmethylideneamino-2-oxoimidazolidin-1-yl)-3-(p-nitrobenzyloxycarbonyl)-6-[DL-α-(p-nitrobenzyloxycarbonyl]-α-phenylacetamido]-7-oxo-4-thia-1-azabicyclo[3.2.0]heptane. Thereto was added 26 mg of methoxyamine hydrochloride. The mixture was stirred at room temperature for 1 hour. The reaction mixture was mixed with 10 ml of water. The resulting mixture was adjusted to pH 7 with a saturated aqueous sodium hydrogencarbonate

EXAMPLE 33

In 7 ml of methylene chloride was dissolved 0.70 g of (3R,5R,6R)-3-(3-amino-2-oxoimidazolidin-1-yl)-3-diphenylmethyloxycarbonyl-6-{DL-α-(p-methoxybenzyloxycarbonyl)-α-[4-(p-methoxybenzyloxy)phenyl]acetamido}-7-oxo-4-thia-1-azabicyclo[3.2.0]heptane. The solution was cooled to −30° C. and mixed with 0.085 ml of chlorosulfonyl isocyanate. The mixture was stirred for 30 minutes with ice cooling. Then, 0.2 ml of a 16% ammonia-methanol solution was added to the reaction mixture with ice cooling, and the resulting mixture was stirred at the same temperature for 30 minutes. 5 ml of water was added to the reaction mixture. The resulting mixture was adjusted to pH 2 with 1N hydrochloric acid. The organic layer was separated and dried over anhydrous magnesium sulfate. The solvent was removed by distillation under reduced pressure.

The residue was purified by column chromatography (eluant: chloroform/methanol=30/1 to 10/1) to obtain 0.60 g (yield: 77.7%) of (3R,5R,6R)-3-[3-(3-aminosulfamoylureido)-2-oxo-imidazolidin-1-yl]-3-diphenylmethyloxycarbonyl-6-{DL-α-(p-methoxybenzyloxycarbonyl)-α-[4-(p-methoxybenzyloxy)phenyl]acetamido}-7-oxo-4-thia-1-azabicyclo[3.2.0]heptane.

IR (KBr) cm$^{-1}$: 1790, 1710

EXAMPLE 34

In 5 ml of benzene was dissolved 0.23 g of (3R,5R,6R) 3-diphenylmethyloxycarbonyl-6-(DL-α-diphenylmethyloxycarbonyl-α-phenylacetamido)-3-(3-formylmethylideneamino-2-oxoimidazolidin-1-yl)-7-oxo 4-thia-1-azabicyclo[3.2.0]heptane. Thereto was added 0.12 9 of triphenylphosphoranylideneacetonitrile. The mixture was stirred at room temperature for 2 days. The reaction mixture was mixed with 10 ml of water and 10 ml of ethyl acetate. The mixture was adjusted to pH 7 with a saturated aqueous sodium hydrogencarbonate solution. The organic layer was separated and dried over anhydrous magnesium sulfate. The solvent was removed by distillation under reduced pressure. The residue was purified by column chromatography (eluant: benzene/ethyl acetate=3/1 to 2/1) to obtain 0.10 g (yield: 42.4%) of (3R,5R,6R)-3-[3-(3-cyano-2-propenylideneamino)-2-oxoimidazolidin-1-yl]-3-diphenylmethyloxycarbonyl-6-(DL-α-diphenylmethyloxycarbonyl-α-phenylacetamido)-7-oxo-4-thia-1-azabicyclo[3.2.0]heptane.

IR (KBr) cm$^{-1}$: 1790, 1710

The following compound was obtained in the same manner.

(3R,5R,6R)-3-diphenylmethyloxycarbonyl-6-[DL-α(diphenylmethyloxycarbonyl)-γ-p-methoxybenzyloxyphenylacetamido]-7-oxo-3-[2-oxo-3-(5-piperidinocarbonyl-2,4-pentadienylideneamino)imidazolidin-1-yl]-4-thia-1-azabicyclo[3.2.0]heptane IR (KBr) cm$^{-1}$: 1785, 1720, 1605

EXAMPLE 35

In 5 ml of methylene chloride was dissolved 320 mg of (3R,5R,6R)-6-[D-α-(p-acetoxyphenyl)-α-(p-methoxybenzyloxycarbonylamino)acetamido]-3-(p-nitrobenzyloxycarbonyl)-7-oxo-3-(2-oxo-3-ureidoimidazolidin-1-yl)-4-thia-1-azabicyclo[3.2.0]heptane. The solution was cooled to −20° C. Thereto was dropwise added 0.78 ml of an anisole solution containing 160 mg of anhydrous aluminum chloride at −20° to −10° C. After the dropwise addition, the mixture was stirred at −10° to 0° C. for 30 minutes. The reaction mixture was added to a mixed solvent consisting of 10 ml of water and 15 ml of ethyl acetate. The resulting mixture was adjusted to pH 1.0 with 2N hydrochloric acid. The aqueous layer was separated and mixed with 10 ml of ethyl acetate and 10 ml of tetrahydrofuran. The mixture was adjusted to pH 7.5 with a saturated aqueous sodium hydrogencarbonate solution. The insolubles were removed by filtration. The organic layer was separated, washed with a saturated aqueous sodium chloride solution, and dried over anhydrous magnesium sulfate. The solvent was removed by distillation under reduced pressure to obtain 140 mg (yield: 54 9%) of (3R,5R,6R)-6-[D-α-(p-acetoxyphenyl)-α-aminoacetamido]-3-(p-nitrobenzyloxycarbonyl)-7-oxo-3-(2-oxo-3-ureidoimidazolidin-1-yl)-4-thia-1-azabicyclo[3.2.0]heptane.

EXAMPLE 36

In 22 ml of methylene chloride was suspended 220 mg of (3R,5R,6R)-6-[D-α-(p-acetoxyphenyl)-α-aminoacetamido]-3-(p-nitrobenzyloxycarbonyl)-7-oxo-3-(2-oxo-3-ureidoimidazolidin-1-yl)-4-thia-1-azabicyclo[3.2.0]heptane. Thereto was added 110 mg of a sulfur trioxidepyridine complex at room temperature, and the mixture was stirred for 3 hours at the same temperature. The solvent was removed by distillation under reduced pressure. The residue was mixed with 15 ml of ethyl acetate and 15 ml of water. The mixture was adjusted to pH 7.0 with a saturated aqueous sodium hydrogencarbonate solution. The aqueous layer was separated and purified by reversed phase column chromatography (eluant: water/acetonitrile=1/0 to 10/1) to obtain 40 mg (yield: 15.7%) of sodium salt of (3R,5R,6R)-6-[D-α-(p-acetoxyphenyl)-αphenyl)-α-sulfoaminoacetamido]-3-(p-nitrobenzyloxycarbonyl)-7-oxo-3-(2-oxo-3-ureidoimidazolidin-1-yl)-4-thia-1-azabicyclo[3.2.0]heptane.

IR (KBr) cm$^{-1}$: 1770, 1710, 1670, 1600

EXAMPLE 37

In 5 ml of methylene chloride was dissolved 170 mg of (3R,5R,6R)-3-(3-carboxymethylideneamino-2-oxoimidazolidin-1-yl)-3-diphenylmethyloxycarbonyl-6-(DL-α-diphenylmethyloxycarbonyl-α-phenylacetamido)-7-oxo-4-thia-1-azabicyclo[3.2.0]heptane. The solution was cooled to −20° to −10° C. Thereto were added 0.034 ml of triethylamine and 0.023 ml of ethyl chlorocarbonate in this order. The mixture was stirred at −20° to −10° C. for 30 minutes. To the reaction mixture was added 0.14 ml of a 7.4N amm methanol solution at a temperature of −20° C. or below. The mixture was stirred for 1 hour with ice cooling. The reaction mixture was added to a mixed solvent consisting of 10 ml of methylene chloride and 10 ml of water. The resulting mixture was adjusted to pH 2.0 with 2N hydrochloric acid. The organic layer was separated, washed with a saturated aqueous sodium chloride solution, and dried over anhydrous magnesium sulfate. The solvent was removed by distillation under reduced pressure. The residue was purified by column chromatography (eluant: chloroform/acetone=10/1 to 2/1) carbamoylmethylideneamino-2-oxoimidazolidin-1-yl)-3-carbamoylmethyldieneamino-6-(DL-α-diphenylmethyloxycarbonyl-α-phenylacetamido)-7-oxo-4-thia-1-azabicyclo[3.2.0]heptane.

IR (KBr) cm$^{-1}$: 1780, 1720, 1670

The following compound was obtained in the same manner.

(3R,5R,6R)-3-[3-(3-carbamoyl-2-allylidene)amino-2-oxoimidazolidin-1-yl]-3-diphenylmethyloxycarbonyl-6-(DL-α-diphenylmethyloxycarbonyl-α-phenylacetamido)-7-oxo-4-thia-1-azabicyclo[3.2.0]heptane (KBr) cm$^{-1}$: 1790, 1730, 1670

EXAMPLE 38

In 10 ml of methylene chloride was dissolved 280 mg of (3R,5R,6R)-3-(3-carbamoylmethylideneamino-2-oxoimidazolidin-1-yl)-3-diphenylmethyloxycarbonyl-6-(DL-α-diphenylmethyloxycarbonyl-α-phenylacetamido)-7-oxo-4-thia-1-azabicyclo[3.2.0]heptane. Thereto were added 0.095 ml of trifluoroacetic anhydride and 0.108 ml of pyridine. The mixture was stirred at room temperature for 20 minutes. 5 ml of water was added to the reaction mixture. The mixture was adjusted to pH 3.0 with 1N hydrochloric acid. The organic layer was separated, washed with a saturated aqueous sodium chloride solution, and dried over anhydrous magnesium sulfate. The solvent was removed by distillation under reduced pressure. The residue was purified by column chromatography (eluant: chloroform/acetone=10/1 to 5/1) to obtain 110 mg (yield: 40.1%) of (3R,5R,6R)-3-(3-cyanomethylideneamino-2-oxoimidazolidin-1-yl)-3-diphenylmethyloxycarbonyl-6-(DL-α-diphenylmethyloxycarbonyl-α-phenylacetamido)-7-oxo-4-thia-1-azabicyclo[3.2.0]heptane.

EXAMPLE 39

(1) 6.0 g of DL-(4-acetoxy-2-chlorophenyl)acetic acid was suspended in 90 ml of methylene chloride. Thereto were added, with ice cooling, 2.75 ml of oxalyl chloride and 50 μl of N,N-dimethylformamide. The mixture was stirred at room temperature for 1 hour. The solvent was removed by distillation under reduced pressure. The residue was dissolved in 90 ml of methylene chloride. Thereto was added 5.30 g of a sulfur trioxide-dioxane complex with ice cooling. The mixture was stirred at room temperature overnight. The solvent was removed by distillation under reduced pressure. The residue was dissolved in 50 ml of anhydrous acetonitrile.

(2) In 100 ml of water was suspended 5.70 g of (3R,5R,6R)-6-amino-3-carboxy-7-oxo-3-(2-oxo-3-ureidoimidazolidin-1-yl)-4-thia-1-azabicyclo[3.2.0]heptane. Thereto was added a 20% aqueous sodium carbonate solution with ice cooling to adjust the pH to 9.0 to obtain a uniform solution. To the solution was added, in 40 minutes, the acetonitrile solution prepared in (1) above, with ice cooling while maintaining the reaction mixture at pH 7.0 to 7.5 with a 20% aqueous sodium carbonate solution. The mixture was stirred at the same temperature for 10 minutes. 50 ml of ethyl acetate was added thereto. The aqueous layer was separated, adjusted to pH 5.5 with 2N hydrochloric acid, and concentrated under reduced pressure. The residue was purified by reversed phase column chromatography (eluant: water) and freeze-dried to obtain each of isomers (diastereomers at 6-position) of disodium salt of (3R,5R,6R)-6-[α-(4-acetoxy-2-chlorophenyl)-α-sulfoacetamido]-3-carboxy-7-oxo-3-(2-oxo-3-ureidoimidazolidin-1-yl)-4-thia-1-azabicyclo[3.2.0]heptane.

L form [Eluted first in reversed phase column chromatography. 2.18 g (Yield: 20.0%)]

IR (KBr) cm$^{-1}$: 1765, 1700, 1690, 1670, 1620

D form [Eluted later in reversed phase column chromatography. 2.38 g (Yield: 21.8%)]

IR (KBr) cm$^{-1}$: 1765, 1700, 1685, 1670, 1620

The compounds shown in Table 27 were obtained in the same manner.

In Table 27, R$^{1a}$ shows a substituent of the following formula.

TABLE 27

| R$^{1a}$ | | IR(KBr)cm$^{-1}$: |
|---|---|---|
| phenyl-CH(SO$_3$Na)– | (L) | 1770, 1705, 1670, 1620 |
| | (D) | 1770, 1700, 1670, 1620 |
| 4-AcO-phenyl-CH(SO$_3$Na)– | (L) | 1760, 1700, 1670, 1620 |
| | (D) | 1760, 1700, 1670, 1620 |
| 3-AcO-phenyl-CH(SO$_3$Na)– | (L) | — |
| | (D) | 1765, 1720, 1700, 1665, 1610 |
| 4-O$_2$N-phenyl-CH(SO$_3$Na)– | (L) | 1770, 1720, 1705, 1665, 1620 |
| | (D) | 1760, 1705, 1685, 1605 |
| 4-AcO-2,5-diF-phenyl-CH(SO$_3$Na)– | (L) | 1765, 1720, 1700, 1670, 1610 |
| | (D) | — |
| 4-AcO-phenyl-CH(SO$_3$Na)– (4-F subst.) | (L) | 1760, 1700, 1670, 1620 |
| | (D) | 1760, 1705, 1670, 1620 |
| 4-AcO-3-Cl-phenyl-CH(SO$_3$Na)– | (L) | 1765, 1705, 1670, 1620 |
| | (D) | 1765, 1705, 1685, 1670, 1620 |
| 3,4-di-AcO-phenyl-CH(SO$_3$Na)– | (L) | 1765, 1700, 1670, 1620 |
| | (D) | 1765, 1710, 1680, 1670, 1620 |
| 4-AcO-3-O$_2$N-phenyl-CH(SO$_3$Na)– | (L) | 1770, 1710, 1690, 1670, 1620 |
| | (D) | 1760, 1705, 1690, 1670, 1620 |
| 3,4-di-AcO-2-Cl-phenyl-CH(SO$_3$Na)– | (L) | 1760, 1700, 1670, 1620 |
| | (D) | 1760, 1705, 1670, 1620 |

TABLE 27-continued

R¹ᵃCONH—[β-lactam-thiazolidine structure]—N—NHCNH₂ / COONa (with S, N, O arrangement)

| R¹ᵃ | | IR(KBr)cm⁻¹: |
|---|---|---|
| 4-F, 2-Cl, 5-AcO-C₆H₂-CH(SO₃Na)- | (L) | 1775, 1700, 1690, 1680, 1620 |
| | (D) | 1775, 1700, 1690, 1680, 1620 |
| 3,4-diAcO-C₆H₃-CH(SO₃Na)- | (L) | 1760, 1700, 1665, 1610 |
| | (D) | 1760, 1700, 1670, 1610 |
| 3,4-diCl-5-AcO-C₆H₂-CH(SO₃Na)- | (L) | 1770, 1705, 1690, 1670, 1620 |
| | (D) | 1770, 1705, 1690, 1670, 1610 |
| 3-Cl-4-AcO-5-MeO-C₆H₂-CH(SO₃Na)- | (L) | 1765, 1705, 1670, 1620 |
| | (D) | 1770, 1710, 1680, 1620 |
| 3-Cl-4-O₂N-C₆H₃-CH(SO₃Na)- | (L) | 1770, 1705, 1670, 1625 |
| | (D) | 1770, 1705, 1670, 1620 |
| C₆H₅-CH₂- | — | 1770, 1720, 1710, 1670, 1610 |

EXAMPLE 40

In a mixed solvent consisting of 15 ml of methylene chloride and 2.2 ml of anisole was suspended 1.5 g of (3R,5R,6R)-3-diphenylmethyloxycarbonyl-6-(p-methoxybenzyloxycarbonylamino)-7-oxo-3-[2-oxo-3-(2-semicarbazonoethylideneamino)imidazolidin-1-yl]-4-thia-1-azabicyclo[3.2.0]heptane. The suspension was cooled to −30° C. Thereto was added 7 ml of a nitromethane solution containing 1.4 g of anhydrous aluminum chloride. The mixture was stirred at −20° C. for 3 hours. 10 ml of water was added. The mixture was adjusted to pH 8.5 with a saturated aqueous sodium hydrogen carbonate solution. The precipitated insolubles were removed by filtration with Celite. The aqueous layer of the filtrate was separated. To the separated aqueous layer was added, in 20 minutes, 10 ml of an acetonitrile solution containing 1.23 g of DL-α-(4,5-diacetoxy-2-chlorophenyl)-α-sulfoacetyl chloride prepared in the same manner as in Example 39 (1), with ice cooling while maintaining the reaction mixture at pH 7 to 8 with a 20% aqueous sodium carbonate solution. The reaction mixture was then adjusted to pH 6 with 1N hydrochloric acid. Thereto was added 10 ml of ethyl acetate. The aqueous layer was separated and concentrated under reduced pressure. The residue was purified by reversed phase column chromatography (eluant: water/acetonitrile=20/1 to 10/1) to obtain each of diastereomers of (3R,5R,6R)-3-carboxy-6-[α-(4,5-diacetoxy-2-chlorophenyl)-α-sulfoacetamido]-7-oxo-3-[2-oxo-3-(2-semicarbazonoethylideneamino)imidazolidin-1-yl]-4-thia-1-azabicyclo[3.2.0]heptane.

L form [Eluted first in reversed phase column chromatography. 0.15 g (yield: 9.2%)]

IR (KBr) cm⁻¹: 1770, 1710, 1680, 1620

D form [Eluted later in reversed phase column chromatography. 0.20 g (yield: 12.3%)]

IR (KBr) cm⁻¹: 1765, 1710, 1680, 1620

EXAMPLE 41

In 10 ml of water was dissolved 460 mg of disodium salt of (3R,5R,6R)-3-carboxy-6-[D-α-(4-nitrophenyl)-α-sulfoacetamido]-7-oxo-3-(2-oxo-3-ureidoimidazolidin-1-yl)-4-thia-1-azabicyclo[3.2.0]heptane. Thereto was added 200 mg of 5% palladiumcarbon. The mixture was stirred at room temperature for 3 hours in a hydrogen atmosphere. After the completion of the reaction, the insolubles were removed by filtration and the filtrate was concentrated under reduced pressure. The residue was purified by reversed phase column chromatography (eluant: water) and freeze-dried to obtain 300 mg (yield: 68.5%) of disodium salt of (3R,5R,6R)-6-[D-α-(4-aminophenyl)-α-sulfoacetamido]-3-carboxy-7-oxo-3-(2-oxo-3-ureidoimidazolidin-1-yl)-4-thia-1-azabicyclo[3.2.0]heptane.

IR (KBr) cm⁻¹: 1770, 1700, 1660, 1615

The following compound was obtained in the same manner.

Disodium salt of (3R,5R,6R)-6-[D-α-(4-amino-2-chlorophenyl)-α-sulfoacetamido]-3-carboxy-7-oxo-3-(2-oxo-3-ureidoimidazolidin-1-yl)-4-thia-1-azabicyclo[3.2.0]heptane IR (KBr) cm⁻¹: 1765, 1705, 1660, 1620

EXAMPLE 42

In 5 ml of water was dissolved 150 mg of disodium salt of (3R,5R,6R)-6-[D-α-(4-aminophenyl)-αsulfoacetamido[-3-carboxy-7-oxo-3-(2-oxo-3-ureidoimidazolidin-1-yl)-4-thia-1-azabicyclo[3.2.0]heptane. Thereto was added 120 mg of sodium cyanate in small portions with ice cooling while maintaining the reaction mixture at pH 4 to 5 with 1N hydrochloric acid. The mixture was stirred at room temperature for 10 minutes. The reaction mixture was concentrated under reduced pressure. The residue was purified by reversed phase column chromatography (eluant: water) and freeze-dried to obtain 120 mg (yield: 74.5%) of disodium salt of (3R,5R,6R)-3-carboxy-7-oxo-3-(2-oxo-3-ureidoimidazolidin-1-yl)-6-[D-α-sulfo-α-(4-ureidophenyl)acetamido]-4-thia-1-azabicyclo[3.2.0]heptane.

IR (KBr) cm⁻¹: 1770, 1700, 1660, 1605

The following compound was obtained in the same manner.

Disodium salt of (3R,5R,6R)-3-carboxy-6-[D-α-(2-chloro-4-ureidophenyl)-α-sulfoacetamido]-7-oxo-3-(2-oxo-3-ureidoimidazolidin-1-yl)-4-thia-1-azabicyclo[3.2.0]heptane.

IR (KBr) cm$^{-1}$: 1760, 1700, 1660, 1610

EXAMPLE 43

In 20 ml of methanol was dissolved 200 mg of disodium salt of (3R,5R,6R)-6-[D-α-(4-acetoxy-3-nitrophenyl)-α-sulfoacetamido]-3-carboxy-7-oxo-3-(2-oxo-3-ureidoimidazolidin-1-yl)-4-thia-1-azabicyclo[3.2.0]heptane. Thereto were added 0.14 ml of acetic anhydride and 150 mg of 5% palladium-carbon in this order. The mixture was stirred at room temperature for 3 hours in a hydrogen atmosphere. After the completion of the reaction, the insolubles were removed by filtration. The filtrate was mixed with 50 ml of water. The mixture was concentrated under reduced pressure. The residue was purified by reversed phase column chromatography (eluant: water) to obtain 160 mg (yield: 78.4%) of disodium salt of (3R,5R,6R)-6-[D-α-(3-acetamido-4-hydroxyphenyl)-α-sulfoacetamido]-3-carboxy-7-oxo-3-(2-oxo-3-ureidoimidazolidin-1-yl)-4-thia-1-azabicyclo[3.2.0]heptane.

IR (KBr) cm$^{-1}$: 1770, 1660, 1615

EXAMPLE 44

(1) 3.27 g of di-tri-n-butyl amine salt of D-α-(2-chloro-4,5-dihydroxyphenyl)-α-sulfoacetic acid was suspended in 16.4 ml of methylene chloride. Thereto were added 1.30 ml of trimethylchlorosilane and 2.73 ml of tri-n-butylamine with ice cooling. The mixture was stirred for 30 minutes at the same temperature. Thereto was added 0.60 ml of isopropyl chlorocarbonate at −15° to −10° C. The mixture was stirred at the same temperature for 1 hour to obtain a solution of mixed anhydride.

(2) In 16.4 ml of methanol was suspended 1.75 g of (3R,5R,6R)-6-amino-3-carboxy-7-oxo-3-(2-oxo-3-ureidoimidazolidin-1-yl)-4-thia-1-azabicyclo[3.2.0]heptane. To the suspension was added 1.70 ml of tri-n-butylamine was added to obtain a solution. To the resulting solution was dropwise added the mixed anhydride solution prepared in (1) above, at a temperature of −50° C. or below. The temperature of reaction mixture was elevated to room temperature in 1 hour and stirred for 1 hour at the same temperature. To the reaction mixture were added 2.86 ml of acetic acid and 4.5 ml of a methanol solution containing 1.50 g of sodium acetate trihydrate in this order. The resulting mixture was stirred at room temperature for 1 hour. The resulting precipitates were collected by filtration, dissolved in 10 ml of water, and purified by reversed phase column chromatography (eluant: water) to obtain 2.08 g (yield: 65.2%) of disodium salt of (3R,5R,6R)-3-carboxy-6-[D-α-(2-chloro-4,5-dihydroxyphenyl)-α-sulfoacetamido]-7-oxo-3-(2-oxo-3-ureidoimidazolidin-1-yl)-4-thia-1-azabicyclo[3.2.0]heptane.

IR (KBr) cm$^{-1}$: 1760, 1700, 1670, 1610

The following compounds were obtained in the same manner.

Disodium salt of (3R,5R,6R)-3-(3-benzylideneamino-2-oxoimidazolidin-1-yl)-3-carboxy-6-[DL-α-(2-chloro-4,5-dihydroxyphenyl)-α-sulfoacetamido]-7-oxo-4-thia-1-azabicyclo[3.2.0]heptane IR (KBr) cm$^{-1}$: 1760, 1720, 1700, 1660, 1615

Disodium salt of (3R,5R,6R)-3-(3-benzylideneamino-2-oxoimidazolidin-1-yl)-3-carboxy-6-[DL-α-(2-chloro-4,5-dihydroxyphenyl)-α-sulfoacetamido]-7-oxo-4-thia-1-azabicyclo[3.2.0]heptane IR (KBr) cm$^{-1}$: 1760, 1720, 1700, 1660, 1615

Disodium salt of (3R,5R,6)-3-(3-benzylideneamino-2-oxoimidazolidin-1-yl)-3-carboxy-6-[D-α-(2-chloro-4,5-dihydroxyphenyl)-α-sulfoacetamido]-7-oxo-4-thia-1-azabicyclo[3.2.0]heptane Sodium salt of (3R,5R,6R)-6-[D-α-(2-chloro-4,5-dihydroxyphenyl)-α-sulfoacetamido]-3-diphenylmethyloxycarbonyl-7-oxo-3-(2 oxo-3-ureidoimidazolidin-1-yl)-4-thia-1-azabicyclo[3.2.0]heptane Sodium salt of (3R,5R,6R)-3-(3-benzylideneamino-2-oxoimidazolidin-1-yl)-6-[D-α-(2-chloro-4,5-dihydroxyphenyl)-α-sulfoacetamido]-3-diphenylmethyloxycarbonyl-7-oxo-4-thia-1-azabicyclo[3.2.0]heptane

EXAMPLE 45

In a mixed solvent consisting of 55 ml of acetonitrile and 18.5 ml of water was dissolved 3.70 g of disodium salt of (3R,5R,6R)-3-(3-benzylideneamino-2-oxoimidazolidin-1-yl)-3-carboxy-6-[D-α-(2-chloro-4,5-dihydroxyphenyl)-α-sulfoacetamido]-7-oxo-4-thia-1-azabicyclo[3.2.0]heptane. Thereto was added 2.54 g of 2,4-dinitrophenylhydrazine hydrochloride. The mixture was stirred at room temperature for 3 hours. To the reaction mixture was added 37 ml of water. The insolubles were removed by filtration and washed with 8 ml of water. The filtrate and the washings were combined and mixed with 50 ml of ethyl acetate. The mixture was adjusted to pH 6.0 with a saturated aqueous sodium hydrogencarbonate solution. The aqueous layer was separated, washed with 50 ml of ethyl acetate, and adjusted to pH 4.0 with 1N hydrochloric acid. Thereto was added 370 mg of active carbon, and the mixture was stirred for 5 minutes at room temperature. The active carbon was removed by filtration and washed with water. The filtrate and the washings were combined and concentrated under reduced pressure. The residue was purified by reversed phase column chromatography (eluant: water). The eluate was concentrated to about 10 ml. The residue was dropwise added to 100 ml of ethanol. The mixture was stirred for 30 minutes. The resulting crystals were collected by filtration, washed with 10 ml of ethanol, and dried under reduced pressure to obtain 2.04 g (yield: 63.3%) of disodium salt of (3R,5R,6R)-3-(3-amino-2-oxoimidazolidin-1-yl)-3-carboxy-6-[D-α-(2-chloro-4,5-dihydroxyphenyl)-α-sulfoacetamido]-7-oxo-4-thia-1-azabicyclo[3.2.0]heptane.

IR (KBr) cm$^{-1}$: 1765, 1700, 1665, 1615

The following compound was obtained in the same manner.

Disodium salt of (3R,5R,6R)-3-(3-amino-2-oxoimidazolidin-1-yl)-3-carboxy-6-[DL-α-(2-chloro-4,5-dihydroxyphenyl)-α-sulfoacetamido]-7-oxo-4-thia-1-azabicyclo[3.2.0]heptane IR (KBr) cm$^{-1}$: 1765, 1720, 1700–1660, 1615

EXAMPLE 46

(3R,5R,6R)-3-diphenylmethyloxycarbonyl-6-{DL-α-(p-methoxybenzyloxycarbonyl)-α-[4-(p-methoxybenzyloxy)phenyl]acetamido}-3-[3-p-nitrobenzyloxycarbonylaminomethylcarbonylamino)-2-oxoimidazolidin-1-yl]-7-oxo-4-thia-1-azabicyclo[3.2.0]heptane was reacted in the same manner as in Example 16 and then in the same manner as in Example 12 to obtain disodium salt of (3R,5R,6R)-3-(3-aminomethylcarbonylamino-2-oxoimidazolidin-1-yl)-3-carboxy-6-[DL-α-carboxy-α-

(p-hydroxyphenyl)acetamido]-7-oxo-4-thia-1-azabicyclo[3.2.0]heptane.

IR (KBr) cm$^{-1}$: 1770, 1720–1660, 1600

EXAMPLE 47

In a mixed solvent consisting of 1 ml of water and 1 ml of acetonitrile was dissolved 100 mg of disodium salt of (3R,5R,6R)-3-(3-amino-2-oxoimidazolidin-1-yl)-3-carboxy-6-[DL-α-(2-chloro-4,5-dihydroxyphenyl)-α-sulfoacetamido]-7-oxo-4-thia-1-azabicylo[3.2.0]heptane. Thereto were added 0.022 ml of acrolein and a catalytic amount of p-toluenesulfonic acid in this order. The mixture was stirred at room temperature for 2 hours. The reaction mixture was concentrated under reduced pressure. The residue was purified by reversed phase column chromatography (eluant: water/acetonitrile=1/0 to 97/3) and freeze-dried to obtain 64 mg (yield: 60.0%) of disodium salt of (3R,5R,6R)-3-carboxy-6-[DL-α-(2-chloro-4,5-dihydroxyphenyl)-α-sulfoacetamido]-7-oxo-3-(2-oxo-3-allylideneaminoimidazolidin-1-yl)-4-thia-1-azabicyclo[3.2.0]heptane.

IR (KBr) cm$^{-1}$: 1770, 1720, 1700–1660, 1620, 1600

By using cis-β-formylacrylic acid in place of acrolein, there was obtained trisodium salt of (3R,5R,6R)-3-[3-(-3-carboxy-2-allylideneamino)-2-oxoimidazolidin-1-yl]-3-carboxy-6-[DL-α-(2-chloro-4,5-dihydroxyphenyl)-α-sulfoacetamido]-7-oxo-4-thia-1-azabicyclo[3.2.0]heptane.

IR (KBr) cm$^{-1}$: 1770, 1720, 1710, 1630, 1620

EXAMPLE 48

In 3 ml of N,N-dimethylformamide was dissolved 0.64 g of disodium salt of (3R,5R,6R)-3-carboxy-6-[D-α-(2-chloro-4,5-dihydroxyphenyl)-α-sulfoacetamido]-7-oxo-3-(2-oxo-3-ureidoimidazolidin-1-yl)-4-thia-1-azabicyclo[3.2.0]heptane. Thereto was added 0.12 ml of benzyl bromide. The mixutre was stirred at room temperature for 2 days. The reaction mixture was subjected to evaporation to dryness under reduced pressure. The residue was dissolved in a mixed solvent consisting of 5 ml of water and 10 ml of ethyl acetate. The resulting mixture was adjusted to pH 6 with a saturated aqueous sodium hydrogencarbonate solution. The aqueous layer was separated and purified by reversed phase column chromatography (eluant: water/acetonitrile=93/7 to 90/10) to obtain 0.32 g (yield: 45.2%) of sodium salt of (3R,5R,6R)-3-benzyloxycarbonyl-6-[D-α-(2-chloro-4,5-dihydroxyphenyl)-α-sulfoacetamido]-7-oxo-3-(2-oxo-3-ureidoimidazolidin-1-yl)-4-thia-1-azabicyclo[3.2.0]heptane.

IR (KBr) cm$^{-1}$: 1775, 1720, 1700, 1670

The following compound was obtained in the same manner.

Sodium salt of (3R,5R,6R)-6-[D-α-(2-chloro-4,5-dihydrophenyl)-α-sulfoacetamido]-3-methoxycarbonyl-7-oxo-3-(2-oxo-3-ureidoimidazolidin-1-yl)-4-thia-1-azabicyclo[3.2.0]heptane IR (KBr) cm$^{-1}$: 1770, 1710, 1670, 1650

EXAMPLE 49

30 ml of benzene was added to 1.00 g of (3R,5R,6R)-6-amino-3-(3-benzylideneamino-2-oxo-imidazolidin-1-yl)-3-(p-nitrobenzyloxycarbonyl)-7-oxo-4-thia-1-azabicyclo[3.2.0]heptane and 0.46 g of 3,5-di-tert-butyl-4-hydroxybenzaldehyde. The mixture was subjected to azeotropy and dehydration under reflux for 1 hour using a Dean-Stark aparatus. The reaction mixture was cooled, and the solvent was removed by distillation under reduced pressure to obtain 1.40 g (yield: 98.6%) of (3R,5R,6R)-3-(3-benzylideneamino-2-oxoimidazolidin-1-yl)-6-(3,5-di-tert-butyl-4-hydroxybenzylideneamino)-3-(p-nitrobenzyloxycarbonyl)-7-oxo-4-thia-1-azabicyclo[3.2.0]heptane.

EXAMPLE 50

In a mixed solvent consisting of 3.2 ml of 1,2-dichloroethane and 9.6 ml of anhyrous benzene was dissolved 640 mg of (3R,5R,6R)-3-(3-benzylideneamino-2-oxoimidazolidin-1-yl)-6-(3,5-di-tert-butyl-4-hydroxybenzylideneamino)-3-(p-nitrobenzyloxycarbonyl)-7-oxo-4-thia-1-azabicyclo[3.2.0]heptane. Thereto were added 640 mg of anhydrous magnesium sulfate and 980 mg of nickel peroxide in this order with ice-cooling. The mixture was stirred at room temperature for 2.5 hours. The insolubles were removed by filtration. The solvent was removed by distillation under reduced pressure. The residue was dissolved in a mixed solvent consisting of 5 ml of methanol and 5 ml of methylene chloride. The mixture was stirred at room temperature for 1 hour. The solvent was removed by distillation under reduced pressure. The residue was purified by column chromatography (eluant: chloroform) to obtain 580 mg (yield: 87.1%) of (3R,5R)-3-(3-benzylideneamino-2-oxoimidazolidin-1-yl)-6-(3,5-di-tert-butyl-4-hydroxybenzylideneamino)-6-methoxy-3-(p-nitrobenzyloxycarbonyl)-7-oxo-4-thia-1-azabicyclo[3.2.0]heptane.

IR (KBr) cm$^{-1}$: 1770, 1720

EXAMPLE 51

In a mixed solvent consisting of 15 ml of methanol, 6 ml of tetrahydrofuran, 1.5 ml of water and 6 ml of methylene chloride was dissolved 740 mg of (3R,5R)-3-(3-benzylideneamino-2-oxoimidazolidin-1-yl)-6-(3,5-di-tert-butyl-4-hydroxybenzylideneamino)-6-methoxy-3-(p-nitrobenzyloxycarbonyl)-7-oxo-4-thia-1-azabicyclo[3.2.0]heptane. Thereto was added 240 mg of a Girard reagent (2-hydrazino-N,N,N-trimethyl-2-oxoethanaminium chloride). The mixture was stirred at room temperature for 1 hour. To the reaction mixture were added 30 ml of methylene chloride and 10 ml of water. The resulting mixture was adjusted to pH 7.0 with a saturated aqueous sodium hydrogencarbonate solution. The organic layer was separated, washed with a saturated aqueous sodium chloride solution, and dried over anhydrous magnesium sulfate. The solvent was removed by distillation under reduced pressure. The residue was purified by column chromatography (eluant: benzene/ethyl acetate=5/1 to 1/1) to obtain 320 mg (yield: 60.6%) of (3R,5R)-6-amino-3-(3-benzylideneamino-2-oxoimidazolidin-1-yl)-6-methoxy-3-(p-nitrobenzyloxycarbonyl)-7-oxo-4-thia-1-azabicyclo[3.2.0]heptane.

IR (KBr) cm$^{-1}$: 1770, 1710

PREPARATION EXAMPLE 1

An aqueous disodium salt solution of (3R,5R,6R)-3-carboxy-6-[D-α-(2-chloro-4-hydroxyphenyl)-α-sulfoacetamido]-7-oxo-3-(2-oxo-3-ureidoimidazolidin-1-yl)-4-thia-1-azabicyclo[3.2.0]heptane was treated in a conventional manner to obtain a freeze-dried and sterilized disodium salt. One gram (potency) of disodium salt was dissolved in 20 ml of physiological saline solution to obtain an injection.

PREPARATION EXAMPLE 2

An aqueous disodium salt solution of (3R,5R,6R)-3-carboxy-6-[D-α-(2-chloro-4,5-dihydroxyphenyl)-α-sulfoacetamido]-7-oxo-3-(2-oxo-3-ureidoimidazolidin-1-yl)-4-thia-1-azabicylo[3.2.0]heptane was treated in a conventional manner to obtain a freeze-dried and sterilized disodium salt. One gram (potency) of disodium salt was dissolved in 20 ml of physiological saline to obtain an injection.

What is claimed is:

1. A penam derivative represented by the following formula or a pharmaceutically acceptable salt thereof:

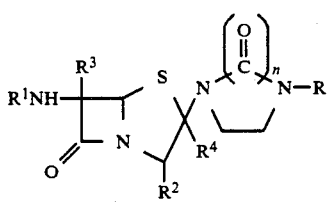

wherein $R^1$ represents a hydrogen atom, a formyl, 2,6-dimethyloxyphenylphenyl-carbonyl or 5-methyl-3-phenylisoxazol-4-ylcarbonyl group or an acyl group represented by the formula:

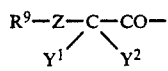

wherein $R^9$ represents an unsubstituted or substituted lower alkyl, lower alkenyl, aryl or heterocyclic group; Z represents an oxygen or sulfur atom or a linkage; $Y^1$ represents a hydrogen atom; $Y^2$ represents a hydrogen atom, halogen atom, a hydroxyl group, a carboxyl group, a sulfo group, a sulfoamino group, a amino group or a group of the formula, $R^{10}$CONH— in which $R^{10}$ is an unsubstituted or substituted aryl, arylcarbonylamino, heterocyclicamino or heterocyclic group; and $Y^1$ and $Y^2$ may form, when taken together, an unsubstituted or substituted lower alkoxyimino, cycloalkyloxyimino, aralkyloxyimino, lower alkylidene, lower alkenylidene, lower alkoxymethylene, halomethylene or heterocyclic-oxyimino group; $R^2$ represents a hydrogen atom or a lower alkyl group; $R^3$ represents a hydrogen atom, a lower alkoxy group, a lower alkylthio group or a formamido group; $R^4$ represents a protected or unprotected carboxyl group or a carboxylato group; R represents a group of the formula, —NHR$^5$ or NR$^5$R$^6$ (in which R$^5$ and R$^6$, may be the same or different, represent hydroxyl groups, cyano groups, sulfo groups or unsubstituted or substituted lower alkyl, aryl, acyl, carbamoyl, sulfamoyl, lower alkylsulfonyl or heterocyclic groups), or a group of the formula, —N=CR$^5$R$^6$ (in which R$^7$ and R$^8$, which may be the same or different, represent hydrogen atoms or carboxyl groups, cyano groups or substituted or unsubstituted lower alkyl, lower alkenyl, lower alkynyl, aryl, amino, acyl, acyloxy, carbamoyl, carbamoyloxy, sulfamoyl, lower alkylthio, ureido or heterocyclic groups, or $R^7$ and $R^8$ may form a cycloalkene or heterocyclic ring with the carbon atom to which $R^7$ and $R^8$ are attached); and n represents 1 or 2; each of the substituted lower alkyl, lower alkenyl, aryl, and heterocyclic groups in the definition of $R^9$ having at least one substituent selected from the group consisting of halogen atoms, hydroxyl group, amino group, amino-lower alkyl groups, carboxyl group, lower alkoxy groups, ureido group, acylamino groups, cyano group, sulfo group, carbamoyloxy group, sulfamoyl group, nitro group, oxo group and heterocyclic groups; each of the substituted aryl, arylcarbonylamino, heterocyclicamino and heterocyclic groups in the definition of $R^{10}$ having at least one substituent selected from the group consisting of halogen atoms, hydroxyl group, oxo group, lower alkyl groups, halo-lower alkyl groups, hydroxyl-lower alkyl groups, lower alkylthio groups, lower alkylthio-lower alkyl groups, aryl groups, haloaryl groups, cycloalkyl groups, arylamino groups, lower alkylsulfonyl groups and sulfamoylarylamino groups; each of the substituted lower alkoxyimino, cycloalkyloxyimino, aralkyloxyimino, lower alkylidene, lower alkenylidene, lower alkoxymethylene, halomethylene and heterocyclicoxyimino group in the definition of the group which $Y^1$ and $Y^2$ may form having at least one substituent selected from the group consisting of halogen atoms, acyloxy groups and carboxyl groups, each of the substituted lower alkyl, lower alkenyl, lower alkynyl, aryl, amino, acyl, acyloxy, carbamoyl, carbamoyloxy, sulfamoyl, lower alkylsulfonyl or heterocyclic groups in the definition of $R^5$ and $R^6$ having at least one substituent selected from the group consisting of halogen atoms, halo-lower alkyl groups, lower alkyl groups, lower alkoxy groups, carboxyl-lower alkoxy groups, lower alkylthio groups, carboxyl-lower alkylthio groups, lower alkanoyloxy groups, lower alkoxycarbonyl groups, diphenylmethoxycarbonyl group, aryloxycarbonyl groups, hydroxyl-lower alkoxy groups, lower alkoxyimino groups, imino group, amino-lower alkyl groups, carboxyl-lower alkyl groups, lower alkoxycarbonyl-lower alkyl groups, lower alkoxycarbonylamino groups, nitrobenzyloxycarbonylamino groups, cyano-lower alkylamino-lower alkyl groups, N,N-di-lower alkylamino groups, lower alkylsulfonyl groups, sulfamoyl-lower alkyl groups, aryl groups, aralkyl groups, carbamoyl group, sulfo group acyl groups, oxo group, carbonyl group, nitro group, cyano group, amino group, hydroxyl group, ureido group, aralkyloxy groups, sulfamoyl group, thioxo group, methylenedioxy group, heterocyclic groups and heterocyclicthio groups; each of the substituted lower alkyl, aryl, acyl, carbamoyl, sulfamoyl, lower alkylthio, ureido and heterocyclic groups in the definition of $R^7$ and $R^8$ and each of the cycloalkene and heterocyclic ring in the definition of the group which $R^7$ and $R^8$ may form having at least one substituent selected from the group consisting of halogen atoms, halo-lower alkyl groups, lower alkyl groups, lower alkoxy groups, carboxyl-lower alkoxy groups, lower alkylthio groups, carboxyl-lower alkylthio groups, lower alkanoyloxy groups, lower alkoxycarbonyl groups, diphenylmethoxycarbonyl group, aryloxycarbonyl groups, hydroxyl-lower alkyl groups, lower alkoxyimino groups, imino group, amino-lower alkyl groups, carboxyl-lower alkyl groups, lower alkoxycarbonyl-lower alkyl groups, lower alkoxycarbonylamino groups, nitrobenzyloxycarbonylamino groups, cyano-lower alkylamino-lower alkyl groups, N,N-di-lower alkylamino groups, lower alkylsulfonyl groups, sulfamoyl-lower alkyl groups, aryl groups, aralkyl groups, carbamoyl group, sulfo group, acyl groups, oxo group, carboxyl group, nitro group, cyano group, amino group, hydroxyl group, ureido group, aralkyloxy group, sulfamoyl group, thioxo group, methylenedioxy group, heterocyclic groups and heterocyclicthio groups; wherein the substituent for each of $R^5$, $R^6$, $R^7$ and $R^8$ may have at least one substituent selected from the group consisting of lower alkyl groups, amino group, oxo group, hydroxyl group, carbamoyl group, hydroxyl-lower alkyl groups, protected or unprotected carboxyl-lower alkyl groups, N,N-di-lower alkylamino groups, acylamino groups, heterocyclic groups, ureido group, trimethylammonioacetyl group, and guanidino group; wherein the term "acyl" in "acyl group", "acyloxy group" and "acylamino group" means formyl, $C_{2-5}$alkanoyl, $C_{3-5}$alkenoyl, benzoyl, naphthoyl, thenoyl, furoyl, isonicotinoyl, nicotinoyl, 1,4-dihydropyridin-2-ylcarbonyl or 4-ethyl-2,3-dioxopiperazin-1-ylcarbonyl; the term "aryl" in "aryl group", "N,N'-di-lower alkylaminoaryl group", "arylamino group", "arylcarbonylamino group", "sulfamoylarylamino group", "aryloxycarbonyl group" and "haloaryl group" means phenyl, naphthyl or indanyl; the term "aralkyl" in "aralkyl group", "aralkyloxy group" and "aralkyloxyimino group" means benzyl, phenethyl, 4-methylbenzyl and naphthylmethyl; the term "heterocyclic" in "heterocyclic group", "heterocyclic amino group", "heterocyclic-oxyimino group" or "heterocyclicthio group" means azetidinyl, thienyl, furyl, pyrrolyl, 1,2,4-triazolyl, 1,2,3-triazolyl, oxazolyl, thiazolyl, tetrazolyl, 1,3-dithiolanyl, pyridinyl, 1-hydroxyl-4-oxo-1,4-dihydropyridyl, 1,4-dihydropyridiyl, thiazolidinyl, thiazolidinyl, oxazolidinyl, imidazolidinyl, pyrazolinyl, pyrrolidinyl, 2-oxazolinyl, imidazolinyl, furazanyl, isothiazolyl, 4,5-dihydrothiazolyl, 2,3-dihydrofuryl, 2,5-dihydrofuryl, tetrahydrofuryl, 1,2,3-thiadiazolyl, 1,2,4-thiadiazolyl, 1,3,4-thiadiazolyl, 1,2,5-thiadiazolyl, imidazolyl, pyrazolyl, 3-pyrrolinyl, 4,5-dihydropyrazolyl, isoxazolyl, isoxazolidinyl, 1,2,3-oxadiazolyl, 1,3,4-oxadiazolyl, 1,2,4-oxadiazolyl, piperidinyl, piperazinyl, tetrahydropyrazinyl, morpholinyl, pyrimidinyl, pyrazinyl, 1,2,4-triazinyl, 1,3,5-triazinyl, 2H-3,4-dihydropyranyl, 2H-5,6-dihydropyranyl, 1,4-oxazinyl, pyridazinyl, 2H-thiazinyl, perhydrooxazinyl, dihydrooxazinyl, chromenyl, benzothienyl, benzoisothiazolidinyl, imidazo[1,2-b][1,2,4]triazinyl, thieno[3,2-b]thienyl, benzotriazolyl, 1,2,3-benzothiadiazolyl, tetrazolo[5,1-b]pyridazinyl, 2,1,3-benzoxadiazolyl, imidazo[1,2-a]pyridyl, imidazo[1,2-a]pyrimidinyl, imidazo[1,2-b][1,3]thiazolyl, 5,6,7,8-tetrahydroimidazo[1,2-a]pyridyl, imidazo[1,2-a]pyrazinyl, 1,4-benzomorpholinyl, benzothiazolyl, isoinodlinyl, benzofuranyl, 1,4-benzothiomorpholinyl, 1,3-benzoxazolidinyl, triazolo[1,5-a]pyrimidinyl, indolinyl, indazolyl, benzoxazolyl, henzoisoxazyolyl, purinyl, isoquinolyl, quinolyl, 1,8-naphthyridinyl, 1,5-naphthyridinyl, 1,1-dioxo-1,2-benzoisothiazolidinyl, 1,2-dihydro-4H-3,1-benzoxazinyl, 1,2-benzoxazinyl, quinoxalinyl, quinazolinyl, cinnolinyl, indolyl, quinuclidinyl, perhydroazaepinyl, or 3-pyrrolin-2-yl, and said heterocyclic group, when containing a nitrogen atom as the heteroatom, may be quaternized; and the term "heterocyclic ring" means azetidine, 1,3-dithiolane, 1,4-dihydropyridine, thiazolidine, oxazolidine, imidazolidine, pyrazoline, pyrrolidine, 2-oxazoline, imidazoline, 4,5-dihydrothiazole, 2,3-dihydrofuran, 2,5-dihydrofuran, tetrahydrofuran, 3-pyrroline, 4,5-dihydropyrazole, isoxazolidine, piperidine, piperazine, tetrahydropyrazine, morpholine, tetrahydro-pyrimidine, 2H-3,4-dihydropyran, 2H-5,6-dihydropyran, 2H-thiazine, dihydrooxazine, chromene, benzoisothiazolidine, 5,6,7,8-tetrahydroimidazo[1,2-a]pyridine, 1,4-benzomorpholine, isoindoline, 1,4-benzothiomorpholine, 1,3-benzoxazolidine, indoline, 1,1-dioxo-1,2-benzoisothiazolidine, 1,2-dihydro-4H-3,1-benzoxazine or quinuclidine.

2. A penam derivative or a pharmaceutically acceptable salt thereof according to claim 1, wherein $R^2$ and $R^3$ are hydrogen atoms.

3. A penam derivative or a pharmaceutically acceptable salt thereof according to claim 1 or 2, wherein $R^1$ is an acyl group.

4. A penam derivative or a pharmaceutically acceptable salt thereof according to claim 1 or 2, wherein R is a group of the formula, $-NHR^5$ in which $R^5$ is as defined in claim 1.

5. A penam derivative or a pharmaceutically acceptable salt thereof according to claim 4, wherein $R^5$ is a sulfo group or an acyl, sulfamoyl, lower alkylsulfonyl or carbamoyl group which may be substituted by at least one substituent selected from the group consisting of a halogen atom, a lower alkyl group, a carbamoyl group, a protected or unprotected carboxyl group, a protected or unprotected amino group, a protected or unprotected hydroxyl group, an oxo group, a ureido group and a sulfamoyl group.

6. A penam derivative or a pharmaceutically acceptable salt thereof according to claim 1 or 2, wherein R is a group of the formula, $-N=CR^7R^8$ in which $R^7$ and $R^8$ are as defined in claim 1.

7. A penam derivative or a pharmaceutically acceptable salt thereof to claim 6, wherein $R^7$ is a hydrogen atom.

8. A penam derivative or a pharmaceutically acceptable salt thereof according to claim 7, wherein $R^8$ is a carboxyl group, a cyano group or a lower alkyl, lower alkenyl, lower alkynyl, aryl, acyl, carbamoyl or heterocyclic group which may be substituted by at least one substituent selected from the group consisting of a halogen atom, a cyano group, an oxo group, a nitro group, a sulfo group, a carboxyl group, a hydroxyl group, a lower alkyl group, a lower alkoxy group, a hydroxyl-lower alkyl group, a amino group, a carboxyl-lower alkyl group, an aryl group, a lower alkoxyimino group, a di-lower alkylamino group, an imino group, a carbamoyl group, an acyl group, a heterocyclic group and a heterocyclicthio group; said lower alkyl, lower alkoxy, hydroxyl-lower alkyl, carboxyl-lower alkyl group, lower alkoxyimino, imino, carbamoyl, acyl, heterocyclic and heterocyclicthio group for the substituent of $R^8$ may be substituted by at least one substituent selected from the group consisting of a lower alkyl group, a amino group, a carbamoyl group, an oxo group, a hydroxyl-lower alkyl group, a N,N-di-lower alkylamino group, a carboxyl-lower alkyl group, a heterocyclic group, a trimethylammonioacetyl group, a ureido group and a guanidino group.

9. A penam derivative or a pharmaceutically acceptable salt thereof according to claim 6, wherein $R^7$ and $R^8$ form a heterocyclic ring with the carbon atom to which $R^7$ and $R^8$ are attached.

10. A penam derivative or a pharmaceutically acceptable salt thereof according to claim 1 or 2 wherein n is 1.

11. A penam derivative or a pharmaceutically acceptable salt thereof according to claim 10, wherein $R^1$ represents a group of the formula:

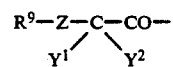

wherein R⁹ represents a lower alkyl, aryl or heterocyclic group which may be substituted by at least one substituent selected from the group consisting of a halogen atom, a protected or unprotected hydroxyl group, a protected or unprotected amino group, a protected or unprotected amino-lower alkyl group, a protected or unprotected carboxyl group, a lower alkoxy group, a ureido group, a cyano group, a carbamoyloxy group and a nitro group; Z represents an oxygen or sulfur atom or a linkage; Y¹ represents a hydrogen atom; Y² represents a hydrogen atom, a protected or unprotected hydroxyl group, a protected or unprotected carboxyl group, a sulfo group, a sulfoamino group, a protected or unprotected amino group or a group of the formula, R¹⁰CONH— in which R¹⁰ represents a heterocyclic group which may be substituted by at least one substituent selected from the group consisting of a halogen atom, a protected or unprotected hydroxyl group, an oxo group, a lower alkyl group, an aryl group, a cycloalkyl group or a lower alkylsulfonyl group; and Y¹ and Y² form, when taken together, a lower alkoxyimino or aralkyloxyimino group which may be substituted by at least one substituent selected from the group consisting of a halogen atom and a protected or unprotected carboxyl group.

12. (3R,5R,6R)-3-Carboxy-6-[DL-α-(2-chloro-4,5-dihydroxyphenyl)-α-sulfoacetamido]-7-oxo-3-(2-oxo-3-allylideneaminoimidazolidin-1-yl)-4-thia-1-azabicyclo[3.2.0]heptane or a pharmaceutically acceptable salt thereof.

13. (3R,5R,6R)-3-Carboxy-6-[D-α-(2-chloro-4,5-dihydroxyphenyl)-α-sulfoacetamido]-7-oxo-3-(2-oxo-3-semicarbazonoethylideneaminoimidazolidin-1-yl)-4-thia-1-azabicyclo[3.2.0]heptane or a pharmaceutically acceptable salt thereof.

14. (3R,5R,6R)-3-Carboxy-3-{3-[(1,5-dihydroxy--4-oxo-1,4-dihydropyridin-2-yl)methylideneamino]-2-oxoimidazolidin-1-yl}-6-[D-α-(4-ethyl-2,3-dioxo-1-piperazinecarboxamino)-α-(p-hydroxyphenyl-)acetamido]-7-oxo-4-thia-1-azabicyclo[3.2.0]heptane or a pharmaceutically acceptable salt thereof.

15. (3R,5R,6R)-3-Carboxy-3-[3-(3-carboxyallylideneamino)-2-oxoimidazolidin-1-yl]-6-[DL-α-(2-chloro-4,5-dihydroxyphenyl)-α-sulfoacetamido]-7-oxo-4-thia-1azabicyclo[3.2.0]heptane or a pharmaceutically acceptable salt thereof.

16. (3R,5R,6R)-6-[2-(2-Aminothiazol-4-yl)-2-(Z)--methoxyiminoacetamido]-3-carboxy-3-[3-(1,3-dithiolan-2-ylideneamino)-2-oxoimidazolidin-1-yl]-7-oxo-4-thia-1-azabicyclo[3.2.0]heptane or a pharmaceutically acceptable salt thereof.

17. (3R,5R,6R)-3-Carboxy-6-[D-α-(2-chloro-4-hydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

18. (3R,5R,6R)-3-Carboxy-6-[D-α-(2-chloro-4,5-dihydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

19. (3R,5R,6R)-3-Carboxylato-6-[D-α-(4-ethyl-2,3-dioxo-1-piperazinecarboxamido)-α-(4-hydroxyphenyl)acetamido]-3-{3-[2-(3-methyl-1-imidazolidinium)ethylideneamino]-2-oxoimidazolidin-1-yl}-7-oxo-4-thia-1-azabicyclo[3.2.0]heptane or a pharmaceutically acceptable salt thereof.

20. (3R,5R,6R)-3-Carboxy-6-[D-α-(5-hydroxyl-4-oxo-1,4-dihydropyridin-2-ylcarboxamido)-α-(p-hydroxyphenyl)acetamido]-3-[3-(1,3-dithiolan-2-ylideneamino)-2-oxoimidazolidin-1-yl]-7-oxo-4-thia-1-azabicyclo[3.2.0-]heptane or a pharmaceutically acceptable salt thereof.

21. (3R,5R,6R)-3-Carboxy-6-[D-α-(4-ethyl-2,3-dioxo-1-piperazinecarboxamido)-α-phenylacetamido]-7-oxo-3-[3-(3,4-dihydroxybenzylideneamino)-2-oxoimidazolidin-1-yl]-4-thia-1-azabicyclo[3.2.0]heptane or a pharmaceutically acceptable salt thereof.

22. (3R,5R,6R)-3-Carboxy-6-[D-α-(2-fluoro-4-hydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

23. (3R,5R,6R)-3-Carboxy-6-[D-α-(3-fluoro-4-hydroxyphenyl)-α-sulfoacetamido[-7-oxo-3-(2-oxo-3-ureidoimidazolidin-1-yl)-4-thia-1-azabicyclo[3.2.0]heptane or a pharmaceutically acceptable salt thereof.

24. (3R,5R,6R)-3-Carboxy-6-[D-α-(4-hydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

25. (3R,5R,6R)-3-Carboxy-6-[D-α-(3,4-dihydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

26. An antibacterial agent comprising a penam derivative represented by the following formula or a pharmaceutically acceptable salt thereof:

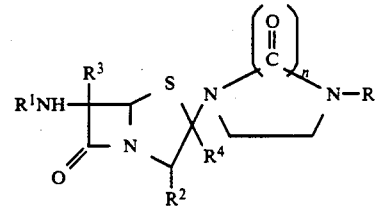

wherein R¹ represents a hydrogen atom, a formyl, 2,6-dimethyloxyphenylcarbonyl or 5-methyl-3-phenylisoxazol-4-ylcarbonyl group or an acyl group represented by the formula:

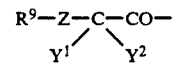

wherein R⁹ represents an unsubstituted or substituted lower alkyl, lower alkenyl, aryl or heterocyclic group; Z represents an oxygen or sulfur atom or a linkage; Y¹ represents a hydrogen atom; Y² represents a hydrogen atom, halogen atom, a hydroxyl group, a carboxyl group, a sulfo group, a sulfoamino group, a amino group or a group of the formula R¹⁰CONH— in which R¹⁰ is an unsubstituted or substituted aryl, arylcarbonylamino, heterocyclicamino or heterocyclic group; and Y¹ and Y² may form, when taken together, an unsubstituted or substituted lower alkoxyimino, cycloalkyloxyimino, aralkyloxyimino, lower alkylidene, lower alkenylidene, lower alkoxymethylene, halomethylene or heterocyclic-oxyimino group; R² represents a hydrogen atom or a lower alkyl group; R³ represents a hydrogen atom, a lower alkoxy group, a lower alkylthio group or a formamido group; R⁴ represents a protected or unprotected carboxyl group or a carboxylato group; R represents a group of the formula, —NHR⁵ or —NR⁵R⁶ (in which R⁵ and R⁶, which may be the same or different, represent hydroxyl groups, cyano groups, sulfo groups or unsubstituted or substituted lower alkyl, aryl, acyl, carbamoyl, sulfamoyl, lower alkylsulfonyl or heterocyclic groups), or a group of the formula —N=CR$^7$R$^8$ (in which R$^7$ and R$^8$, which may be the same or different, represent hydrogen atoms or carboxyl groups, cyano groups or substituted or unsubstituted lower alkyl, lower alkenyl, lower alkynyl, aryl, amino, acyl, acyloxy, carbamoyl, carbamoyloxy, sulfamoyl, lower alkylthio, ureido or heterocyclic groups, or R$^7$ and R$^8$ may form a cycloalkene or heterocyclic ring with the carbon atom to which R$^7$ and R$^8$ are attached); and n represents 1 or 2; each of the substituted lower alkyl, lower alkenyl, aryl, and heterocyclic groups in the definition of R$^8$ having at least one substituent selected from the group consisting of halogen atoms, hydroxyl group, amino group, amino-lower alkyl groups, carboxyl group, lower alkoxy groups, ureido group, acylamino groups, cyano group, sulfo group, carbamoyloxy group, sulfamoyl group, nitro group, oxo group and heterocyclic groups; each of the substituted aryl, arylcarbonylamino, heterocyclicamino and heterocyclic groups in the definition of R$^{10}$ having at least one substituent selected from the group consisting of halogen atoms, hydroxyl group, oxo group, lower alkyl groups, halo-lower alkyl groups, hydroxyl-lower alkyl groups, lower alkylthio groups, lower alkylthio-lower alkyl groups, aryl groups, haloaryl groups, cycloalkyl groups, arylamino groups, lower alkylsulfonyl groups and sulfamoylarylamino groups; each of the substituted lower alkoxyimino, cycloalkyloxyimino, aralkyloxyimino, lower alkylidene, lower alkenylidene, lower alkoxymethylene, halomethylene and heterocyclicoxyimino groups in the definition of the group which Y$^1$ and Y$^2$ may form having at least one substituent selected from the group consisting of halogen atoms, acyloxy groups and carboxyl groups; each of the substituted lower alkyl, aryl, acyl, carbamoyl, sulfamoyl, lower alkylsulfonyl or heterocyclic groups in the definition of R$^5$ and R$^6$ having at least one substituent selected from the group consisting of halogen atoms, halo-lower alkyl groups, lower alkyl groups, lower alkoxy groups, carboxyl-lower alkoxy groups, lower alkylthio groups, carboxyl-lower alkylthio groups, lower alkanoyloxy groups, lower alkoxycarbonyl groups, diphenylmethoxycarbonyl group, aryloxycarbonyl groups, hydroxyl-lower alkyl groups, lower alkoxyimino groups, imino group, amino-lower alkyl groups, carboxyl-lower alkyl groups, lower alkyloxycarbonyl-lower alkyl groups, lower alkoxycarbonylamino groups, nitrobenzyloxycarbonylamino group, cyano-lower alkylamino-lower alkyl groups, N,N-di-lower alkylamino groups, lower alkylsulfonyl groups, sulfamoyl-lower alkyl groups, aryl groups, aralkyl groups, carbamoyl group, sulfo group, acyl groups, oxo group, carboxyl group, nitro group, cyano group, amino group, hydroxyl group, ureido group, aralkyloxy groups, sulfamoyl group, thioxo group, methylenedioxy group, heterocyclic groups and heterocyclicthio groups; each of the substituted lower alkyl, lower alkenyl, lower alkynyl, aryl, amino, acyl, acyloxy, carbamoyl, carbamoyloxy, sulfamoyl, lower alkylthio, ureido and heterocyclic groups in the definition of R$^7$ and R$^8$ and each of the cycloalkene and heterocyclic ring in the definition of the group which R$^7$ and R$^8$ may form having at least one substituent selected from the group consisting of halogen atoms, halo-lower alkyl groups, lower alkyl groups, lower alkoxy groups, carboxyl-lower alkoxy groups, lower alkylthio groups, carboxyl-lower alkylthio groups, lower alkanoyloxy groups, lower alkoxycarbonyl groups, diphenylmethoxycarbonyl group, aryloxycarbonyl groups, hydroxyl-lower alkyl groups, lower alkoxyimino groups, imino group, amino-lower alkyl groups, carboxyl-lower alkyl groups, lower alkoxycarbonyl-lower alkyl groups, lower alkoxycarbonylamino groups, nitrobenzyloxycarbonylamino groups, cyano-lower alkylamino-lower alkyl groups, N,N-di-lower alkylamino groups, lower alkylsulfonyl groups, sulfamoyl-lower alkyl groups, aryl groups, aralkyl groups, carbamoyl group, sulfo group, acyl groups, oxo group, carboxyl group, nitro group, cyano group, amino group, hydroxyl group, ureido group, aralkyloxy groups, sulfamoyl group, thioxo group, methylenedioxy group, heterocyclic groups and heterocyclicthio groups; wherein the substituent for each of R$^5$, R$^6$, R$^7$ and R$^8$ may have at least one substituent selected from the group consisting of lower alkyl groups, amino group, oxo group, hydroxyl group, carbamoyl group, hydroxyl-lower alkyl groups, carboxyl-lower alkyl groups, N,N-di-lower alkylamino groups, acylamino groups, heterocyclic groups, ureido group, trimethylammonioacetyl group, and guanidino group; wherein the term "acyl" in "acyl group", "acyloxy group" and "acylamino group" means formyl, C$_{2-5}$alkanoyl, C$_{3-5}$alkenoyl, benzoyl, naphthoyl, thenoyl, furoyl, isonicotinoyl, nicotinoyl, 1,4-dihydropyridin-2-ylcarbonyl or 4-ethyl-2,3-dioxopiperazin-1-ylcarbonyl; the term "aryl" in "aryl group", "arylcarbonylamino group", "sulfamoylarylamino group", "aryloxycarbonyl group" and "haloaryl group" means phenyl, naphthyl or indanyl; the term "aralkyl" in "aralkyl group", "aralkyloxy group" and "aralkyloxyimino group" means benzyl, phenethyl, 4-methylbenzyl or naphthylmethyl; the term "heterocyclic" in "heterocyclic group", "heterocyclic amino group", "heterocyclicoxyimino group", or "heterocyclicthio group" means azetidinyl, thienyl, furyl, pyrrolyl, 1,2,4-tri-azolyl, 1,2,3-triazolyl, oxazolyl, thiazolyl, tetrazolyl, 1,3-dithiolanyl, pyridyl, 1-hydroxy-4-oxo-1,4-dihydropyridyl, 1,4-dihydropyridyl, thiazolidinyl, oxazolidinyl, imidazolidinyl, pyrazolinyl, pyrrolidinyl, 2-oxazolinyl, imidazolinyl, furazanyl, isothiazolyl, 4,5-dihydrothiazolyl, 2,3-dihydrofuryl, 2,5-dihydrofuryl, tetrahydrofuryl, 1,2,3-thiadiazolyl, 1,2,4-thiadiazolyl, 1,3,4-thiadiazolyl, 1,2,5-thiadiazolyl, imidazolyl, pyrazolyl, 3-pyrrolinyl, 4,5-dihydropyrazolyl, isoxazolyl, isoxazolidinyl, 1,2,3-oxadiazolyl, 1,3,4-oxadiazolyl, 1,2,4-oxadiazolyl, piperidinyl, piperazinyl, tetrahydropyrazinyl, morpholinyl, pyrimidinyl, pyrazinyl, 1,2,4-triazinyl, 1,3,5-triazinyll, 2H-3,4-dihydropyranyl, 2H-5,6-dihydropyranyl, 1,4-oxazinyl, pyridazinyl, 2H-thiazinyl, perhydrooxazinyl, dihydrooxazinyl, chromenyl, benzothienyl, benzoisothiazolidinyl, imidazo[1,2-b][1,2,4-triazinyl, thieno[3,2-b]thienyl, benzotriazolyl, 1,2,3-benzothiadiazolyl, tetrazolo[5,1-b]pyridazinyl, 2,1,3-benzoxadiaolyl, imidazo[1,2-b]pyridyl, imidazo[1,2-b]pyrimidinyl, imidazo[1,2-b][1,3]thiazolyl, 5,6,7,8-tetrahydroimidazo[1,2-a]pyridyl, imidazo[1,2-b]pyrazinyl, 1,4-benzomorpholinyl, benzothiazolyl, isoindolinyl, benzofuranyl, 1,4-benzothiomorpholinyl, 1,3-benzoxazolidinyl, triazolo[1,5-a]pyrimidinyl, indolinyl, indazolyl, benzoxazolyl, benzoisoxazolyl, purinyl, isoquinolyl, quinolyl, 1,8-naphthyridinyl, 1,5-naphthyridinyl, 1,1-dioxo-1,2-benzoisothiazolidinyl, 1,2-dihydro-4H-3,1-benzoxazinyl, 1,2-benzoxazinyl, quinoxalinyl, quinazolinyl, cinnolinyl, indolyl, quinuclidinyl, perhydroazaepinyl, or 3-pyrrolin-2-yl, and said heterocyclic group, when containing a nitrogen atom as the heteroatom, may be quaternized; and the term "heterocyclic ring" mentioned for $R^7$ and $R^8$ represents azetidine, 1,3-dithiolane, 1,4-dihydropyridine, thiazolidine, oxazolidine, imidazolidine, pyrazoline, pyrrolidine, 2-oxazoline, imidazoline, 4,5-dihydrothiazole, 2,3-dihydrofuran, 2,5-dihydrofuran, tetrahydrofuran, 3-pyrroline, 4,5-dihydropyrazole, isoxazolidine, piperidine, piperazine, tetrahydropyrazine, morpholine, tetrahydro-pyrimidine, 2H-3,4-dihydropyran, 2H-5,6-dihydropyran, 2H-thiazine, dihydrooxazine, chromene, benzoisothiazolidine, 5,6,7,8-tetrahydroimidazo[1,2-a]pyridine, 1,4-benzomorpholine, isoindoline, 1,4-benzothiomorpholine, 1,3-benzoxazolidine, indoline, 1,1-dioxo-1,2-benzoisothiazolidine, 1,2-dihydro-4H-3,1-benzoxazine or quinuclidine, and a pharmaceutically acceptable carrier.

27. An antibacterial agent according to claim 26, wherein $R^2$ and $R^3$ are hydrogen atoms.

28. An antibacterial agent according to claim 26 or 27, wherein $R^1$ is a formyl, 2,6-dimethyloxyphenylcarbonyl or 5-methyl-3-phenylisoxazol-4-ylcarbonyl group or a group represented by the formula:

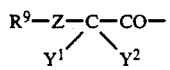

wherein $R^9$, $Y^1$, $Y^2$ and $Z$ are as defined in claim 26.

29. An antibacterial agent according to claim 26 or 27, wherein R is a group of the formula, $-NHR^5$ in which $R^5$ is as defined in claim 26.

30. An antibacterial agent according to claim 29, wherein $R^5$ is a sulfo group or an acyl, sulfamoyl, lower alkylsulfonyl or carbamoyl group which may be substituted by at least one substituent selected from the group consisting of a halogen atom, a lower alkyl group, a carbamoyl group, a protected or unprotected carboxyl group, a protected or unprotected amino group, a protected or unprotected hydroxyl group, an oxo group, a ureido group and a sulfamoyl group.

31. An antibacterial agent according to claim 26 or 27, wherein R is a group of the formula, $-N=CR^7R^8$ in which $R^7$ and $R^8$ are as defined in claim 26.

32. An antibacterial agent according to claim 31, wherein $R^7$ is a hydrogen atom.

33. An antibacterial agent according to claim 26 or 27, wherein n is 1.

34. An antibacterial agent according to claim 32, wherein $R^8$ is a carboxyl group, a cyano group or a lower alkyl, lower alkenyl, lower alkynyl, aryl, acyl, carbamoyl or heterocyclic group which may be substituted by at least one substituent selected from the group consisting of a halogen atom, a cyano group, an oxo group, a nitro group, a sulfo group, a carboxyl group, a hydroxyl group, a lower alkyl group, a lower alkoxy group, a hydroxyl-lower alkyl group, a amino group, a carboxyl-lower alkyl group, an aryl group, a lower alkoxyimino group, a di-lower alkylamino group, an imino group, a carbamoyl group, an acyl group, a heterocyclic group and a heterocyclicthio group; said lower alkyl, lower alkoxy, hydroxyl-lower alkyl, carboxyl-lower alkyl, lower alkoxyimino, imino, carbamoyl, acyl, heterocyclic and heterocyclicthio group for the substituent of $R^8$ may be substituted by at least one substituent selected from the group consisting of a lower alkyl group, a amino group, a carbamoyl group, an oxo group, a hydroxyl-lower alkyl group, an N,N-di-lower alkylamino group, a carboxy-lower alkyl group, a heterocyclic group, a trimethylammonioacetyl group, a ureido group and a guanidino group.

35. An antibacterial agent according to claim 31, wherein $R^7$ and $R^8$ form a heterocyclic ring with the carbon atom to which $R^7$ and $R^8$ are attached.

36. An antibacterial agent according to claim 33, wherein $R^1$ represents a group of the formula:

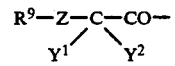

wherein $R^9$ represents a lower alkyl, aryl or heterocyclic group which may be substituted by at least one substituent selected from the group consisting of a halogen atom, a protected or unprotected hydroxyl group, a protected or unprotected amino group, a protected or unprotected amino-lower alkyl group, a protected or unprotected carboxyl group, a lower alkoxy group, a ureido group, a cyano group, a carbamoyloxy group and a nitro group; Z represents an oxygen or sulfur atom or a linkage; $Y^1$ represents a hydrogen atom; $Y^2$ represents a hydrogen atom, a protected or unprotected hydroxyl group, a protected or unprotected carboxyl group, a sulfo group, a sulfoamino group, a protected or unprotected amino group or a group of the formula, $R^{10}CONH-$ in which $R^{10}$ represents a heterocyclic group which may be substituted by at least one substituent selected from the group consisting of a halogen atom, a protected or unprotected hydroxyl group, an oxo group, a lower alkyl group, an aryl group, a cycloalkyl group or a lower alkylsulfonyl group; and $Y^1$ and $Y^2$ form, when taken together, a lower alkoxyimino or aralkyloxyimino group which may be substituted by at least one substituent selected from the group consisting of a halogen atom and a protected or unprotected carboxyl group.

37. An antibacterial agent according to claim 26, wherein the penam derivative is (3R,5R,6R)-3-carboxy-6-[DL-α-(2-chloro-4,5-dihydroxyphenyl)-α-sulfoacetamido]-7-oxo-3-(2-oxo-3-allylideneaminoimidazolidin-1-yl)-4-thia-1-azabicyclo[3.2.0]heptane or a pharmaceutically acceptable salt thereof.

38. An antibacterial agent according to claim 26, wherein the penam derivative is (3R,5R,6R)-3-carboxy-6-[D-α-(2-chloro-4,5-dihydroxyphenyl)-α-sulfoacetamido]-7-oxo-3-(2-oxo-3-semicarbazonoethylideneaminoimidazolidin-1-yl)-4-thia-1-azabicyclo[3.2.0]heptane or a pharmaceutically acceptable salt thereof.

39. An antibacterial agent according to claim 26, wherein the penam derivative is (3R,5R,6R)-3-carboxy-3-{3-[(1,5-dihydroxy-4-oxo-1,4-dihydropyridin-2-yl)methylideneamino]-2-oxoimidazolidin-1-yl}-6-[D-α-(4-ethyl-2,3-dioxo-1-piperazinecarboxamido)-α-(phydroxyphenyl)acetamido]-7-oxo-4-thia-1-azabicyclo-3.2.0]heptane or a pharmaceutically acceptable salt thereof.

40. An antibacterial agent according to claim 26, wherein the penam derivative is (3R,5R,6R)-3-carboxy-3-[3-(3-carboxyallylideneamino)-2-oxoimidazolidin-1-yl]-6-[DL-α-(2-chloro-4,5-dihydroxyphenyl)-α-sulfoacetamido]-7-oxo-4-thia-1-azabicyclo[3.2.0]heptane or a pharmaceutically acceptable salt thereof.

41. An antibacterial agent according to claim 26, wherein the penam derivative is (3R,5R,6R)-6-[2-(2-aminothiazol-4-yl)-2-(Z)-methoxyiminoacetamido]-3-carboxy-3-[3-(1,3-dithiolan-2-ylideneamino)-2-oxoimidazolidin-1-yl]-7-oxo-4-thia-1-azabicyclo-3.2.0]heptane or a pharmaceutically acceptable salt thereof.

42. An antibacterial agent according to claim 26, wherein the penam derivative is (3R,5R,6R)-3-carboxy-6-[D-α-(2-chloro-4-hydroxyphenyl)-α-sulfoacetamido]-7-oxo-3-(2-oxo-3-ureidoimidazolidin-1-yl)-4-thia-1-azabicyclo-3.2.0]heptane or a pharmaceutically acceptable salt thereof.

43. An antibacterial agent according to claim 26, wherein the penam derivative is (3R,5R,6R)-3-carboxy-6-[D-α-(2-chloro-4,5-dihydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

44. An antibacterial agent according to claim 26, wherein the penam derivative is (3R,5R,6R)-3-carboxylato-6-[D-α-(4-ethyl-2,3-dioxo-1-piperazinecarboxamido)-α-(4-hydroxyphenyl)acetamido]-3-{3-[2-(3-methyl-1-imidazolidinium)ethylideneamino]-2-oxoimidazolidin-1-yl}-7-oxo-4-thia-1-azabicyclo[3.2.0]heptane or a pharmaceutically acceptable salt thereof.

45. An antibacterial agent according to claim 26, wherein the penam derivative is (3R,5R,6R)-3-carboxy-6-[D-α-(5-hydroxyl-4-oxo-1,4-dihydropyridin-2-ylcaboxyamido)-α-(p-hydroxyphenyl)acetamido]-3-[3-(1,3-dithiolan-2-ylideneamino)-2-oxoimidazolidin-1-yl]-7-oxo-4-thia-1-azabicyclo[3.2.0]heptane or a pharmaceutically acceptable salt thereof.

46. An antibacterial agent according to claim 26, wherein the penam derivative is (3R,5R,6R)-3-carboxy-6-[D-α-(4-ethyl-2,3-dioxo-1-piperazinecarboxamido)-α-phenylacetamido]-7-oxo-3-[3-(3,4-dihydroxybenzylideneamino)-2-oxoimidazolidin-1-yl]-4-thia-1-azabicyclo[3.2.0]heptane or a pharmaceutically acceptable salt thereof.

47. An antibacterial agent according to claim 26, wherein the penam derivative is (3R,5R,6R)-3-carboxy-6-[D-α-(2-fluoro-4-hydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

48. An antibacterial agent according to claim 26, wherein the penam derivative is (3R,5R,6R)-3-carboxy-6-[D-α-(3-fluoro-4-hydroxyphenyl)-α-sulfoacetamido]-7-oxo-3-ureidoimidazolidin-1-yl)-4-thia-1-azabicyclo[3.2.0]heptane or a pharmaceutically acceptable salt thereof.

49. An antibacterial agent according to claim 26, wherein the penam derivative is (3R,5R,6R)-3-carboxy-6-[D-α-(4-hydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

50. An antibacterial agent according to claim 26, wherein the penam derivative is (3R,5R,6R)-3-carboxy-6-[D-α-(3,4-dihydroxyphenyl)-α-sulfoacetamido]-7-oxo-3-(2-oxo-3-ureidoimidazolidin-1-yl)-4-thia-1-azabicyclo[3.2.0]heptane or a pharmaceutically acceptable salt thereof.

51. A method of treating bacterial infection comprising administering an antibacterially effective amount of a penam derivative or a pharmaceutically acceptable salt thereof as defined in claim 1 to a patient in need thereof.

* * * * *

UNITED STATES PATENT AND TRADEMARK OFFICE
CERTIFICATE OF CORRECTION

PATENT NO. : 5,185,330

DATED : FEBRUARY 9, 1993

INVENTOR(S) : HIROKAZU OCHIAI ET AL

It is certified that error appears in the above-identified patent and that said Letters Patent is hereby corrected as shown below:

On the cover page, Item [30], please add:

--June 8, 1990 [JP]  Japan............02-150514--.

Signed and Sealed this

Fourteenth Day of March, 1995

*Attest:*

BRUCE LEHMAN

*Attesting Officer*        *Commissioner of Patents and Trademarks*

UNITED STATES PATENT AND TRADEMARK OFFICE
CERTIFICATE OF CORRECTION

PATENT NO. : 5,185,330

DATED : February 9, 1993

INVENTOR(S) : Hirokazu Ochiai et al.

It is certified that error appears in the above-identified patent and that said Letters Patent is hereby corrected as shown below:

On title page, item [54] and col. 1, lines 1-3 and item [75],

The title and the fourth inventor's name is incorrect, should be,

--PENAM DERIVATIVES AND SALTS THEREOF AND ANTIBACTERIAL AGENTS COMPRISING THE SAME-- and --Hirohiko Yamamoto--.

COLUMN 149, line 57, "$R^5R^6$" should read --$R^7R^8$--.

Signed and Sealed this

Seventeenth Day of September, 1996

Attest:

BRUCE LEHMAN

*Attesting Officer*    *Commissioner of Patents and Trademarks*